(12) United States Patent
Zhu et al.

(10) Patent No.: US 11,952,582 B2
(45) Date of Patent: Apr. 9, 2024

(54) HERBICIDE-RESISTANCE GENE AND APPLICATION THEREOF IN PLANT BREEDING

(71) Applicant: CAS CENTER FOR EXCELLENCE IN MOLECULAR PLANT SCIENCES, Shanghai (CN)

(72) Inventors: Jiankang Zhu, Shanghai (CN); Vipasha Verma, Shanghai (CN); Feng Li, Shanghai (CN); Meiling Zhang, Shanghai (CN); Ming Li, Shanghai (CN); Mei Chen, Shanghai (CN)

(73) Assignee: CAS CENTER FOR EXCELLENCE IN MOLECULAR PLANT SCIENCES, Shanghai (CN)

( * ) Notice: Subject to any disclaimer, the term of this patent is extended or adjusted under 35 U.S.C. 154(b) by 270 days.

(21) Appl. No.: 16/766,542

(22) PCT Filed: Nov. 23, 2018

(86) PCT No.: PCT/CN2018/117272
§ 371 (c)(1),
(2) Date: May 22, 2020

(87) PCT Pub. No.: WO2019/101179
PCT Pub. Date: May 31, 2019

(65) Prior Publication Data
US 2021/0024949 A1    Jan. 28, 2021

(30) Foreign Application Priority Data

| Nov. 23, 2017 | (CN) | 201711181916.1 |
| Nov. 23, 2017 | (CN) | 201711183983.7 |
| Nov. 23, 2017 | (CN) | 201711183984.1 |
| Nov. 23, 2017 | (CN) | 201711184002.0 |

(51) Int. Cl.
*C12N 15/82* (2006.01)
*C12N 9/02* (2006.01)

(52) U.S. Cl.
CPC ....... *C12N 15/8274* (2013.01); *C12N 9/0069* (2013.01); *C12Y 113/11027* (2013.01)

(58) Field of Classification Search
CPC .................................................. C12N 15/8274
See application file for complete search history.

(56) References Cited

U.S. PATENT DOCUMENTS 6,245,968 B1 *   6/2001   Boudec .............. C12N 15/8274
800/300

FOREIGN PATENT DOCUMENTS

| CN | 102906252 A | 1/2013 | |
| WO | WO-2010085705 A2 * | 7/2010 | ............. A01N 41/10 |

OTHER PUBLICATIONS

Mastringe M. et al. "P-Hydroxyphenylpyruvate Dioxygenase Inhibitor-Resistant Plants" Pest Management Science, vol. 61, No. (3), Jan. 4, 2005 (Jan 4, 2005), ISSN: 1526-4998.

* cited by examiner

Primary Examiner — Mykola V. Kovalenko
(74) Attorney, Agent, or Firm — Polsinelli, PC; Tara A. Nealey

(57) ABSTRACT

Provided are a mutant HPPD polypeptide having high resistance to a herbicide and an encoding gene thereof, and an application thereof in an improved plant. The amino acid at position 282 of the mutant HPPD polypeptide is mutated from arginine to serine at a wild-type HPPD polypeptide. In addition, the mutant HPPD polypeptide further comprises an amino acid at position 349 that is mutated from glutamic acid to lysine, and/or an amino acid at position 156 that is mutated from alanine to valine. The mutated HPPD polypeptide can be used for cultivating plants having resistance to a herbicide having HPPD inhibition.

6 Claims, 13 Drawing Sheets
(12 of 13 Drawing Sheet(s) Filed in Color)
Specification includes a Sequence Listing.

HERBICIDE-RESISTANCE GENE AND APPLICATION THEREOF IN PLANT BREEDING

RELATED APPLICATIONS

This application is a national stage filing under 35 U.S.C. § 371 of international application number PCT/CN2018/117272, filed on Nov. 23, 2018, which claims the benefit of priority to Chinese Patent Application No. 201711184002.0, filed on Nov. 23, 2017, Chinese Patent Application No. 201711183984.1 filed on Nov. 23, 2017, Chinese Patent Application No. 201711181916.1, filed on Nov. 23, 2017, and Chinese Patent Application No. 201711183983.7 filed on Nov. 23, 2017. The entire contents of each of the prior applications are herein incorporated by reference.

TECHNICAL FIELD

The present invention relates to the field of botany, and more specifically to herbicide-resistance gene and application thereof in plant breeding.

BACKGROUND

4-Hydroxyphenylpyruvate Dioxygenase (HPPD, EC 1.13.11.27) exists in various organisms and it is a key enzyme that catalyzes the oxygenation of 4-hydroxyphenylpyruvate (HPP, the degradation product of tyrosine) to produce homogentisate (HGA). In animals, the main function of HPPD is to promote the catabolism of tyrosine, aromatic amino acid and phenylalanine. However, its function in plants is significantly different from that in animals. It is a key precursor in the biosynthesis of homogentisic acid to form plastoquinones and tocopherols (vitamin E). Tocopherols act as membrane-related antioxidants and are essential antioxidants for plant growth. Plastoquinones is firstly an electron carrier between PSII and cytochrome b6/f complex, which enables electrons from photosynthesis system II to photosynthesis system I, thereby converting light energy into chemical energy. Then it is an oxidation-reduction cofactor of phytoene desaturase involved in carotenoid biosynthesis, while the carotenoid protect plants from sunlight.

Inhibition of HPPD will lead to uncoupling of photosynthesis in plant cells and lack of auxiliary light-harvesting pigments. At the same time, due to the lack of photoprotection normally provided by carotenoids, reactive oxygen intermediates and photooxidation cause chlorophyll destruction, resulting in albinism in the photosynthetic tissues of plants, and the growth is inhibited until death. Therefore, HPPD has been identified as an herbicide target since the 1990s.

HPPD inhibitory herbicides have proved to be very effective selective herbicides with spectral herbicidal activity, which can be used both before and after buds, with high activity, low residues, safety for mammals and environmental friendliness, etc. At present, five herbicides targeting HPPD have been developed, mainly comprising triketones, pyridones, isoxazolones, diketonitriles and benzophenones according to their structure. The global sales of such HPPD inhibitor herbicides have increased sharply since 2005, reaching US $ 864 million in 2010. The global sales in 2013 and 2014 were US $ 1.342 billion and US $ 1.392 billion, respectively. In 2014, it ranked 13th in the sales of the world's top 20 pesticide types, and the market has great potential for future development.

These HPPD inhibitory herbicides also cause some damage to crops when they indiscriminately kill weeds, so it is particularly important to obtain crops that are tolerant to herbicides. In addition to attempting to bypass the production of homogentisic acid mediated by HPPD, the current strategy also comprises overexpression of the enzyme to produce large amounts of herbicide target enzymes in plants, thereby reducing the inhibitory effect of herbicides. The overexpression of HPPD makes the plants have better pre-emergence tolerance to the diketonitrile derivative (DKN) of isoxaflutole, but the tolerance is not enough to resist the herbicide treatment after germination. Another strategy is to mutate HPPD to obtain a target enzyme that is more tolerant to HPPD inhibitors than the pre-mutation natural HPPD, while retaining its role in catalyzing the conversion of HPPD to homogentisic acid. This strategy has been successfully applied to two HPPD inhibitors of the diketonitrile family.

Although the development of plants that are tolerant to HPPD inhibitors in the field has achieved certain research progress, it is still necessary to develop and improve the tolerance system for HPPD inhibitors, especially for the triketones (such as sulcotrione, mesotrione and tembotrion) HPPD inhibitors.

SUMMARY OF THE INVENTION

The object of the present invention is to provide an HPPD resistance gene with high resistance to HPPD inhibitors and application thereof.

In a first aspect of the present invention, it is provides an isolated herbicide-resistance polypeptide, which is a mutant HPPD polypeptide, and the mutant HPPD polypeptide is mutated from arginine (R) to serine (S) or threonine (T) at the amino acid of position 282 of the wild-type HPPD polypeptide corresponding to SEQ ID NO: 2;

or a first resistance-sensitive site of herbicide according to the eighth aspect of the present invention of the mutant HPPD polypeptide is serine (S) or threonine (T).

In another preferred embodiment, the herbicide-resistance polypeptide further comprise one or more mutations selected from the group consisting of:
(a) the amino acid at position 156 is mutated from alanine (A) to valine (V) or leucine (L); and/or (b) the amino acid at position 349 is mutated from glutamic acid (E) to lysine (K) or arginine (R), of the wild-type HPPD polypeptide corresponding to SEQ ID NO: 2.

In another preferred embodiment, the herbicide-resistance polypeptide further comprise one or more mutations selected from the group consisting of:
(a) the second resistance-sensitive site is mutated to lysine (K) or arginine (R); and/or
(B) the third resistance-sensitive site is mutated to valine (V) or leucine (L).

In another preferred embodiment, the herbicide-resistance polypeptide is mutated from arginine (R) to serine (S) or threonine (T) only at the amino acid of position 282 of the wild-type HPPD polypeptide corresponding to SEQ ID NO: 2; or the first resistance-sensitive site of the herbicide-resistance polypeptide is serine (S) or threonine (T).

In another preferred embodiment, the herbicide-resistance polypeptide is (i) mutated from arginine (R) to serine (S) or threonine (T) at the amino acid of position 282; and (ii) mutated from glutamic acid (E) to lysine (K) or arginine (R) at the amino acid of position 349, of wild-type HPPD polypeptide corresponding to SEQ ID NO: 2; or the first herbicide-resistance-sensitive site of the herbicide-resistance polypeptide is serine (S) or threonine (T); and the second herbicide-resistance-sensitive site is lysine (K) or arginine (R).

In another preferred embodiment, the herbicide-resistance polypeptide is (i) mutated from arginine (R) to serine (S) or threonine (T) at the amino acid of position 282; and (ii) mutated from alanine (A) to valine (V) or leucine (L) at the amino acid of position 156, of wild-type HPPD polypeptide corresponding to SEQ ID NO: 2; or the first resistance-sensitive site of the herbicide-resistance polypeptide is serine (S) or threonine (T); and the third resistance-sensitive site is valine (V) or leucine (L).

In another preferred embodiment, the herbicide-resistance polypeptide is (i) mutated from arginine (R) to serine (S) or threonine (T) at the amino acid of position 282; (ii) mutated from glutamic acid (E) to lysine (K) or arginine (R) at the amino acid of position 349; and (iii) mutated from alanine (A) to valine (V) or leucine (L) at the amino acid of position 156, of wild-type HPPD polypeptide corresponding to SEQ ID NO: 2; or the first resistance-sensitive site of the herbicide-resistance polypeptide is serine (S) or threonine (T); the second herbicide-resistance-sensitive site is lysine (K) or arginine (R); and the third resistance-sensitive site is valine (V) or leucine (L).

wherein, the first, second and third resistance-sensitive sites of the herbicide-resistance polypeptide are all described in the eighth aspect of the present invention.

In another preferred embodiment, the tolerance concentration V1 of the herbicide-resistance polypeptide to an herbicide is compared with the tolerance concentration V2 of the wild-type HPPD polypeptide to the same herbicide, and V1/V2≥2, preferably V1/V2≥5, more preferably V1N2≥10.

In another preferred embodiment, the herbicide-resistance polypeptide is a polypeptide having the amino acid sequence as shown in SEQ ID NO: 4, SEQ ID NO: 6, SEQ ID NO: 8, and/or SEQ ID NO: 10, active fragment or conservative variant polypeptide thereof.

In another preferred embodiment, the mutated HPPD polypeptide is mutated from arginine to serine at the amino acid of position 282 of the wild-type HPPD polypeptide corresponding to SEQ ID NO: 2.

In another preferred embodiment, the mutant HPPD polypeptide is mutated from glutamic acid to lysine at the amino acid of position 349 of the wild-type HPPD polypeptide corresponding to SEQ ID NO: 2; and/or the mutated HPPD polypeptide is mutated from alanine to valine at the amino acid of position 156 of the wild-type HPPD polypeptide corresponding to SEQ ID NO: 2.

In another preferred embodiment, the HPPD polypeptide is derived from *Pseudomonas aeruginosa*.

In another preferred embodiment, the herbicide is an HPPD inhibitor, preferably a triketone HPPD inhibitor.

In another preferred embodiment, the triketone HPPD inhibitor is selected from the group consisting of sulcotrione, mesotrione, tembotrion, and a combination thereof.

In another preferred embodiment, the herbicide-resistance polypeptide can tolerate herbicide with a concentration of at least 10 μM, preferably 50 μM, more preferably 100 μM.

In another preferred embodiment, the herbicide-resistance polypeptide is selected from the group consisting of:
(a) a polypeptide having the amino acid sequence shown in SEQ ID NO: 4, SEQ ID NO: 6, SEQ ID NO: 8, and/or SEQ ID NO: 10;
(b) a polypeptide having herbicide tolerance and derived from (a), and formed by substitution, deletion, or addition of one or more (for example 2, 3, 4 or 5) amino acid residue(s) with the amino acid sequence shown in SEQ ID NO: 4, SEQ ID NO: 6, SEQ ID NO: 8, and/or SEQ ID NO: 10.

In another preferred embodiment, the amino acid at position 282 corresponding to SEQ ID NO: 4 of the derived polypeptide is serine.

In another preferred embodiment, the homology between the derived polypeptide and the sequence shown in SEQ ID NO: 4 is at least 60%, preferably at least 70%, more preferably at least 80%, and most preferably at least 90%, such as 95%, 97%, 99%.

In another preferred embodiment, the amino acid at position 282 corresponding to SEQ ID NO: 6 of the derived polypeptide is serine, and the amino acid at position 349 is lysine.

In another preferred embodiment, the amino acid at position 282 corresponding to SEQ ID NO: 8 of the derived polypeptide is serine, and the amino acid at position 156 is valine.

In another preferred embodiment, the amino acid at position 282 corresponding to SEQ ID NO: 10 of the derived polypeptide is serine, the amino acid at position 349 is lysine, and the amino acid at position 156 is valine.

In another preferred embodiment, the herbicide-resistance polypeptide is formed by mutation of the wild-type HPPD polypeptide shown in SEQ ID NO: 2.

In a second aspect of the invention, it provides an isolated polynucleotide encoding the herbicide-resistance polypeptide of the first aspect of the invention.

In another preferred embodiment, the polynucleotide is selected from the group consisting of:
(a) a polynucleotide encoding a polypeptide as shown in SEQ ID NO: 4;
(b) a polynucleotide having a sequence as shown in SEQ ID NO: 3;
(c) a polynucleotide having a nucleotide sequence of ≥80% (preferably ≥90%, more preferably ≥95%, most preferably ≥98%) homologous to the sequence of SEQ ID NO: 3, and encoding a polypeptide as shown in SEQ ID NO: 4;
(d) a polynucleotide complementary to the polynucleotide of any of (a) to (c).

In another preferred embodiment, the polynucleotide is selected from the group consisting of:
(a) a polynucleotide encoding a polypeptide as shown in SEQ ID NO: 6;
(b) a polynucleotide having a sequence as shown in SEQ ID NO: 5;
(c) a polynucleotide having a nucleotide sequence of ≥80% (preferably ≥90%, more preferably ≥95%, most preferably ≥98%) homologous to the sequence of SEQ ID NO: 5, and encoding a polypeptide as shown in SEQ ID NO: 6;
(d) a polynucleotide complementary to the polynucleotide of any of (a) to (c).

In another preferred embodiment, the polynucleotide is selected from the group consisting of:
(a) a polynucleotide encoding a polypeptide as shown in SEQ ID NO: 8;
(b) a polynucleotide having a sequence as shown in SEQ ID NO: 7;
(c) a polynucleotide having a nucleotide sequence of ≥80% (preferably ≥90%, more preferably ≥95%, most preferably ≥98%) homologous to the sequence of SEQ ID NO: 7, and encoding a polypeptide as shown in SEQ ID NO: 8;
(d) a polynucleotide complementary to the polynucleotide of any of (a) to (c).

In another preferred embodiment, the polynucleotide is selected from the group consisting of:
(a) a polynucleotide encoding a polypeptide as shown in SEQ ID NO: 10;
(b) a polynucleotide having a sequence as shown in SEQ ID NO: 9;
(c) a polynucleotide having a nucleotide sequence of ≥80% (preferably ≥90%, more preferably ≥95%, most preferably ≥98%) homologous to the sequence of SEQ ID NO: 9, and encoding a polypeptide as shown in SEQ ID NO: 10;
(d) a polynucleotide complementary to the polynucleotide of any of (a) to (c).

In another preferred embodiment, the polynucleotide is selected from the group consisting of genomic sequence, cDNA sequence, RNA sequence, and a combination thereof.

In another preferred embodiment, the polynucleotide additionally comprises a auxiliary element flanking the ORF of the herbicide-resistance polypeptide, and the auxiliary element is selected from the group consisting of a signal peptide, a secretory peptide, a tag sequence (such as 6His), and a combination thereof.

In another preferred embodiment, the polynucleotide further comprises a promoter operably linked to the ORF sequence of the herbicide-resistance polypeptide.

In another preferred embodiment, the promoter is selected from the group consisting of a constitutive promoter, a tissue-specific promoter, an inducible promoter, or a strong promoter.

In a third aspect of the invention, it provides a vector comprising the polynucleotide of the second aspect of the invention.

In another preferred embodiment, the vector comprises an expression vector, a shuttle vector, and an integration vector.

In a fourth aspect of the invention, it provides a host cell comprising the vector of the third aspect of the invention or having the polynucleotide of the second aspect of the invention integrated into its genome.

In another preferred embodiment, the host cell is selected from the group consisting of a plant cell, an animal cell, a prokaryotic cell, and a yeast cell.

In a fifth aspect of the invention, it provides a method for preparing an herbicide-resistance polypeptide, which comprises the steps of:
(i) culturing the host cell of the fourth aspect of the invention under conditions suitable for expression, thereby expressing the herbicide-resistance polypeptide; and
(b) isolating the herbicide-resistance polypeptide.

In a sixth aspect of the invention, it provides a method for improving a plant, which comprises the steps of:
(a) providing a plant cell, and genetically engineering the plant cell to express the herbicide-resistance polypeptide of the first aspect of the invention;
(B) regenerating the plant cell in step (a) into a plant.

In another preferred embodiment, the step (a) comprises the steps of:
(1) providing a Agrobacterium tumefacien containing an expression vector, wherein the expression vector contains the DNA coding sequence of the herbicide-resistance polypeptide of the first aspect of the invention;
(2) contacting a plant cell with the Agrobacterium tumefacien in step (1), thereby the DNA encoding sequence of the herbicide-resistance polypeptide being transferred into the plant cell and integrated into the chromosome of the plant cell; and
(3) selecting the plant cell into which the DNA coding sequence of the herbicide-resistance polypeptide has been transferred.

In another preferred embodiment, in step (a), modifying the plant cell by gene editing technology to express the herbicide-resistance polypeptide of the first aspect of the invention.

In another preferred embodiment, in step (a), modifying the plant cell by gene editing technology so that the HPPD in the plant cell is mutated from arginine (R) to serine (S) or threonine (T) at a conservative site corresponding to the amino acid of position 282 of SEQ ID NO: 2.

In another preferred embodiment, in step (a), the method further comprises modifying the plant cell by gene editing technology so that the HPPD in the plant cell is (i) mutated from glutamic acid (E) to lysine (K) or arginine (R) at a conservative site corresponding to the amino acid of position 349 of SEQ ID NO: 2; and/or (ii) mutated from alanine (A) to valine (V) or leucine (L) at a conservative site corresponding to the amino acid of position 156 of SEQ ID NO: 2.

In another preferred embodiment, in step (a), modifying the plant cell by gene editing technology so that the HPPD in the plant cell is mutated from arginine (R) to serine (S) or threonine (T) at a conservative site corresponding to the amino acid of position 282 of SEQ ID NO: 2 and mutated from glutamic acid (E) to lysine (K) or arginine (R) at a conservative site corresponding to the amino acid of position 349 of SEQ ID NO: 2.

In another preferred embodiment, in step (a), modifying the plant cell by gene editing technology so that the HPPD in the plant cell is mutated from arginine (R) to serine (S) or threonine (T) at a conservative site corresponding to the amino acid of position 282 of SEQ ID NO: 2 and mutated from alanine (A) to valine (V) or leucine (L) at a conservative site corresponding to the amino acid of position 156 of SEQ ID NO: 2.

In another preferred embodiment, in step (a), modifying the plant cell by gene editing technology so that the HPPD in the plant cell is (i) mutated from arginine (R) to serine (S) or threonine (T) at a conservative site corresponding to the amino acid of position 282; (ii) mutated from glutamic acid (E) to lysine (K) or arginine (R) at a conservative site corresponding to the amino acid of position 349; and (iii) mutated from alanine (A) to valine (V) or leucine (L) at a conservative site corresponding to the amino acid of position 156 of SEQ ID NO: 2.

In another preferred embodiment, the plant is *Arabidopsis thaliana*, and the amino acid of position 349 of HPPD (NCBI accession number: 6532701544) in the *Arabidopsis* cell is mutated from arginine (R) to serine (S) or threonine (T).

In another preferred embodiment, the *Arabidopsis* cell further comprises a mutation at position 433 from glutamic acid (E) to lysine (K) or arginine (R), and/or a mutation at position 214 from serine (S) to valine (V) or leucine (L).

In another preferred embodiment, the amino acid of position 349 of HPPD in the *Arabidopsis* cell is mutated from arginine (R) to serine (S) or threonine (T), and the position 433 thereof is mutated from glutamic acid (E) to lysine (K) or arginine (R).

In another preferred embodiment, the amino acid of position 349 of HPPD in the *Arabidopsis* cell is mutated from arginine (R) to serine (S) or threonine (T), and the position 214 thereof is mutated from serine (S) to valine (V) or leucine (L).

In another preferred embodiment, the amino acid of position 349 of HPPD in the *Arabidopsis* cell is mutated from arginine (R) to serine (S) or threonine (T), the position 433 thereof is mutated from glutamic acid (E) to lysine (K) or arginine (R), and the position 214 thereof is mutated from serine (S) to valine (V) or leucine (L).

In another preferred embodiment, the plant is rice, and the amino acid of position 346 of HPPD (NCBI accession number: XP_015626163) in the rice cell is mutated from arginine (R) to serine (S) or threonine (T).

In another preferred embodiment, the rice cell further comprises a mutation at position 430 from glutamic acid (E) to lysine (K) or arginine (R), and/or a mutation at position 213 from alanine (A) to valine (V) or leucine (L).

In another preferred embodiment, the amino acid of position 346 of HPPD in the rice cell is mutated from arginine (R) to serine (S) or threonine (T), and the position 430 thereof is mutated from glutamic acid (E) to lysine (K) or arginine (R).

In another preferred embodiment, the amino acid of position 346 of HPPD in the rice cell is mutated from arginine (R) to serine (S) or threonine (T), and the position 213 thereof is mutated from alanine (A) to valine (V) or leucine (L).

In another preferred embodiment, the amino acid of position 346 of HPPD in the rice cell is mutated from arginine (R) to serine (S) or threonine (T), the position 430 thereof is mutated from glutamic acid (E) to lysine (K) or arginine (R), and the position 213 thereof is mutated from alanine (A) to valine (V) or leucine (L).

In another preferred embodiment, the plant is soybean, and the amino acid of position 395 of first HPPD (NCBI accession number: NP_001235148) in the soybean cell is mutated from arginine (R) to serine (S) or threonine (T).

In another preferred embodiment, the soybean cell further comprises a mutation at position 479 from glutamic acid (E) to lysine (K) or arginine (R), and/or a mutation at position 259 from serine (S) to valine (V) or leucine (L).

In another preferred embodiment, the amino acid of position 395 of HPPD in the soybean cell is mutated from arginine (R) to serine (S) or threonine, and the position 479 thereof is mutated from glutamic acid (E) to lysine (K) or arginine (R).

In another preferred embodiment, the amino acid of position 395 of HPPD in the soybean cell is mutated from arginine (R) to serine (S) or threonine (T), and the position 259 thereof is mutated from serine (S) to valine (V) or leucine (L).

In another preferred embodiment, the amino acid of position 395 of HPPD in the soybean cell is mutated from arginine (R) to serine (S) or threonine (T), the position 479 thereof is mutated from glutamic acid (E) to lysine (K) or arginine (R), and the position 259 thereof is mutated from serine (S) to valine (V) or leucine (L).

In another preferred embodiment, the gene editing technology is selected from the group consisting of CRISPR gene editing system, error-prone PCR, genetic recombination, TALEN and ZFN.

In another preferred embodiment, the gene editing technology comprises any technical method that can generate the mutation.

In another preferred embodiment, in step (a), comprising the steps of:
(a1) determining the site to be modified corresponds to the herbicide-resistance-sensitive site of the eighth aspect of the invention in the HPPD polypeptide of the plant to be modified through homology alignment, wherein the herbicide-resistance-sensitive site comprises the first resistance-sensitive site;
(a2) genetically engineering the plant cell so that the first herbicide-resistance-sensitive site of the HPPD polypeptide expressed by the plant cell is serine (S) or threonine (T).

In another preferred embodiment, the herbicide-resistance-sensitive sites further comprise: the second resistance-sensitive sites and/or the third resistance-sensitive sites.

In another preferred embodiment, the step (a2) further comprises genetically engineering the plant cell so that (i) the second resistance-sensitive site of the HPPD polypeptide expressed by the plant cell is mutated to lysine (K) or arginine (R); and/or (ii) the third resistance-sensitive site is mutated to valine (V) or leucine (L).

In another preferred embodiment, the step (a2) further comprises modifying the plant cell so that the first herbicide-resistance-sensitive site of the HPPD polypeptide expressed by the plant cell is serine (S) or threonine (T), and the second herbicide-resistance-sensitive site is lysine (K) or arginine (R).

In another preferred embodiment, the step (a2) further comprises modifying the plant cell so that the first herbicide-resistance-sensitive site of the HPPD polypeptide expressed by the plant cell is serine (S) or threonine (T), and the second herbicide-resistance-sensitive site is valine (V) or leucine (L).

In another preferred embodiment, the step (a2) further comprises modifying the plant cell so that the first herbicide-resistance-sensitive site of the HPPD polypeptide expressed by the plant cell is serine (S) or threonine (T), the second herbicide-resistance-sensitive site is lysine (K) or arginine (R), and the third herbicide-resistance-sensitive site is valine (V) or leucine (L).

In another preferred embodiment, the method improves the herbicide tolerance of a plant.

In another preferred embodiment, the plant comprises crops, forestry plant, vegetables, fruits, flowers, pastures (including turfgrass); preferably, comprises gramineous, leguminous and cruciferous plants; and more preferably, comprises rice, maize, sorghum, wheat, soybean or *Arabidopsis thaliana*.

In another preferred embodiment, the plant comprise: *Arabidopsis thaliana,* rice, wheat, maize, sorghum, or tomato.

In another preferred embodiment, after step (4), a step of testing the herbicide tolerance of the plant is further comprised.

In another preferred embodiment, the plant seedlings can tolerate an herbicide with a concentration of at least 200 μM, preferably 400 μM, more preferably 600 μM.

In another preferred embodiment, the plant improved by the method can tolerate an herbicide (sulcotrione, mesotrione and tembotrion) with a concentration of at least 50 nM, preferably 100 nM, and more preferably 200 nM before or after germination.

In a seventh aspect of the invention, it provides a use of the herbicide-resistance polypeptide of the first aspect of the invention or encoding gene thereof, for cultivating herbicide-resistance lines of a plant, or for the preparation of a reagent or a kit for cultivating herbicide-resistance lines of a plant.

In an eighth aspect of the invention, it provides an herbicide-resistance-sensitive site selected from the group consisting of:

(I) a first resistance-sensitive site, which corresponds to (i) the amino acid of position 282 of the wild-type HPPD polypeptide derived from *Pseudomonas aeruginosa*, (ii) the amino acid of position 349 of the wild-type HPPD polypeptide derived from *Arabidopsis thaliana*, (iii) the amino acid of position 346 of the wild-type HPPD polypeptide derived from rice, (iv) the amino acid of position 395 of the wild-type HPPD polypeptide derived from soybean, or (v) the amino acid of position 341 of the wild-type HPPD polypeptide derived from tomato;

(II) a second resistance-sensitive site, which corresponds to (i) the amino acid of position 349 of the wild-type HPPD polypeptide derived from *Pseudomonas aeruginosa*, (ii) the amino acid of position 433 of the wild-type HPPD polypeptide derived from *Arabidopsis thaliana*, (iii) the amino acid of position 430 of the wild-type HPPD polypeptide derived from rice, (iv) the amino acid of position 479 of the wild-type HPPD polypeptide derived from soybean, or (v) the amino acid of position 425 of the wild-type HPPD polypeptide derived from tomato; and/or (III) a third resistance-sensitive site, which corresponds to (i) the amino acid of position 156 of the wild-type HPPD polypeptide derived from Pseudomonas aeruginosa, (ii) the amino acid of position 214 of the wild-type HPPD polypeptide derived from *Arabidopsis thaliana*, (iii) the amino acid of position 213 of the wild-type HPPD polypeptide derived from rice, (iv) the amino acid of position 259 of the wild-type HPPD polypeptide derived from soybean, or (v) the amino acid of position 209 of the wild-type HPPD polypeptide derived from tomato.

In another preferred embodiment, the polypeptide is sensitive and insensitive, when the site is arginine (R), the polypeptide is sensitive, and the polypeptide is sensitive to herbicides; when the site is serine (S) or threonine (T), the polypeptide is insensitive, and the polypeptide is resistant to herbicides, preferably, the tolerance concentration V1 of the insensitive polypeptide to an herbicide is compared with the tolerance concentration V2 of the sensitive polypeptide to the same herbicide, and V1/V2≥2, preferably V1/V2≥5, more preferably V1/V2≥10.

In another preferred embodiment, the polypeptide is sensitive and insensitive, when the first resistance-sensitive site is arginine (R) and the second resistance-sensitive site is glutamic acid (E), the polypeptide is sensitive, and the polypeptide is sensitive to herbicides; when the first resistance-sensitive site is serine (S) or threonine (T) and the second resistance-sensitive site is lysine (K) or arginine (R), the polypeptide is insensitive, and the polypeptide is resistant to herbicides.

In another preferred embodiment, the polypeptide is sensitive and insensitive, when the first resistance-sensitive site is arginine (R) and the second resistance-sensitive site is alanine (A), the polypeptide is sensitive, and the polypeptide is sensitive to herbicides; when the first resistance-sensitive site is serine (S) or threonine (T) and the second resistance-sensitive site is valine (V) or leucine (L), the polypeptide is insensitive, and the polypeptide is resistant to herbicides.

In another preferred embodiment, the polypeptide is sensitive and insensitive, when the first resistance-sensitive site is arginine (R), the second resistance-sensitive site is gluta-mic acid (E), and the third resistance-sensitive site is alanine (A), the polypeptide is sensitive, and the polypeptide is sensitive to herbicides; when the first resistance-sensitive site is serine (S) or threonine (T), the second resistance-sensitive site is lysine (K) or arginine (R), and the third resistance-sensitive site is valine (V) or leucine (L), the polypeptide is insensitive, and the polypeptide is resistant to herbicides.

In another preferred embodiment, the insensitive polypeptide is the herbicide-resistance polypeptide of the first aspect of the invention, and the sensitive polypeptide is a wild-type HPPD polypeptide.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

DESCRIPTION OF DRAWINGS

"The patent or application file contains at least one drawing executed in color. Copies of this patent or patent application with color drawing(s) will be provided by the Office by request and payment of the necessary fee."

FIG. 14 shows the resistance to herbicides (mesotrione and sulcotrione) during and after germination of *Arabidopsis.* Wherein, FIG. 14A shows the germination photograph of *Arabidopsis* overexpression lines in the presence of mesotrione. FIG. 14B shows the germination photograph of *Arabidopsis* overexpression lines in the presence of sulcotrione. FIG. 14C shows the post-germination photograph of *Arabidopsis* overexpression lines in the presence of mesotrione. FIG. 14D shows the total chlorophyll content of *Arabidopsis* overexpression lines in the presence of mesotrione. FIG. 14E shows the carotenoid content of the *Arabidopsis* overexpression line in the presence of mesotrione. Abbreviations: WT (Co10); OE At: overexpression line of AtHPPD; OE Pa: overexpression line of PaHPPD; OE M3: overexpression line of PaHPPD-M3. Wherein, AtHPPD represents the HPPD gene derived from *Arabidopsis (Arabidopsis thaliana),* PaHPPD represents the HPPD gene derived from *Pseudomonas aeruginosa,* and PaHPPD-M3 represents the PaHPPD mutant gene with a mutation at position 844 from C to A.

FIGS. 17C and 17D respectively show the DAB dyeing results of two-week old seedlings of WT (Co10), OE At, OE Pa, and OE M3 cultured in the control medium CA MS medium without herbicide) and herbicide-containing Medium CA MS medium containing 100 nM mesotrione) for 72 h.

FIG. 18A shows photographs of WT and TO generation of OE SDM rice lines 3 weeks after the treatment with 200 μM mesotrione (prepared with 0.1% Tween-20) and 0.1% Tween-20 (control). FIG. 18B shows the quantitative analysis of the total chlorophyll content of WT and OE SDM rice leaves 2 weeks after spraying with 0.1% Tween-20 (control) and 200 μM mesotrione (prepared with 0.1% Tween-20).Wherein the abbreviations have the following meanings: WT: wild type rice; OE SDM: TO generation of PaHPPD-SDM overexpressing rice line.

FIG. 19A and FIG. 19B show the NBT dyeing photographs of WT and OE SDM rice seedling leaves 1 week after spraying treatment with control (0.1% Tween-20) and 200 μM mesotrione. FIG. 19C and FIG. 19D show the DAB dyeing photographs of WT and OE SDM rice seedling leaves 1 week after spraying treatment with control (0.1% Tween-20) and 200 μM mesotrione. FIG. 19E shows the lipid peroxidation (MDA) content in WT and OE SDM rice seedling leaves 1 week after spraying treatment with control (0.1% Tween-20) and 200 μM mesotrione.

MODES FOR CARRYING OUT THE PRESENT INVENTION

Figure 1:
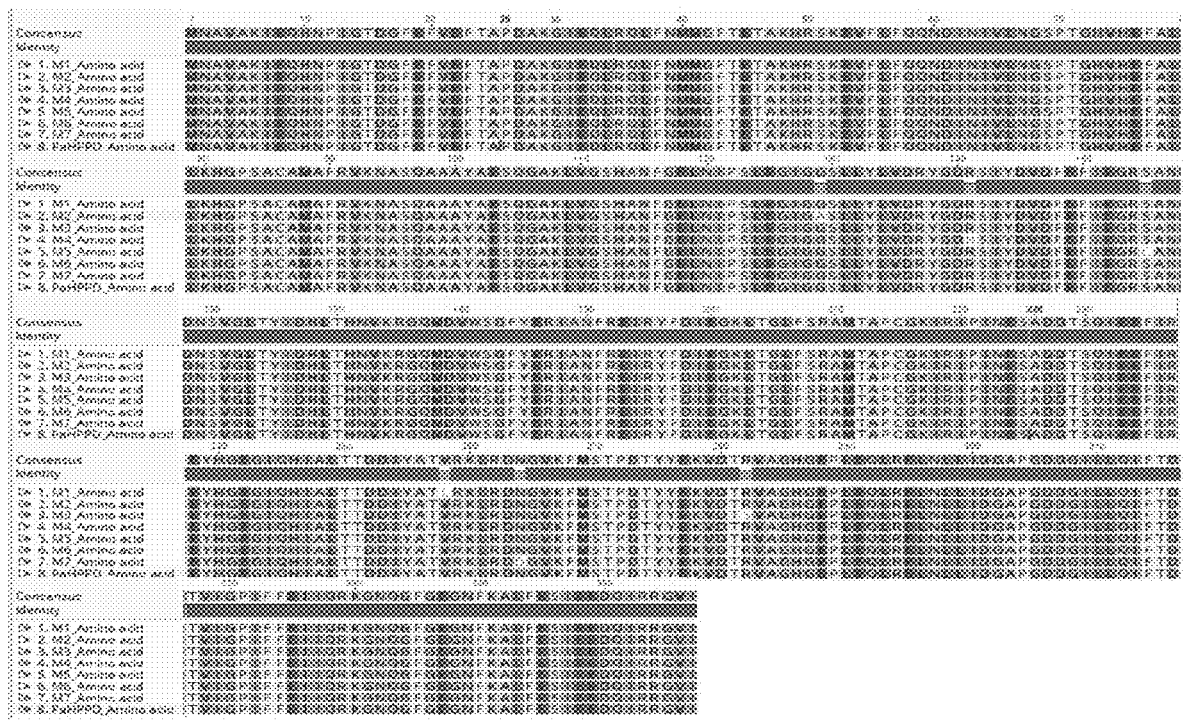
FIG. 1 shows the amino acid sequence alignment of the wild type (WT) PaHPPD and the first round ep -PCR mutants (M1 to M7).

After extensive and intensive research, the inventors unexpectedly discovered HPPD inhibitor resistance genes PaHPPD-M3, PaHPPD-DS18, PaHPPD-DS73 and PaHPPD-SDM derived from Pseudomonas aeruginosa with high resistance to HPPD inhibitor and applications thereof, for the first time. Specifically, the invention relates to nucleic acid sequences, mutation sites and amino acid sequences of HPPD mutants PaHPPD-M3, PaHPPD-DS18, PaHPPD-DS73 and PaHPPD-SDM, and stability resistance detection in microorganisms. Experiments show that plant Arabidopsis introduced with the mutant gene showed significant HPPD inhibitory herbicide-resistance. The mutant gene has a very broad application prospect in the field of breeding HPPD inhibitory herbicide-tolerant plants. The present invention has been completed on the basis of this.

Specifically, the presence of tyrosine aminotransferase in E. coli DH5a can catalyze the production of p-hydroxyphenylpyruvate (4-HPP) from tyrosine, which is used as a substrate for HPPD to produce homogentisic acid (HGA). After further oxidation and polymerization, a brown substance is produced. The addition of HPPD inhibitors will inhibit this reaction, thereby reducing the production of pigment. Therefore, the gradation of pigment can be used as an inhibition index of HPPD activity. By optimizing some of the properties of the pigment and the optimal conditions for higher resolution pigments, the inventors established a high-throughput E. coli screening system of tembotrion herbicide-resistance genes based on 96-well plates. Through heterologous expression of HPPD mutant genes from different species in E. coli DH5α, the resistance characteristics of E. coli DH5α-mutated gene to triketone herbicides were analyzed by detecting the absorption value of pigment at 405 nm (FIGS. 2-6, 8 and 9). The system can perform qualitative and quantitative detection sensitively and quickly, and has the advantages of low cost, small size and simple reaction system.

Using the E. coli pigment screening system, the invention obtained four new mutant HPPD enzymes, all of which retain the activity of catalyzing the conversion of p-hydroxyphenylpyruvate (HPP) to homogentisic acid and have higher tolerance to HPPD inhibitors than that of the original unmutated HPPD. The first HPPD mutant is PaHPPD-M3, wherein the arginine at position 282 of PaHPPD of Pseudomonas aeruginosa is mutated to serine (R282S). Specifically, the nucleic acid sequence, mutation site (C844A) and amino acid sequence of HPPD mutant PaHPPD-M3 are involved.

The second HPPD mutant is PaHPPD-DS18, wherein the arginine at position 282 of PaHPPD of Pseudomonas aeruginosa is mutated to serine (R282S) and the glutamic acid at position 349 is mutated to lysine (E349K). Specifically, the nucleic acid sequence, mutation sites (C844A, G216A and G1045A) and amino acid sequence of HPPD mutant PaHPPD-DS18 are involved.

The third HPPD mutant is PaHPPD-DS73, wherein the arginine at position 282 of PaHPPD of Pseudomonas aeruginosa is mutated to serine (R282S) and the alanine at position 156 is mutated to valine (A156V). Specifically, the nucleic acid sequence, mutation sites (C844A and C467T) and amino acid sequence of HPPD mutant PaHPPD-DS73 are involved.

The fourth HPPD mutant is PaHPPD-SDM, wherein the arginine at position 282 of PaHPPD of Pseudomonas aeruginosa is mutated to serine (R282S), the glutamic acid at position 349 is mutated to lysine (E349K) and the alanine at position 156 is mutated to valine (A156V). Specifically, the nucleic acid sequence, mutation sites (G216A, C467T, C844A and G1045A) and amino acid sequence of HPPD mutant PaHPPD-SDM are involved. The nucleic acid sequences, mutation sites and amino acid sequences of the mutants PaHPPD-M3, PaHPPD-DS18, PaHPPD-DS73 and PaHPPD-SDM according to the present invention are provided. Further, the resistance of the mutant gene at the microbial level is provided, wherein the mutants PaHPPD-M3, PaHPPD-DS18 and PaHPPD-DS73 led to a tolerance of up to 100 μM against three triketone herbicides (sulcotrione, mesotrione and tembotrion) in microorganism; and the mutant PaHPPD-SDM led to a tolerance of up to 60 μM against three triketone herbicides (sulcotrione, mesotrione and tembotrion) in microorganism.

At the same time, using the plant constitutive 35S promoter, the gene PaHPPD-M3 was over-expressed and transformed into *Arabidopsis,* and an *Arabidopsis* plant overexpressing PaHPPD-M3 that significantly resistant to HPPD inhibitors (triketone herbicides) was obtained. At the level of ½MS medium, the maximum tolerance concentration of HPPD inhibitor before the germination of T3 generation seeds of *Arabidopsis* overexpressing PaHPPD-M3 was 125 nM. Under conditions of herbicide-containing medium, the maximum tolerance concentration of HPPD inhibitor of T3 generation transgenic seedlings was 250 nM. Under potted conditions, HPPD inhibitor (mesotrione) was sprayed on fully expanded leaves of well-grown *Arabidopsis,* and the maximum tolerance concentration was 5 μM.

After being treated with 250 nM triketone herbicides for 6 h, the total chlorophyll and carotenoid contents of the leaves of *Arabidopsis* plants overexpressing PaHPPD-M3 were significantly higher than those of WT, OE At and OE Pa. Compared with the seedlings without herbicide treatment, the expression of HPPD, VTE1 and VET3 genes in PaHPPD-M3 overexpressing lines were significantly up-regulated, while the expression of HPPD, VTE1 and VET3 genes in WT, OE At and OE Pa lines were significantly down-regulated.

The *Arabidopsis* plants overexpressing PaHPPD-M3 were cultured in ½ MS medium containing 100 nM mesotrione for 72 h. Then the newly expanded leaves were stained with NBT and DAB respectively. The results indicated that the accumulation of superoxide and hydrogen peroxide in *Arabidopsis* plants overexpressing PaHPPD-M3 was significantly less than that in WT, OE At and OE Pa.

At the same time, the gene PaHPPD-SDM was overexpressed and cloned into 35S-pCAMBIA1305-3FLAG vector, which was transferred into rice Nipponbare through rice transgene technology mediated by *Agrobacterium* to obtain the transgenic rice T0 generation strain. Transgenic rice in pots was sprayed with herbicide (200 μM mesotrione) on well-grown seedlings. 21 days after the treatment, the leaves of wild-type rice were albino and the growth was inhibited until death, while OE PaHPPD-SDM rice grew well and the phenotype was similar to that of untreated OE PaHPPD-SDM. The chlorophyll content of OE PaHPPD-SDM leaves after treatment did not decrease significantly.

Under normal growth conditions (treated with 0.1% Tween-20 as control), the contents of superoxide, hydrogen peroxide ($H_2O_2$) and malondialdehyde (MDA) in leaves of WT and OE SDM rice lines were similar. 1 week after spraying with 200 μM mesotrione (prepared with 0.1% Tween-20), the contents of superoxide, $H_2O_2$ and MDA in WT rice leaves were significantly higher than that in OE SDM rice leaves. It showed that the overexpression of PaHPPD-SDM in OE SDM rice prevented the accumulation of peroxide, $H_2O_2$ and MDA, and enhanced the resistance to triketone herbicides.

Using the plant constitutive 35S promoter, the genes PaHPPD-Gm and PaHPPD-SDM were overexpressed and cloned into 35S-pCAMBIA1305-3FLAG vector, which were transferred into soybean William 82 through soybean transgenic technology mediated by *Agrobacterium* to obtain transgenic soybean T0 and T1 generation strains. The leaves were coated with different concentrations of mesotrione (0, 1, 5, 10 and 30 μM, prepared with 0.1% Tween-20). 2 weeks later, the leaves of the OE PaHPPD-SDM soybean line did not show symptoms of bleaching or damage at a mesotrione concentration of 30 μM, while WT showed bleaching symptoms at a mesotrione concentration of 5 μM, and the bleaching symptoms became more severe as the concentration increased.

4 week-old seedlings of T1 generation soybean line of OE PaHPPD-SDM, T1 generation soybean of OE GmHPPD and WT were sprayed twice with 20 μM mesotrione. 2 weeks after the treatment, it was found that the contents of chlorophyll a and chlorophyll b in the leaves and the plant height of OE GmHPPD and WT sprayed with mesotrione were significantly lower than that of the control treatment, and the performance of WT was more significant. At the same time, it was found that the contents of chlorophyll a and chlorophyll b in the leaves and the plant height of OE PaHPPD-SDM sprayed with mesotrione were reduced compared with the control, but the contents of chlorophyll a and chlorophyll b and the plant height were both significant higher than that of OE GmHPPD and WT treated with mesotrione. It was shown that OE PaHPPD-SDM soybean significantly improved its resistance to triketone herbicides.

Therefore, the present invention relates to nucleic acid sequences encoding mutant PaHPPD-M1-7, PaHPPD-DS18, PaHPPD-DS73 and PaHPPD-SDM, mutation sites and amino acid sequences thereof, as well as PaHPPD-SDM rice lines and seeds and PaHPPD-SDM soybean strains and seeds. Further provided are methods for imparting herbicide-resistance or tolerance to plants, particularly resistance or tolerance to certain classes of HPPD inhibitory herbicides through PaHPPD-M3 and PaHPPD-SDM. The mutant gene will play an important role in the application of obtaining plants tolerant to HPPD inhibitory herbicides.

Terms

As used herein, the term "HPPD" refers to 4-Hydroxyphenylpyruvate Dioxygenase (HPPD, EC 1.13.11.27) existing in various organisms and it is a key enzyme that catalyzes the oxygenation of 4-hydroxyphenylpyruvate (HPP, the degradation product of tyrosine) to produce homogentisate (HGA). Inhibition of HPPD will lead to uncoupling of photosynthesis in plant cells and lack of auxiliary light-harvesting pigments. At the same time, due to the lack of photoprotection normally provided by carotenoids, reactive oxygen intermediates and photooxidation cause chlorophyll destruction, resulting in albinism in the photosynthetic tissues of plants, and the growth is inhibited until death. HPPD inhibitory herbicides have proved to be very effective selective herbicides with spectral herbicidal activity, which can be used both before and after buds, with high activity, low residues, safety for mammals and environmental friendliness, etc.

As used herein, the terms "HPPD inhibitor", "HPPD inhibitory herbicide", and "HPPD inhibiting herbicide" are used interchangeably, and refer to a preparation that inhibits plant growth or even causes plant death by inhibiting HPPD, preferably are triketone HPPD inhibitors, such as sulcotrione, mesotrione, and tembotrion.

As used herein, the terms "herbicide-resistance polypeptide", "mutated HPPD polypeptide", "mutated PaHPPD polypeptide", "mutated HPPD protein", "mutated HPPD enzyme", "polypeptide of the invention" are used interchangeably, and all refer to the polypeptide of the first aspect of the invention.

In another preferred embodiment, the herbicide-resistance polypeptide is a protein or polypeptide having SEQ ID NO:

4, SEQ ID NO: 6, SEQ ID NO: 8 and/or SEQ ID NO: 10, or a derived polypeptide or active fragment thereof having the same herbicide tolerance.

As used herein, the terms "herbicide-resistance" and "herbicide tolerance" are used interchangeably and refer to tolerance to herbicides, especially triketone HPPD inhibitors, such as sulcotrione, mesotrione, tembotrion. The herbicide-resistance polypeptides PaHPPD-M3, PaHPPD-DS18 and PaHPPD-DS73 of the present invention can tolerate herbicides with a concentration of at least 10 μM, preferably 50 μM, more preferably 100 μM. The herbicide-resistance polypeptide PaHPPD-SDM of the present invention can tolerate herbicides with a concentration of at least 10 μM, preferably 40 μM, more preferably 60 μM. In addition, the rice seedlings overexpressing the herbicide-resistance polypeptide PaHPPD-SDM of the present invention can tolerate herbicides with a concentration of at least 200 μM, preferably 400 μM, more preferably 600 μM. At the same time, the soybean seedlings overexpressing the herbicide-resistance polypeptide PaHPPD-SDM of the present invention can tolerate herbicides with a concentration of at least 40 μM, preferably 80 μM, more preferably 120 μM.

As used herein, "isolation" refers to the material is isolated from its original environment (if it is a natural substance, the original environment is the natural environment). Such as, the polynucleotides and polypeptides in the native state of the living cells are not isolated and purified, but the same polynucleotides or polypeptides are isolated from other substances present in the natural state, then they are isolated and purified.

As used herein, "isolated herbicide-resistance polypeptide" refers that the herbicide-resistance polypeptide is basically free of other proteins, lipids, carbohydrates or other substances that are naturally associated with it. The skilled in the art can purify herbicide-resistance polypeptide using standard protein purification techniques. Substantially pure polypeptides can produce a single primary band on non-reductive polyacrylamide gels.

The Polypeptide(s) of the Present Invention

The herbicide resistant polypeptide of the present invention has one or more characteristics selected from the group consisting of:

(a) the polypeptide constitutes HPPD protease in the form of homotetramer in bacteria such as *Pseudomonas;*
(b) the polypeptide forms HPPD protease in the form of homodimer in plants and mammals;
(c) the primary structures of the polypeptides PaHPPD-M3, PaHPPD-DS18, PaHPPD-DS73 and PaHPPD-SDM can be divided into two structural regions, including the significantly different N-terminal region and the highly conserved C-terminal region;
(d) the polypeptides PaHPPD-M3, PaHPPD-DS18, PaHPPD-DS73 and PaHPPD-SDM all have an α/β folding structure, the core of which is composed of parallel and anti-parallel β chains and surrounded by a helix, the structure contains a tubbiness domain. The iron binding site and the AA surrounding the active site are unchanged. The mutation site (R282S) is located on the α-helix. One (A156V) of the three mutation sites is located on the connection between the α-helix and β. The other two are located on two adjacent α-helices. One of the mutations on the position of the α-helix (E349K) may affect the structure of this α-helix, and the helix acts as an entrance for the substrate to enter the active center. The mutation of another mutation site (R282S) will greatly affect the opening and closing of the entrance for the substrate to enter the active center, resulting in a larger entrance.

Figure 10:
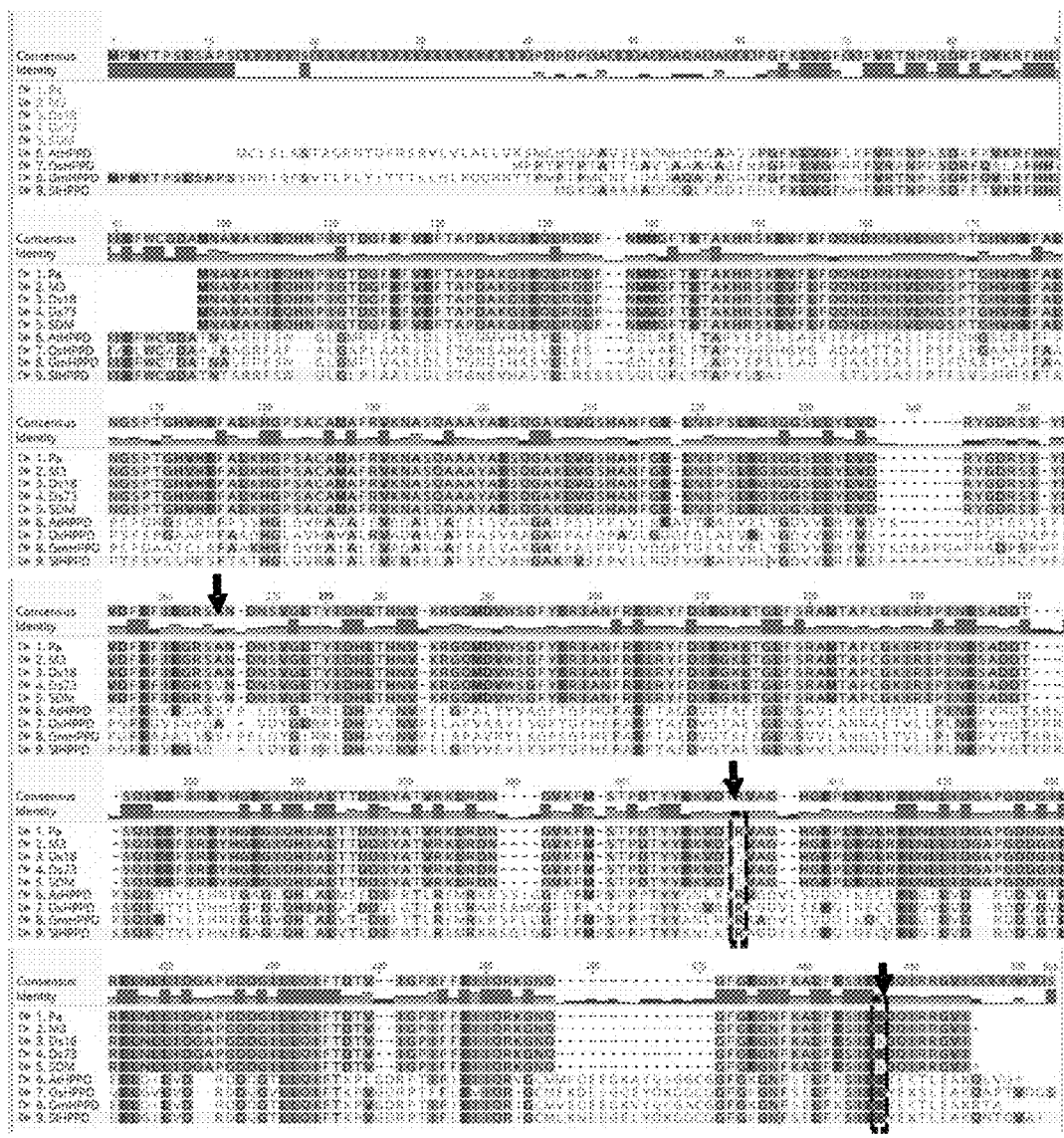
FIG. 10 shows the amino acid sequence alignment of PaHPPD and mutants thereof (PaHPPD-M3, PaHPPD-DS18, PaHPPD-DS73, and PaHPPD-SDM) and plant HPPDs. Wherein, the abbreviations have the following meanings: AtHPPD-HPPD of *Arabidopsis thaliana;* GmHPPD-HPPD of soybean; OsHPPD-HPPD of rice; S1HPPD-HPPD of tomato; PaHPPD-HPPD of *Pseudomonas aeruginosa.* Note: The sites marked by black arrow and black box are conserved sites in plant HPPDs, wherein the arginine at position 282 in the PaHPPD amino acid sequence is mutated to serine (R282S) and the glutamic acid at position 349 is mutated to lysine (E349K).

The amino acid sequence alignment results of PaHPPD derived from *Pseudomonas aeruginosa* and its mutants PaHPPD-M3, PaHPPD-DS18, PaHPPD-DS73 and PaHPPD-SDM with plant HPPDs are shown in FIG. 10, wherein the bold black arrows indicate the conserved sites between different HPPDs that mutated. It can be seen that the positions 282 and 349 in PaHPPD amino acid sequence are conservative in *Arabidopsis* (corresponding positions are 349 and 433), rice (corresponding positions are 346 and 430), soybean (corresponding positions are 395 and 479) and tomato (corresponding positions are 341 and 425); the position 156 in PaHPPD amino acid sequence is conservative in rice (corresponding position is 213). The mutation at position 282 from R to S (i.e. PaHPPD-M3 mutant); the mutation at position 282 from R to S and the mutation at position 349 from E to K (i.e. PaHPPD-DS18 mutant); the mutation at position 282 from R to S and the mutation at position 156 from A to V (i.e. PaHPPD-DS73 mutant); the mutation at position 282 from R to S, the mutation at position 349 from E to K and the mutation at position 156 from A to V (i.e. PaHPPD-SDM mutant), have a crucial role in herbicide-resistance in crops.

Figure 25:
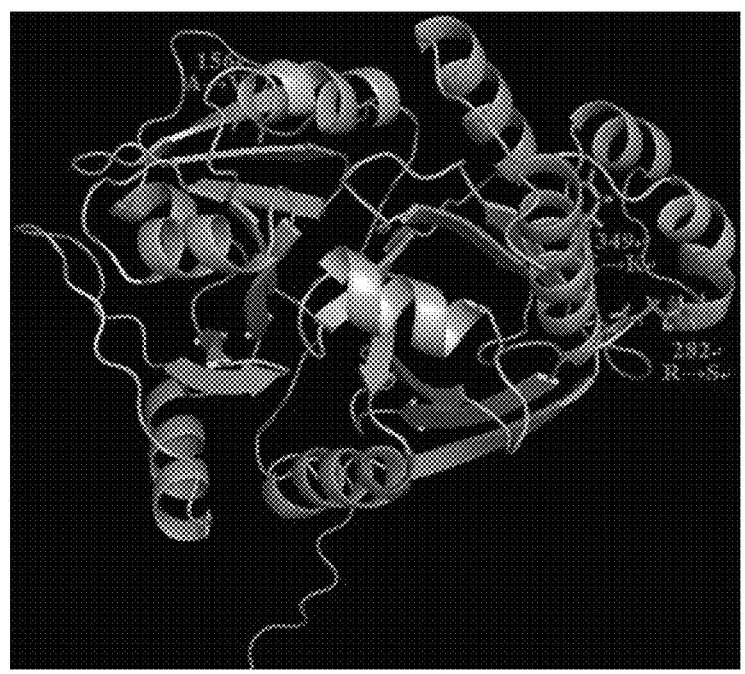
FIG. 25 shows the three-dimensional protein structure of P. aeruginosa PaHPPD labeled with mutation sites of PaHPPD-M3, PaHPPD-DS18, PaHPPD-DS73 and PaHPPD-SDM.
Figure 26:
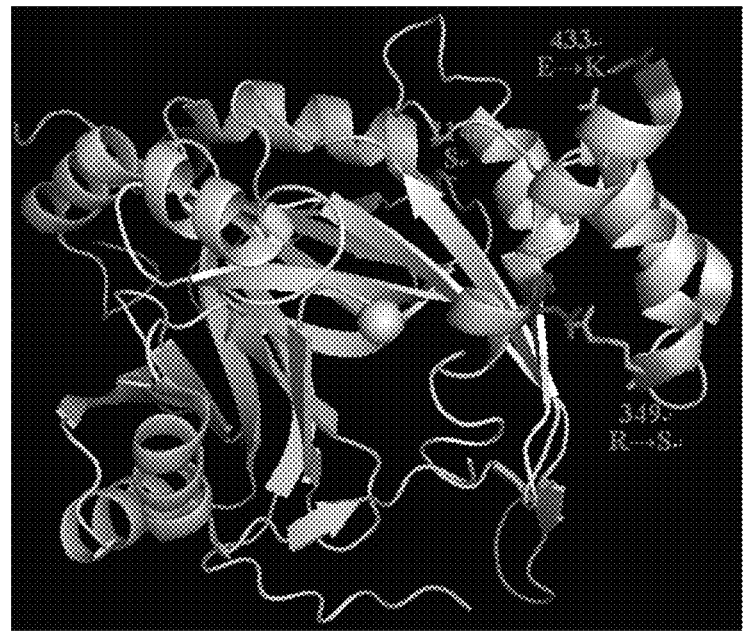
FIG. 26 shows the three-dimensional protein structure of Arabidopsis AtHPPD labeled with mutation sites of PaHPPD-M3, PaHPPD-DS18, PaHPPD-DS73 and PaHPPD-SDM.
Figure 27:
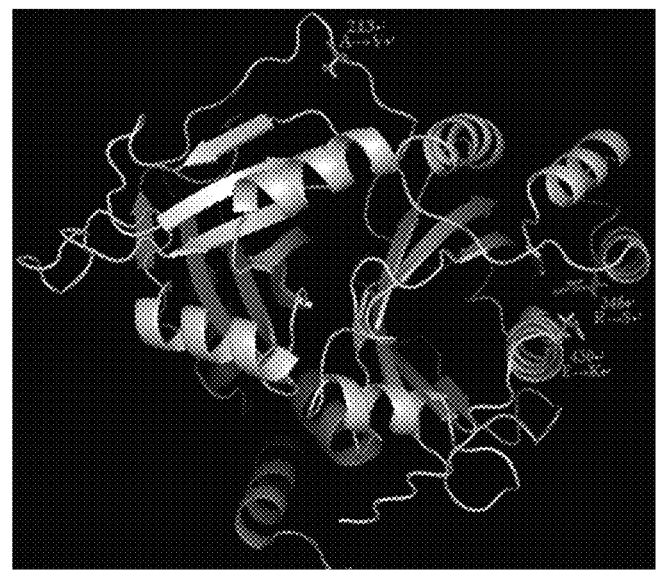
FIG. 27 shows the three-dimensional protein structure of rice OsHPPD labeled with mutation sites of PaHPPD-M3, PaHPPD-DS18, PaHPPD-DS73 and PaHPPD-SDM.
Figure 28:
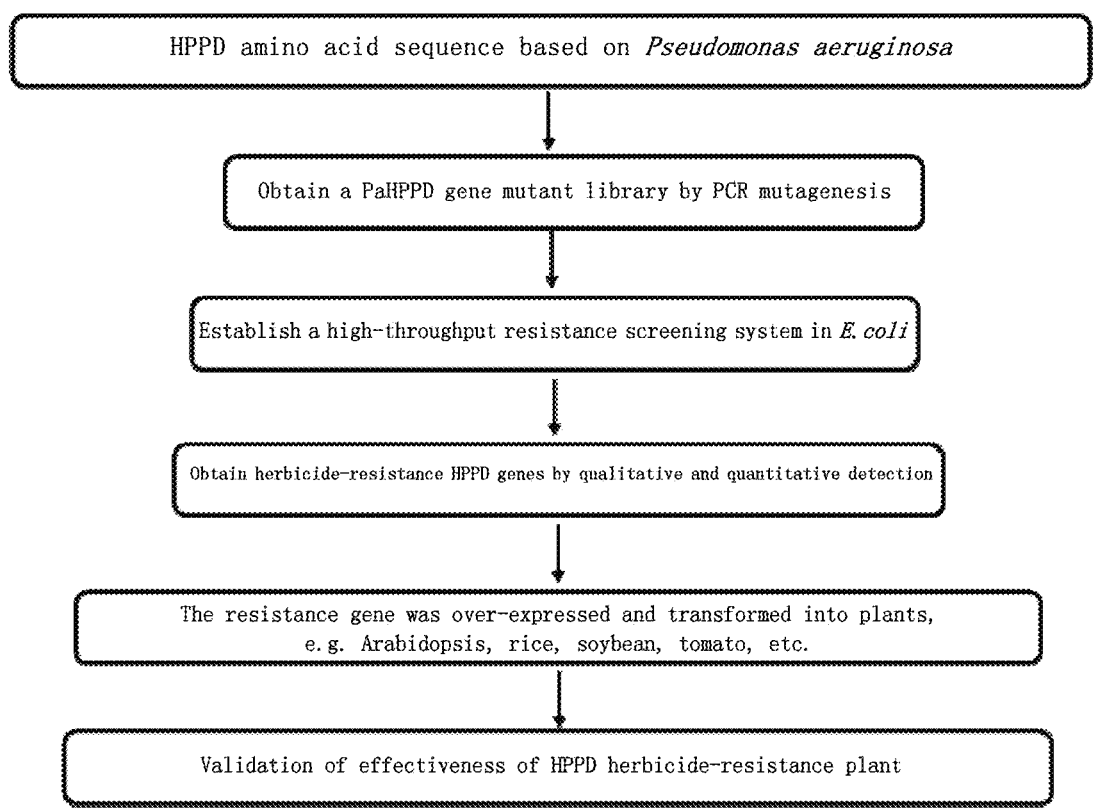
FIG. 28 shows the experimental process of the present invention. The invention obtained a PaHPPD gene mutant library by PCR mutagenesis based on HPPD amino acid sequence of Pseudomonas aeruginosa. Then a high-throughput resistance screening system is established in E.coli. At the same time, herbicide-resistance HPPD gene was obtained by qualitative and quantitative detection. Then the resistance gene was over-expressed and transformed into plants (e.g. Arabidopsis, rice, soybean, tomato, etc.). Finally, the effectiveness of HPPD herbicide-resistance plant was verified.

The three-dimensional HPPD protein structure of *P. aeruginosa, Arabidopsis* and rice marked with mutation sites of PaHPPD-M3, PaHPPD-DS18, PaHPPD-DS73 and PaHPPD-SDM are shown in FIGS. 25, 26 and 27, respectively. It can be seen that two of the mutation sites are on two different α helices in the HPPD structures of *Pseudomonas aeruginosa, Arabidopsis* and rice, and one of the mutation sites (E349K) forms a salt bond with the amino acid on the α helix it located, which may cause the change of this α helix and affect the structure of this alpha helix, and this alpha helix serves as an entrance for the substrate to enter the active center. The other mutation site (R282S) forms a salt bond with the opposite amino acid. After the mutation, the chain length becomes shorter, and the opposite amino acid is pulled to swing outward, which results in a larger entrance for the substrate to enter the active center.

The nucleotide and amino acid information of the main species HPPD is shown in Table A below

TABLE A

| Name | Species derived | Accession number of amino acid sequence | Gene ID/ Gene symbol |
| --- | --- | --- | --- |
| PaHPPD | *Pseudomonas aeruginosa* | NP_249556 | 882225 |
| AtHPPD | *Arabidopsis thaliana* | 6532701544 | AT1G06570.1 |
| OsHPPD | Rice | XP_015626163 | Os02g0168100 or LOC4328425 |
| GmHPPD | Soybean | NP_001235148 | LOC100101901 |
| SlHPPD | tomato | XP_004243609 | LOC101245475 |

The polypeptide(s) of the present invention may be recombinant polypeptide(s), natural polypeptide(s), synthetic polypeptide(s), and preferably recombinant polypeptide(s). The polypeptide(s) of the present invention may be naturally purified products, or chemically synthesized products, or produced from prokaryotic or eukaryotic hosts (e.g., bacteria, yeasts, higher plants, insects and mammalian cells) using recombinant techniques. The polypeptide(s) of the present invention may be glycosylated or may be non-glycosylated according to the host used in the recombinant production protocol. The polypeptide(s) of the invention may also include or may not include the starting methionine residue.

The present invention further includes the fragments, derivatives and analogs of the herbicide-resistance polypeptide. As used herein, the terms "fragments", "derivatives" and "analogs" refer to the polypeptides basically maintaining the same biological function or activity of the natural herbicide-resistance polypeptide of the present invention. The polypeptide fragments, derivatives or analogs of the present invention may be (i) a polypeptide with one or more conservative or non-conservative amino acid residues (preferably the conservative amino acid residues) being substituted, while such substituted amino acid residues may or may not be encoded by genetic code, or (ii) a polypeptide having substituted group(s) in one or more amino acid residues, or (iii) a polypeptide formed by fusion of the matured polypeptide with another compound (such as the compound that prolongs the half-life of the polypeptide, such as polyethylene glycol), or (iv) a polypeptide formed with additional amino acid sequence fused to said polypeptide sequence (such as, leader sequence, secretion sequence, or a sequence or a protein sequence used to purify the polypeptide, or a fusion protein). According to the subject application, these fragments, derivatives and analogs are within the scope commonly known by the skilled person.

In the present invention, the term "herbicide-resistance polypeptide" refers to a polypeptide having the sequence of SEQ ID NO: 4 and the tolerance of herbicides. The term also includes a variant form of SEQ ID NO: 4 having the same function as the herbicide-resistance polypeptide. These variant forms include, but are not limited to, deletions of one or more amino acids (typically 1-50, preferably 1-30, more preferably 1-20, most preferably 1-10), insert ions and/or substitutions, and the addition of one or several amino acids (typically at most 20, preferably at most 10, more preferably at most 5) at the C-terminus and/or N-terminus. For example, in the art, the protein's functions are usually unchanged when an amino acids is substituted by a similar or analogous one. Also, for example, the addition of one or several amino acids at the C-terminus and/or the N-terminus will not normally alter the function of the protein. The term also includes active fragments and active derivatives of the herbicide-resistance polypeptide.

The variant forms of the polypeptide include homologous sequences, conserved variants, allelic variants, natural mutants, induced mutants, protein encoded by a DNA capable of hybridizing to the DNA of herbicide-resistance polypeptide under high or low stringency conditions, and a polypeptide or protein obtained using an antiserum against the herbicide-resistance polypeptide. The present invention further provides other polypeptides, such as fusion proteins comprising the herbicide-resistance polypeptide or fragments thereof. In addition to the almost full length of the polypeptide, the present invention also includes a soluble fragment of the herbicide-resistance polypeptide. Typically, the fragment has at least about 10 contiguous amino acids of the herbicide-resistance polypeptide, typically at least about 30 contiguous amino acids, preferably at least about 50 contiguous amino acids, more preferably at least about 80 contiguous amino acids, most preferably at least about 100 contiguous amino acids.

The invention also provides the analogues of the herbicide-resistance polypeptide or the polypeptide. These analogues can differ from the herbicide-resistance polypeptide by amino acid sequence differences or by modifications that do not affect the sequence, or by both. These polypeptides include natural or induced genetic variants. Induced variants can be obtained by various techniques, such as random mutagenesis by irradiation or exposure to a mutagenic agent, but also by site-directed mutagenesis or other known molecular biology techniques. Also included are analogues which include residues other than those naturally occurring L-amino acids (e.g., D-amino acids) or non-naturally occurring or synthetic amino acids (e.g., β or γ-amino acids). It is to be understood that, the polypeptides of the present invention is not limited to the representative polypeptides listed hereinabove.

Modification (usually do not change the primary structure) includes in vivo or in vitro chemical derivation of polypeptides, e.g., acelylation, or carboxylation. Also included is modification of glycosylation. Also included are sequences that have phosphorylated amino acid residues, e.g., phosphotyrosine, phosphoserine, phosphothronine, as well as sequences that have been modified to improve their resistance to proteolytic degradation or to optimize solubility properties.

In the present invention, "conservative variant polypeptide of the herbicide-resistance polypeptide" refers to a polypeptide formed by replacing at most 10, preferably at most 8, more preferably at most 5, most preferably 3 amino acids with the amino acid having similar or analogous property, compared with the amino acid sequence of SEQ ID NO: 4. These conservative variant polypeptides are preferably formed by carrying out the amino acid replacement according to Table B.

Preferably, the polypeptide of the present invention (including a conservative variant polypeptide, or a derivative polypeptide) maintains the mutation from arginine (R) to serine (S) or threonine (T) at the amino acid of position 282 corresponding to SEQ ID NO: 2. More preferably, the polypeptide of the present invention maintains the mutation from arginine (R) to serine (S) at the amino acid of position 282 corresponding to SEQ ID NO: 2.

TABLE B

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Polynucleotides

The polynucleotides of the present invention can be in a form of DNA or RNA. DNA forms include cDNA, genomic DNA, or synthetic DNA. DNA can be single-stranded or double-stranded. DNA can be the coding strand or the non-coding strand. The coding sequences encoding mature polypeptide can be identical to the coding sequences shown in SEQ ID NO: 3, SEQ ID NO: 5, SEQ ID NO: 7 and SEQ ID NO: 9 or can be degenerate variants thereof.

As used herein, "degenerate variants" in the present invention refers to nucleic acid sequences encoding proteins having SEQ ID NO: 4, SEQ ID NO: 6, SEQ ID NO: 8 and SEQ ID NO: 10 but different from the coding sequences shown in SEQ ID NO: 3, SEQ ID NO: 5, SEQ ID NO: 7 and SEQ ID NO: 9.

The polynucleotides encoding the mature polypeptides of SEQ ID NO: 4, SEQ ID NO: 6, SEQ ID NO: 8 and SEQ ID NO: 10 comprise coding sequences encoding only the mature polypeptide; coding sequences of the mature polypeptide and various additional coding sequences; coding sequences (and optionally additional coding sequences) of the mature polypeptide, and non-coding sequences.

The term "polynucleotide encoding a polypeptide" may include a polynucleotide that encodes the polypeptide, or a polynucleotide that also includes additional coding and/or non-coding sequences.

The present invention also relates to variants of the polynucleotides as described above, which encode fragments, analogs and derivatives of polypeptides or polypeptides having the same amino acid sequence as the present invention. Variants of such polynucleotides may be naturally occurring allelic variants or non-naturally occurring variants. Such nucleotide variants include substitutions of variants, deletions of variants, and insertions of variants. As is known in the art, an allelic variant is an alternative form of a polynucleotide, which may be a substitution, deletion or insertion of one or more nucleotides, but the function of the polypeptide encoded by the polynucleotide will not be substantially altered.

The present invention also relates to polynucleotides that hybridize to the sequences as described above and having at least 50%, preferably at least 70%, more preferably at least 80% identical between the two sequences. In particular, the present invention relates to polynucleotides that can hybridize to the polynucleotides of the present invention under stringent conditions. In the present invention, "stringent conditions" mean: (1) hybridization and elution at lower ionic strength and higher temperature, such as 0.2×SSC, 0.1% SDS, 60° C.; or (2) hybridization adding a denaturant, such as 50% (v/v) formamide, 0.1% calf serum/0.1% Ficoll, 42° C., or the like; or (3) hybridization only occurs when the identity between the two sequences is at least 90%, more preferably 95% or more. And the polypeptide encoded by the hybridizable polynucleotide has the same biological function and activity as the mature polypeptide shown in SEQ ID NO: 4.

The present invention also relates to a nucleic acid fragment that hybridizes to the above sequences. As used herein, "a nucleic acid fragment" is at least 15 nucleotides in length, preferably at least 30 nucleotides, more preferably at least 50 nucleotides, and most preferably at least 100 nucleotides. Nucleic acid fragments can be used for nucleic acid amplification techniques (such as PCR) to determine and/or isolate polynucleotides encoding the herbicide-resistance polypeptide.

Recombinant Technology and Plant Improvement

A polynucleotide full length sequence or fragment thereof encoding the herbicide-resistance polypeptide of the present invention can be obtained via PCR amplification, recombinant method or artificial synthesis. For a PCR amplification method, primers can be designed according to the relevant nucleotide sequences disclosed in the present invention, particularly the open reading frame sequences, and the commercially available cDNA libraries or cDNA libraries prepared by the conventional methods known to the skilled in the art were used as a template, and amplified and the relevant sequences were obtained. When the sequence is longer, two or more PCR amplifications are usually needed, and then each of the amplified fragments are spliced together in the correct order.

Once the relevant sequence is obtained, the relevant sequence can be obtained in bulk using a recombination method. Usually cloned into a vector, then transferred into a cell, and then the relevant sequence is separated and obtained from the proliferation of host cells by the conventional method.

In addition, the relevant sequence can also be synthesized using artificial synthesis methods, particularly when the fragment is shorter. In general, a very long fragment can be obtained by firstly synthesizing multiple small fragments and then ligating them.

At present, a DNA sequence encoding the protein of the present invention (or fragments thereof, or derivatives thereof) can completely be obtained by chemical synthesis. The DNA sequence can then be introduced into a variety of existing DNA molecules (or vectors) and cells known in the art. In addition, mutations can also be introduced into the protein sequences of the present invention by chemical synthesis.

The present invention also relates to a vector containing a polynucleotide of the present invention, and a host cell produced by genetic engineering using the vector or the herbicide-resistance polypeptide encoding sequence of the present invention, and a method for producing the polypeptide of the present invention by recombinant techniques.

With the conventional recombinant DNA technique (Science, 1984; 224: 1431), the polynucleotide of the present invention can be used to express or produce the recombinant herbicide-resistance polypeptide. Generally, the method comprises the following steps:

(1) transforming or transfecting a suitable host cell with a polynucleotide or variant thereof encoding the herbicide-resistance polypeptide of the present invention or a recombinant expression vector containing said polynucleotide;
(2) culturing the host cell in a suitable culture medium;
(3) isolating and purifying protein from the culture medium or cell.

The polynucleotide sequence of the present invention can be inserted into a recombinant expression vector. The term "a recombinant expression vector" refers to bacterial plasmids, phages, yeast plasmids, plant cell viruses, mammalian cell viruses or other vectors well known in the art. In a word, any plasmid and vector can be used as long as it can be replicated and stabilized in the host. An important feature of an expression vector is that it usually contains a replication origin, a promoter, a marker gene, and a translation control element.

An expression vector containing an encoding DNA sequence of herbicide-resistance polypeptide and a suitable transcription/translation control signal can be constructed by the methods well known to the skilled in the art. These methods comprise DNA recombinant technology in vitro, DNA synthesis technology, recombinant technology in vivo, and the like. The DNA sequence can be operably linked to an appropriate promoter in an expression vector to direct mRNA synthesis. The expression vector also comprises a ribosome binding site for translation initiation and a transcription terminator.

In addition, the expression vector preferably comprises one or more selectable marker genes to provide the selection of phenotypic traits for the transformed host cells, such as dihydrofolate reductase for eukaryotic cell culture, neomycin resistance, and green fluorescent protein (GFP), or tetracycline or ampicillin resistance for E. coli.

A vector comprising an appropriate DNA sequence and a suitable promoter or a control sequence as described above can be used to transform an appropriate host cell to enable it to express the protein.

A host cell can be a prokaryotic cell, such as a bacterial cell; or a lower eukaryotic cell, such as a yeast cell; or a higher eukaryotic cell, such as a plant cell (such as a cell of crop and forestry plant). Representative examples are: Escherichia coli, Streptomyces, Agrobacterium; a fungal cell such as yeast; a plant cell, an animal cell and the like.

When the polynucleotides of the present invention are expressed in a higher eukaryotic cell, the transcription will be enhanced if an enhancer sequence is inserted into a vector. The enhancer is a cis-acting factor of DNA, usually about 10 to 300 base pairs, acting on the promoter to enhance the transcription of the gene.

It will be apparent to the ordinary skilled in the art how to select an appropriate vector, promoter, enhancer and host cell.

Transformation of host cells with recombinant DNA can be carried out using conventional techniques well known to the skilled in the art. When the host is a prokaryote such as E. coli, competent cells capable of absorbing DNA can be harvested after the exponential growth phase and treated with $CaCl_2$, the steps used are well known in the art. Another method is to use $MgCl_2$. If necessary, the transformation can also be carried out by means of electroporation. When the host is a eukaryote, the following DNA transfection methods can be used: calcium phosphate coprecipitation method, conventional mechanical method, such as micro-injection, electroporation, liposome packaging, etc.

Agrobacterium or gene gun transformation method, such as leaf discs, can be used to transform a plant. For the transformed plant cell, tissue or organ, the conventional method can be used to regenerate a plant, thereby obtaining plants resistant to herbicide changes.

Gene editing technology can also be used to directly edit the HPPD in the genome of the target plant, so that the plant cells express the herbicide-resistance polypeptide of the present invention. Representative gene editing techniques include CRISPR gene editing system, error-prone PCR, genetic recombination, TALEN and ZFN.

The CRISPR/Cas (clustered regularly interspaced short palindromic repeats/CRISPR-associated proteins) system is an acquired immune system that resists the invasion of exogenous viruses or plasmid DNA in bacteria and archaea. The nuclease of this system recognizes and degrades exogenous DNA under the guidance of crRNA. Wherein the type II CRISPR/Cas system is simple in composition, including only one nuclease Cas9 and tracrRNA: crRNA dimer to complete the recognition and cleavage functions. The CRISPR/Cas9 system has rapidly become a new generation of genome editing technology due to its advantages of easy design and manipulation, high editing efficiency and wide versatility. It has been widely used in humans, mice, rats, zebrafish, caenorhabditis elegans, plants, fungus and bacteria.

The obtained transformants can be cultured by a conventional method to express a polypeptide encoded by a gene of the present invention. According to the host cell used, the medium used in the culture may be selected from a variety of conventional media. And the host cell can be cultured under conditions suitable for the growth of the host cell. After the host cell has grown to an appropriate cell density, the selected promoter is induced by a suitable method (such as temperature conversion or chemical induction) and the cells are cultured for a further period of time.

The recombinant polypeptide in the method above may be included in the cells, or expressed on the cell membrane, or secreted out of the cell. If desired, the physical, chemical and other properties can be utilized in various isolation methods to isolate and purify the recombinant protein. These methods are well-known to those skilled in the art. The examples of these methods include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combination thereof.

T recombinant herbicide-resistance polypeptide has uses in many aspects. For example, it can be used in screening compounds, polypeptides or other ligands that promote or antagonize the function of herbicide-resistance polypeptide. The expressed recombinant herbicide-resistance polypeptide can be used in screening valuable polypeptide molecules that can stimulate the function of herbicide-resistance polypeptide in a polypeptide library.

In another aspect, the present invention further comprises a polyclonal antibody and a monoclonal antibody, especially a monoclonal antibody having specificity to the herbicide-resistance polypeptide of the present invention or the coding gene thereof. The present invention includes not only intact monoclonal or polyclonal antibodies, but also antibody fragments with immunological activity, or chimeric antibodies.

The antibodies of the present invention may be prepared by various techniques known to the skilled in the art. For example, a purified herbicide-resistance polypeptide gene product or an antigenic fragment thereof can be administered to an animal to induce the production of a polyclonal antibody. Various antibodies of the present invention can be obtained by conventional immunization techniques using fragments or functional regions of the herbicide-resistance polypeptide gene product. These fragments or functional regions can be prepared using recombinant methods or synthesized using peptide synthesizers. An antibody that binds to an unmodified form of a herbicide-resistance polypeptide gene product can be produced by immunizing an animal with a gene product produced in a prokaryotic cell (e.g., E. coli); an antibody that binds to a post-translational modified form (such as a glycosylated or phosphorylated protein or polypeptide) can be obtained by immunizing an animal with a gene product produced in eukaryotic cells (e.g., a yeast or insect cell). Anti-herbicide-resistance polypeptide antibodies can be used to detect the herbicide-resistance polypeptide in a sample.

A method for detecting the presence of herbicide-resistance polypeptide in a sample is to detect using a specific antibody against herbicide-resistance polypeptide, comprising: contacting the sample with the specific antibody against herbicide-resistance polypeptide; and observing the formation of an antibody complex; the formation of the antibody complex indicates that the presence of herbicide-resistance polypeptide in the sample.

A portion or all of the polynucleotides of the present invention may be immobilized on a microarray or DNA chip (also referred to as a "gene chip") as a probe for the analysis of differential expression analysis of genes in a tissue. The specific primers of herbicide-resistance polypeptide are used for in vitro amplification of RNA-polymerase chain reaction (RT-PCR), which can also detect the transcription product of herbicide-resistance polypeptide.

In a preferred embodiment, the invention obtained a PaHPPD gene mutant library by PCR mutagenesis based on HPPD amino acid sequence of *Pseudomonas aeruginosa*. Then a high-throughput resistance screening system is established in *E.coli*. At the same time, herbicide-resistance HPPD gene was obtained by qualitative and quantitative detection. Then the resistance gene was over-expressed and transformed into plants (e.g. *Arabidopsis*, rice, soybean, tomato, etc.). Finally, the effectiveness of HPPD herbicide-resistance plant was verified.

Sequence Listing Information

The information of the sequence listing involved in this application is shown in Table C below, and the mutations involved are shown in Table D and Table E below.

TABLE C

| SEQ ID NO: 1 | Nucleic acid sequence encoding *Pseudomonas aeruginosa* HPPD (PaHPPD) |
| --- | --- |
| SEQ ID NO: 2 | Amino acid sequence of *Pseudomonas aeruginosa* HPPD (PaHPPD) |
| SEQ ID NO: 3 | Nucleic acid sequence encoding the mutant M3 of *Pseudomonas aeruginosa* HPPD (PaHPPD-M3) in first round error-prone PCR |
| SEQ ID NO: 4 | Amino acid sequence of the mutant M3 of *Pseudomonas aeruginosa* HPPD (PaHPPD-M3) in first round error-prone PCR |
| SEQ ID NO: 5 | Nucleic acid sequence encoding the HPPD mutant PaHPPD-DS18 of *Pseudomonas aeruginosa* |
| SEQ ID NO: 6 | Amino acid sequence of the HPPD mutant PaHPPD-DS18 of *Pseudomonas aeruginosa* |
| SEQ ID NO: 7 | Nucleic acid sequence encoding the HPPD mutant PaHPPD-DS73 of *Pseudomonas aeruginosa* |
| SEQ ID NO: 8 | Amino acid sequence of the HPPD mutant PaHPPD-DS73 of *Pseudomonas aeruginosa* |
| SEQ ID NO: 9 | Nucleic acid sequence encoding the HPPD mutant PaHPPD-SDM of *Pseudomonas aeruginosa* |
| SEQ ID NO: 10 | Amino acid sequence of the HPPD mutant PaHPPD-SDM of *Pseudomonas aeruginosa* |

Based on the wild-type *Pseudomonas aeruginosa* HPPD gene, through random mutagenesis of PaHPPD performed by error-prone PCR, the application screened and obtained M3 (PaHPPD-M3) mutant wherein the amino acid at position 282 was mutated from arginine to serine.

Subsequently, based on the M3 mutant, through a first round of DNA shuffling of PaHPPD-M3, DS18 mutant was obtained wherein the amino acid at position 282 was mutated from arginine to serine and the amino acid at position 349 was mutated from glutamic acid to lysine.

Subsequently, based on the M3 mutant, a second round of DNA shuffling was performed, and PaHPPD-DS73 mutant was screened and obtained wherein the amino acid at position 282 was mutated from arginine to serine and the amino acid at position 156 was mutated from alanine to valine.

Finally, the three mutants of M3, DS18 and DS73 were combined by site-directed mutation to obtain PaHPPD-SDM mutant wherein the amino acid at position 282 was mutated from arginine to serine, the amino acid at position 349 was mutated from glutamic acid to lysine and the amino acid at position 156 was mutated from alanine to valine.

TABLE D

| Original gene | Representative mutant of PaHPPD obtained by random mutation | Base substitution | Amino acid substitution |
| --- | --- | --- | --- |
| PaHPPD | M1 | G772T | V258L |
| | M2 | G386C | G129A |
| | M3 | C844A | R282S |
| | M4 | G422A, C621T | R141H |
| | M5 | C165T, A463T | S155C |
| | M6 | G396A | No amino acid changes |
| | M7 | C234A, C465T, A790G | N264D |

TABLE E

| method | Mutant | Base substitution | Amino acid substitution |
| --- | --- | --- | --- |
| Error-prone PCR (ep-PCR) | M3 | C844A | R282S |
| First round of DNA shuffling (DNA shuffling round I, based on M3) | DS18 | C844A G216A G1045A | R282S E349K |
| Second round of DNA shuffling (DNA shuffling round II, based on M3) | DS73 | C844A C467T | R282S A156V |
| Site-directed mutation (Site-directed mutagenesis, based on DS18) | SDM | C844A G216A G1045A C467T | R282S E349K A156V |

The main advantages of the present invention are:
(a) The herbicide-resistance polypeptide of the present invention has obvious herbicide tolerance, and can tolerate herbicides with a concentration of at least 100 μM.
(b) By introducing the gene encoding the herbicide-resistance polypeptide, the resistance or tolerance of *Arabidopsis* to herbicides can be enhanced.
(c) By introducing the gene PaHPPD-SDM encoding the herbicide-resistance polypeptide of the present invention, the resistance or tolerance of rice to herbicides can be enhanced, and the rice seedlings overexpressing the herbicide-resistance polypeptide can tolerate herbicides with a concentration of at least 200 μM.
(d) By introducing the gene PaHPPD-SDM encoding the herbicide-resistance polypeptide of the present invention, the resistance or tolerance of soybean to herbicides can be enhanced, and the soybean seedlings overexpressing the herbicide-resistance polypeptide can tolerate herbicides with a concentration of at least 40 μM.
(e) The herbicide-resistant polypeptide of the present invention can be used to cultivate new varieties of herbicide-tolerant plants.

The present invention will be further illustrated below with reference to the specific examples. It is to be understood that these examples are for illustrative purposes only and are not intended to limit the scope of the invention. The experimental methods with no specific conditions described in the following examples are generally performed under the conventional conditions, or according to the manufacturer's instructions. Percentages and parts are by weight unless otherwise stated.

Commonly Used Materials and Methods

The enzyme substrate tyrosine and chemical reagents (such as mesotrione, tembotrion, and sulcotrione) used in the present invention were purchased from Sigma (Mainland China); T4 DNA ligase DNase I, restriction enzyme DpnI and T4 polynucleotide kinase were purchased from New England Biolabs (USA); KOD-Plus Neo DNA polymerase was purchased from Toyo (Japan). Bacterial genomic DNA extraction kit was purchased from Beijing Biotech Biotechnology Co., Ltd. (China). The Gene Morphology II Random Mutagenesis Kit for ep-PCR was purchased from Agilent Technologies (USA). The Ultra-fast New Plant RNA Extraction Kit was purchased from Beijing Huayueyang Biotechnology Co., Ltd. (China). The oligonucleotide primers used (Table 1) and sequencing services were provided by Shanghai Jieli Biotechnology Co., Ltd. (Shanghai, China).

Note: methanol was used to prepare a stock solution of 100 μM HPPD inhibitors (mesotrione, tembotrion and sulcotrione). Antibiotics (ampicillin/carbenicillin) and HPPD inhibitors (mesotrione, tembotrion and sulcotrione) were added together to the sterilized and cooled LBT medium to the required final concentration.

Isolation and Cloning of HPPD Gene from *Pseudomonas aeruginosa*

The PaHPPD gene from the genomic DNA of *Pseudomonas aeruginosa* was amplified using primers GEXPaHPPD F and GEXPaHPPD R (Table 1). The conditions of polymerase chain reaction (PCR) were as follows:

| Pre-denaturation 94° C. 5 min | |
|---|---|
| Denaturation 98° C. 10 sec | |
| Annealing 60° C. 30 sec | |
| Extension 68° C. 45 sec | 34 cycles |
| Final extension 72° C. 5 min | |

TABLE 1

PCR primers used in the present invention

| S. No | Primer name | Primer sequence | SEQ ID NO. |
|---|---|---|---|
| 1 | GXPaHPPD F | 5'TATGGATCCATGAACGCCGTGGCCAAGATC3' | SEQ ID NO: 11 |
|   | GXPaHPPD R | 5'TCGCGGCCGCTCAGATCACGCCGCGGCGAAT3' | SEQ ID NO: 12 |
| 2 | GEXAtHPPD F | 5'TATGGATCCTATGTGTCTATCGTTAGCTTCTACAGCTC3' | SEQ ID NO: 13 |
|   | GEXAtHPPD R | 5'CTATCTCGAGGGTTCTTCTTCTTGTTCATCCCA3' | SEQ ID NO: 14 |
| 3 | GWAtHPPD F | 5'GGGACAAGTTTGTACAAAAAAGCAGGCTTCATGTGTCTATCGTTAGCTTCTACAG 3' | SEQ ID NO: 15 |
|   | GWAtHPPD R | 5'GGGACCACTTTGTACAAGAAAGCTGGGTCGGTTCTTCTTCTTGTTCATCCCA3' | SEQ ID NO: 16 |
| 4 | GWPaHPPD F | 5'GGGACAAGTTTGTACAAAAAAGCAGGCTTCATGAACGCCGTGGCCAAGATCGAAC 3' | SEQ ID NO: 17 |
|   | GWPaHPPD R | 5'GGGGACCACTTTGTACAAGAAAGCTGGGTCTCAGATCACGCCGCGGCGAAT3' | SEQ ID NO: 18 |
| 5 | SDM HPPD F | 5'GGCCGCAGCGtCAACGACAAC3' | SEQ ID NO: 19 |
|   | SDM HPPD R | 5'TTCGATGAACTCGAAGTCGACGTCATAG3' | SEQ ID NO: 20 |
| 6 | Os SDM F | 5'TTGTACAATGAACGCCGTGGCCAAGATC3' | SEQ ID NO: 21 |
|   | Os SDM R | 5'CTCAAGCTTGATCACGCCGCGGCGAATCTGGT3' | SEQ ID NO: 22 |
| 7 | GmHPPD F | 5'TCCTGCAGATGCCCATGTACACTCCATCACT3' | SEQ ID NO: 23 |
|   | GmHPPD R | 5'CTCAAGCTTCGCGGTTCTTTTAGCTTCCAAAG3' | SEQ ID NO: 24 |
| 8 | Gm SDM F | 5'TTGTACAATGAACGCCGTGGCCAAGATC3' | SEQ ID NO: 25 |
|   | Gm SDM R | 5'CTCAAGCTTGATCACGCCGCGGCGAATCTGGT3' | SEQ ID NO: 26 |

Strain, Plasmid, Medium Composition and Culture Conditions

The host strain *E. coli* DH5α used for mutant library construction and gene cloning is cultured at 37° C. in the Luria-Bertani medium (LB medium) containing ampicillin/carbenicillin (100 μg/mL L). Plasmid pGEX-6P-1 was used as a gene cloning vector.

Formula of LB medium (1 L)
Peptone 10 g
*E. coli* extract 5 g
NaCl 10 g
Formula of LBT (LB +0.1% tyrosine) medium (1 L)
20 mL of 5% tyrosine (prepared by adding 1N HCl) was added to the sterilized and cooled LB medium to obtain LBT medium containing a final concentration of 0.1% tyrosine. Then the pH was adjust with 1 N KOH.

The 1074 bp PCR amplification product was cloned into pGEX-6P-1 vector with BamHI and NotI, and then transformed into *E. coli* DH5α cells. The integrity of the construct was verified by sequencing.

In order to compare the HPPD activity of plants with the HPPD activity from *Pseudomonas aeruginosa* in the *E. coli* screening system, the inventors extracted total RNA of *Arabidopsis* (Col 0) seedlings, and amplified the coding sequence of AtHPPD by RT-PCR using cDNA as a template.

PCR reactions were performed using PCR primers GEX-AtHPPD F and GEXAtHPPD R (Table 1). PCR conditions were as follows:

| Pre-denaturation 94° C. 5 min | |
| Denaturation 98° C. 10 sec | |
| Annealing 61° C. 30 sec | |
| Extension 68° C. 1 min | 34 cycles |
| Final extension 72° C. 5 min | |

The 1438 bp PCR amplification product was cloned into pGEX-6P-1 vector with BamHI and XhoI, and then transformed into *E. coli* DH5α cells. The integrity of the construct was verified by sequencing.

Generation of HPPD Mutants and Screening for Herbicide-Resistance

Random Mutagenesis by Using Error-Prone PCR

Random mutagenesis of PaHPPD was performed by error-prone (ep) PCR using the Gene Morphology II Random Mutagenesis Kit, and the PaHPPD mutants generated by the first round of ep-PCR were combined and cloned into the pGEX-6P-1 vector, and transformed into *E. coli* DH5α competent cells. Then all putative mutants were cultured in 96-well plates containing LBT (LB+0.1% tyrosine) medium, and the HPPD activity was evaluated based on the shade of brown pigments produced by the mutants during tyrosine metabolism. Mutants was selected according to the shade of metabolite color for sequencing and subsequent analysis.

Analysis of HPPD Activity of *E. coil* Cells Based on Colorimetry

*E. coli* lacks HPPD and homogentisic acid metabolism pathway, thus it cannot mineralize phenylalanine and tyrosine. *E. coli* was used as a PaHPPD screening system of herbicide insensitive and/or herbicide-resistance, based on the differences in the ability to restore pigmentation in LBT (LB+0.1% tyrosine) medium containing different doses (0-100 μM) of HPPD inhibitors (sulcotrione, mesotrione and tembotrion). The PaHPPD mutants obtained by random mutation was cloned into *E. coli* cells together with wild-type PaHPPD and AtHPPD for comparation and screening.

The bacteria solution shaking cultured overnight at 37° C. was centrifuged, and 200 μL of supernatant was transferred to a sterile 96-well plate (microplate with high throughput characteristics) using a 200 μL pipette on an ultra-clean workbench. The pigment content was measured with a microtiter plate reader at a wavelength of 405 nm (OD405 nm), and the HPPD activity was evaluated according to the size of the OD value.

DNA Shuffling

Single mutated PaHPPD-M3 (PaHPPD-M3 mutant with one amino acid mutation site obtained by random mutation of PaHPPD) was subjected to DNA shuffling to produce mutants with significantly improved resistance to HPPD inhibitors. The PaHPPD-M3 mutant gene was amplified from the recombinant plasmid pGEX-6P-1-M3 using specific primers and then gel purified. Digesting 1 μg of DNA with DNase I into a 50-100 bp fragment was taken about 5 minutes. The DNA fragment was purified with 1.5% agarose gel electrophoresis and recombined by primer-free PCR. The primer-free PCR products were PCR amplified using specific primers GEXPaHPPD F and GEXPaHPPD R, and the PaHPPD-M3 gene was amplified to full length. After primer-free PCR and primer PCR, a group of full-length M3 gene mutants were obtained and digested with Bam HI and Not I enzymes. The isolated fragment was ligated into the prokaryotic expression vector pGEX-6P-1, and the resulting second-generation mutant library was transformed into *E. coli* for screening.

Then all putative mutants were cultured in the LBT (LB+0.1% tyrosine) medium on the microtiter plate to observe the activity of HPPD. According to the brown shade of the medium, the highly active HPPD clones were selected for sequencing and analysis. The resistance to herbicides of the mutants with new amino acid substitutions were detected with colorimetric assay. In the presence of HPPD inhibitors, the *E. coli* color screening system was used to detect the second-generation mutants produced by the first round of DNA shuffling. These mutants were identified by the ability to restore brown pigments under the conditions of increasing concentration range (0-100 μM) of HPPD inhibitors, to increase the stringency of screening. PaHPPD-DS18 mutant (mutant PaHPPD-M3 with 1 amino acid mutation site R282S was obtained by random mutation of PaHPPD, and then a first round of DNA shuffling was preformed based on PaHPPD-M3, and mutant PaHPPD-DS18 with 2 amino acid mutation sites R282S and E349K was obtained) was obtained by screening.

In order to generate more mutants with high resistance to HPPD inhibitors, after the first round of DNA shuffling, a second round of DNA shuffling was performed based on PaHPPD-M3. Through the second round of DNA shuffling, more HPPD mutants were generated. In the presence of HPPD inhibitors (sulcotrione, mesotrione and tembotrion) at a concentration of 100 μM, the HPPD mutant PaHPPD-DS73 with higher activity was screened according to the amount of brown pigmentation. The mutant (PaHPPD-DS73) selected in the second round of DNA shuffling were sequenced, and further analyzed and compared with the first-generation mutant (PaHPPD-M3) and the second-generation mutant (PaHPPD-DS18) by activity.

Generation of PaHPPD-SDM

In order to further improve the resistance of *E. coli* to herbicides, three mutants of PaHPPD-M3, PaHPPD-DS18 and PaHPPD-DS73 were combined by site-directed mutation. In order to combine all the mutations from the three mutants, reverse PCR amplification was performed using SDMHPPD-F and SDMHPPD-R as reverse PCR mutation primers (Table 1) and pGEX-6P-1-DS18 plasmid DNA as a template. After PCR, the PCR product was gel purified and the plasmid DNA was digested with DpnI. Then the self-ligation of PCR products was performed by the action of T4 polynucleotide kinase and T4 DNA ligase. The self-ligated PCR products were then transformed into *E. coli* cells. The obtained recombinant pGEX-6P-1 SDM was sequenced and analyzed. It contains all three amino acid substitutions from PaHPPD-M3, PaHPPD-DS18 and PaHPPD-DS73. Then the obtained PaHPPD-SDM mutant was compared with its parental mutants (PaHPPD-M3, PaHPPD-DS18, and PaHPPD-DS73) to understand their ability of brown pigmentation in the presence of triketone herbicides at different doses (0-60 μM). The calculation formula of HPPD activity (%) is as follows:

$$\text{HPPD activity}(\%) = (Am/Ac) \times 100$$

Wherein Am refers to the average value of the absorbance at a specific herbicide dose, and Ac refers to the average value of the absorbance without the herbicide.

PaHPPD Sequence Analysis of *Pseudomonas aeruginosa*

In order to study the evolutionary relationship between PaHPPD and HPPD homologues of dicotyledonous and monocotyledonous plants, Clustal W2 was used to preform amino acid sequence alignment between PaHPPD (Pa) and its mutant PaHPPD-SDM (SDM), and HPPDs of various plants (such as AtHPPD of *Arabidopsis,* GmHPPD of soybean, OsHPPD of rice, and S1HPPD of tomato) (FIG. 10).

Construction of Expression Vector and Transformation of Plant

Figure 11:
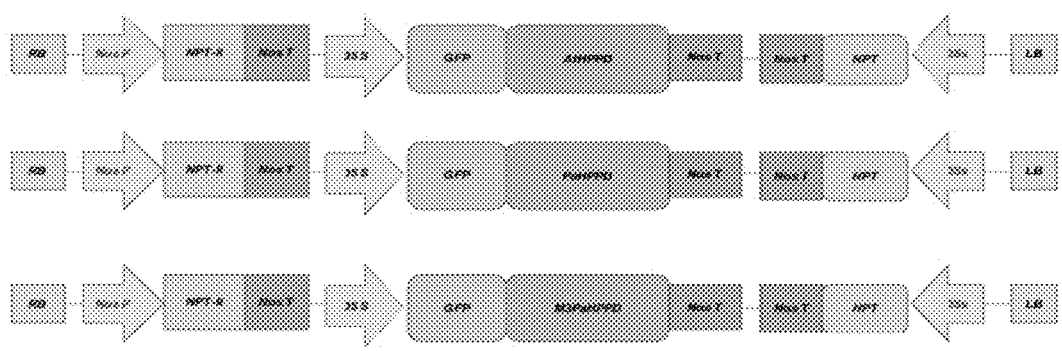
FIG. 11 shows the construction of pGWB6 (35S promoter, N-GFP) overexpression vector used for *Arabidopsis* transformation. Abbreviations: Nos-P: promoter sequence of nopaline synthase, Nos-T: terminator sequence of nopaline synthase, HPT (hygromycin phosphotransferase) gene is used as a selectable marker in plants, NPT-II (neomycin phosphotransferase II) gene is used as a selectable marker in bacteria and plants.

The expression vectors of AtHPPD, PaHPPD and its mutant PaHPPD-M3were constructed using the Gateway system binary vector pGWB6 (35S promoter, N-sGFP). The vectors were over-expressed and transformed into *Arabidopsis*. AtHPPD (OE At), PaHPPD (OE Pa) and PaHPPD-M3 (OE M3) overexpression *Arabidopsis* plants were obtained. The expression vector used for *Arabidopsis* transformation is shown in FIG. 11.

The 1438 bp full-length coding sequence of AtHPPD was cloned into pGWB6 vector (35S promoter, N-GFP) using primers GWAtHPPD F and GWAtHPPD R, and a 35Spro: AtHPPD (OE At) construct was generated. Constructs of 35Spro: PaHPPD (35S promoter, N-GFP) and 35Spro: M3PaHPPD (35S promoter, N-GFP) were generated by similar methods using primers GWPaHPPD F and GWPaHPPD R. All primers used for DNA construct generation are listed in Table 1. The above constructs were then transformed into *Agrobacterium tumefaciens* strain GV3101, and then transformed into *Arabidopsis* by floral-dip method. At the same time, the successfully transformed *Arabidopsis* strains were selected based on resistance to hygromycin. The homozygous T3 generation transgenosis *Arabidopsis* seedling was used for phenotypic and physiological analysis and molecular identification.

Figure 12:
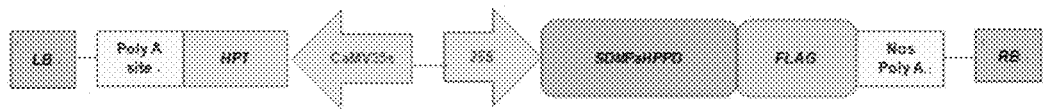
FIG. 12 shows the construction of 35S-pCAMBIA1305-3FLAG overexpression vector used for rice transformation. Wherein, the HPT (hygromycin phosphotransferase) gene is used as a selectable marker in plants, Poly A site: polyadenylation site, Nos Poly A: polyadenylation site of nopaline synthase.

Using OsSDM F and OsSDM R (Table 1) as PCR primers and using pGEX-6P-1-SDM plasmid as a template, SDM gene without termination codon was amplified and the fragment length thereof was 1074 bp. Using enzyme digestion and recombination method, the SDM gene was then integrated into the 35S-pCAMBIA1305-3FLAG vector (with two restriction sites of BsrG I and HindIII) to construct the 35S-pCAMBIA1305-SDMPaHPPD-3FLAG expression vector, which can express the SDMPaHPPD-3FLAG fusion protein (FIG. 12). Finally, the 35S-pCAMBIA1305-SDM-3FLAG (OE SDM) expression vector was transformed into *Agrobacterium tumefaciens* strain EHA105, and transformed into rice callus. The transgenic lines were first grown in a greenhouse (30° C. 16 h light/28° C. 8 h dark) for 1 month, and then transplanted into transgenic rice field (Shanghai, China, 30° N, 121° E). T0 generation transgenic rice seedling was used for phenotypic, physiological and molecular characterization analysis.

Figure 13:
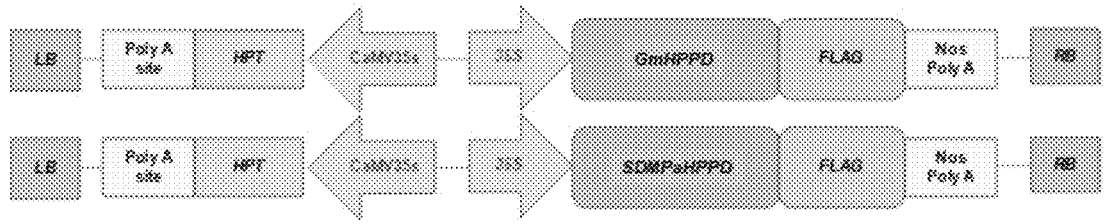
FIG. 13 shows the construction of 35S-pCAMBIA1305-3FLAG overexpression vector used for soybean (*Glycine max* cv. Williams 82) transformation. Wherein, the HPT (hygromycin phosphotransferase) gene is used as a selectable marker in plants, Poly A site: polyadenylation site, Nos Poly A: polyadenylation site of nopaline synthase.

Using PCR primers GmHPPD F and GmHPPD R (Table 1), the 1332bp full-length coding sequence of GmHPPD was cloned into the 35S-pCAMBIA1305-3FLAG vector (with two restriction sites of BsrGI and HindIII) to obtain 35S-pCAMBIA1305 -GmHPPD-3FLAG expression vector. The 35S-pCAMBIA1305-SDMPaHPPD-3FLAG expression vector was generated by similar method. Using GmSDM F and GmSDM R as primers and using pGEX-6P-1-SDM plasmid as a template, SDM gene without termination codon was obtained by PCR amplification and the fragment length thereof was 1074 bp. Using enzyme digestion and recombination method, the SDM gene was then integrated into the 355-pCAMBIA1305-3FLAG vector (with two restriction sites of BsrG I and HindIII) to construct the 35S-pCAMBIA1305-SDMPaHPPD-3FLAG expression vector, which can express the SDMPaHPPD-3FLAG fusion protein (FIG. 13). Finally, the expression vectors 35S-pCAMBIA1305-GmHPPD-3FLAG (OE Gm) and 35S-pCAMBIA1305-SDM-3FLAG (OE SDM) were transformed into *Agrobacterium tumefaciens* strain EHA105, respectively, and transformed into mature cotyledons of soybean (William 82). The inoculated materials were all placed in a culture room with a culture temperature of 23±1° C., a light temperature of 10000 lux, and a light length of 16 h to grow and differentiate. T0 and T1 generation transgenic soybean seedling was used for phenotypic, physiological and molecular characterization analysis.

Determination of oxidative Stress Indexes of *Arabidopsis* Treated with Herbicides Determination of Superoxide Content in Leaves of *Arabidopsis* by Nitroblue Tetrazolium (NBT) Staining Method 2 week-old *Arabidopsis* seedlings were cultured continuously in ½ MS mediums with 100 nM mesotrione and without mesotrione for 72 h, and then transferred to 3.5 mg/mL NBT staining solution (prepared with potassium phosphate buffer containing 10 mM $NaN_3$) and soaked in vacuum for 2 min, and then placed on a shaker overnight. The NBT-stained plants were placed in a mixed solution of acetic acid:glycerol:ethanol=1:1:3 (v/v/v) and destained at 100° C. for 5 min, then reserved in a mixed solution of glycerol:ethanol=1:4 (v/v), and was used to take photos to record the test results.

Determination of Hydrogen Peroxide Content in Leaves of *Arabidopsis* by 3,3-Diaminobenzidine (DAB) Staining Method $H_2O_2$ staining reagent-3,3-diaminobenzidine (3,3'-diaminobenzidine, DAB, D5637, Sigma-Aldrich) was dissolved in water and adjusted to pH 3.8 with KOH, which was the prepared 1.25 mg/mL DAB staining solution (prepared when it is in need to avoid oxidation).

2 week-old *Arabidopsis* seedlings were cultured continuously in ½ MS mediums with 100 nM mesotrione and without mesotrione for 72 h, and then transferred to DAB staining solution, and soaked in vacuum for 2 min, and then placed on a shaker for 7-8 hours. The DAB-stained plants were placed in a mixed solution of acetic acid:glycerol: ethanol=1:1:3 (v/v/v) and destained at 100° C. for 5 min, then reserved in a mixed solution of glycerol: ethanol=1:4 (v/v), and was used to take photos to record the test results.

Evaluation of Herbicide-Resistance of T0 Generation Rice 35S-pCAMBIA1305-SDM-3FLAG (OE-SDM) expression vector was used to evaluate the potential of SDM overexpressing line PaHPPD-SDM in rice, and then the tolerance responses of T0 generation line of OE SDM and wild type rice (WT) to herbicides were compared to evaluate the resistance of T0 generation plants to herbicides.

Analysis of Rice Resistance to Herbicides at Pot Level

Transgenic T0 generation OE SDM and WT rice seedlings were planted in pots containing soil and placed in an artificial climate room (30° C. 16 h light/28° C. 8 h dark) for growth. 3 weeks later, when the rice seedlings reached a height of 15-20 cm, 200 μM mesotrione (prepared with 0.1% Tween-20) and 0.1% Tween-20 were sprayed to OE SDM and WT rice seedlings, respectively. Then, the phenotype should be observed every week. The oxidative stress index was measured 1 week after the treatment, the chlorophyll content of the leaves was measured 2 weeks after the treatment, and the experimental result was photographed 3 weeks after the treatment.

Determination of Total Chlorophyll Content in Rice Leaves

Referring to the method of Lichtenthaler HK (1987), chlorophyll was extracted from the leaves of wild-type and T0 generation OE SDM rice seedlings which were sprayed with 200 μM mesotrione (prepared with 0.1% Tween-20) and sprayed with control 0.1% Tween-20 after 2 weeks and its content was determined. All experiments were repeated biologically 3 times, and the average value was taken.

Determination of Oxidative Stress Indexes of Rice Treated with Herbicides

Herbicides cause the production of reactive oxygen species (ROS), leading to cell death. In order to determine the oxidation state of rice, leaves of wild-type and T0-generation OE SDM rice which were sprayed with 200 μM mesotrione (prepared with 0.1% Tween-20) and sprayed with control 0.1% Tween-20 were collected, and stained with nitroblue tetrazolium (NBT) and 3,3-diaminobenzidine (DAB), respectively, to analyze the accumulation of superoxide ($O_2^-$) and hydrogen peroxide ($H_2O_2$).

Determination of Superoxide Content in Leaves of Rice by Nitroblue Tetrazolium (NBT) Staining Method At the end of the herbicide treatment, leaves of 4 week-old rice (normal growth for 3 weeks and herbicide spray treatment for 1 week) were placed in a 3.5 mg mL$^{-1}$ nitroblue tetrazolium (N6876, Sigma-Aldrich) staining solution (potassium phosphate buffer containing 10 mM NaN3), soaked in vacuum, and shaked on a shaker overnight. The NBT-stained plants were destained with a mixed solution of acetic acid:glycerol:ethanol=1:1:3 (v/v/v) at 100° C. for 5 min, and then reserved in a mixed solution of glycerol: ethanol=1:4 (v/v). The deposition of $O_2$ and NBT shows blue.

Determination of Hydrogen Peroxide Content in Leaves of Rice by 3,3-diaminobenzidine (DAB) Staining Method $H_2O_2$ staining reagent-3,3-diaminobenzidine (3,3'-diaminobenzidine, DAB, D5637, Sigma-Aldrich) was dissolved in water and adjusted to pH 3.8 with KOH to prepare 1.25 mg/mL DAB staining solution (prepared the staining solution when it is in need to avoid oxidation).

Rice seedling leaves were soaked in DAB staining solution for 2 min under vacuum, and then placed in a shaker for 7-8 h. The DAB-stained plants were destained with a mixed solution of acetic acid:glycerol:ethanol=1:1:3 (v/v/v) at 100° C. for 5 min, and then reserved in a mixed solution of glycerol:ethanol=1:4 (v/v). The polymerization of $H_2O_2$ and DAB shows brown.

Determination of Malondialdehyde Content in Rice Leaves

Malondialdehyde (MDA) is an important marker of the degree of oxide film damage. The previous method (Heath and Packer, 1968) for the determination of malondialdehyde content was referred with slight modifications. 1 g of rice leaves were accurately weighed and place to a pre-cooling mortar. 10 mL of pre-cooling 10% trichloroacetic acid (TCA, v/v) was added and grind thoroughly. Then the lapping solution was transfered to a 10 mL centrifuge tube and centrifuged at 4000 rpm for 10 min (4° C.). 2 mL of supernatant was pipetted and mixed with an equal volume of 0.6% 2-Thiobarbituric acid (TBA, v/v), and incubated at 100° C. for 15 min.

Then the reaction solution was cooled at room temperature. The cooled reaction solution was centrifuged at 4000 rpm for 10 min (4° C.). The supernatant was taken and measured absorbance at wavelengths of 450 nm, 532 nm and 600 nm using ultraviolet spectrophotometers, respectively. Each sample was repeated 3 times. The unit of MDA content is nmol g$^{-1}$ FW.

Analysis of Rice Resistance to Herbicides at Leave Level

Transgenic T0 generation OE SDMHPPD and WT soybean (William 82) seedlings were planted in pots and placed in an artificial climate room (27° C., 14 h/8 h, light/dark) for growth. After 4 weeks, 0, 1, 5, 10 and 30 μM of mesotrione (prepared with 0.1% Tween-20) and 0.1% Tween-20 were dipped with cotton swabs and evenly coated to the leaves of OE SDMHPPD (OE SDM #12 and OE SDM #13) T0 generation and WT seedlings having a height of 30-40 cm. Then, the phenotype was observed every week, and the experimental result was recorded by taking photos 2 weeks after the treatment.

To further test the resistance of transgenic soybeans to herbicides, 20 μM mesotrione (prepared with 0.1% Tween-20) and 0.1% Tween-20 were dipped with cotton swabs and evenly coated to the trifoliate leaves of 2 week-old WT, OE GmHPPD (OE GmHPPD #9) T1 generation seedlings and OE SDMHPPD (OE SDMHPPD #12) T1 generation. Then, the phenotype was observed every day, and the experimental result was recorded by taking photos 10 days after the treatment.

Analysis of Rice Resistance to Herbicides at Whole Plant Level

20 μM mesotrione (prepared with 0.1% Tween-20) and 0.1% Tween-20 were spray to 4 week-old transgenic T1 generation OE SDMHPPD, T1 generation OE GmHPPD and WT soybean which were grown in an artificial climate chamber (27° C., 14 h/8 h, light/dark) for the first time. A second spray was applied after 1 week. Then the phenotype of the plants was observed very day, and the experimental result was recorded by taking photos 2 weeks after the treatment.

Determination of Total Chlorophyll Content and Plant Height of T1 Generation Soybean Wild type soybean William 82, T1 generation OE PaHPPD-SDM soybean and T1 generation OE GmHPPD soybean seedlings were sprayed with 20 μM mesotrione (prepared with 0.1% Tween-20) and 0.1% Tween-20 for twice, respectively. The interval between two sprays is 1 week. Two weeks after spray treatment, the total chlorophyll of the leaves was extracted and the content was determined by referring to the method of Lichtenthaler HK (1987). All experiments were repeated biologically 3 times, and the average value was taken.

EXAMPLE 1

Generation of PaHPPD-M3 Mutant and Screening for Herbicide-Resistance 1.1 Random Mutation and Sequencing Using Error-Prone PCR By using error-prone PCR, several putative mutant colonies were obtained and cultured on LBT (LB+0.1% tyrosine) medium. The activity of HPPD was evaluated depending on their ability to produce brown pigment during tyrosine metabolism.

Only a few putative mutants can produce brown pigment on LBT medium, and then the putative mutants with HPPD activity were sequenced and analyzed. Sequencing analysis showed that the selected mutants had mutations at different nucleic acid sites (Table 2). Compared with the wild type PaHPPD, 6 (M1, M2, M3, M4, M5, M7) mutants showed new amino acid substitutions in their polypeptides, while M6 showed only base substitution G396A but no amino acid changes (FIG. 1).

TABLE 2

PaHPPD mutants obtained by random mutation (ep-PCR)

| method | Mutants | Base substitution | Amino acid substitution |
|---|---|---|---|
| Random Mutation (ep-PCR) | M1 | G772T | V258L |
| | M2 | G386C | G129A |
| | M3 | C844A | R282S |
| | M4 | G422A, C621T | R141H |
| | M5 | C165T, A463T | S155C |
| | M6 | G396A | No amino acid changes |
| | M7 | C234A, C465T, A790G | N264D |

Figure 2:
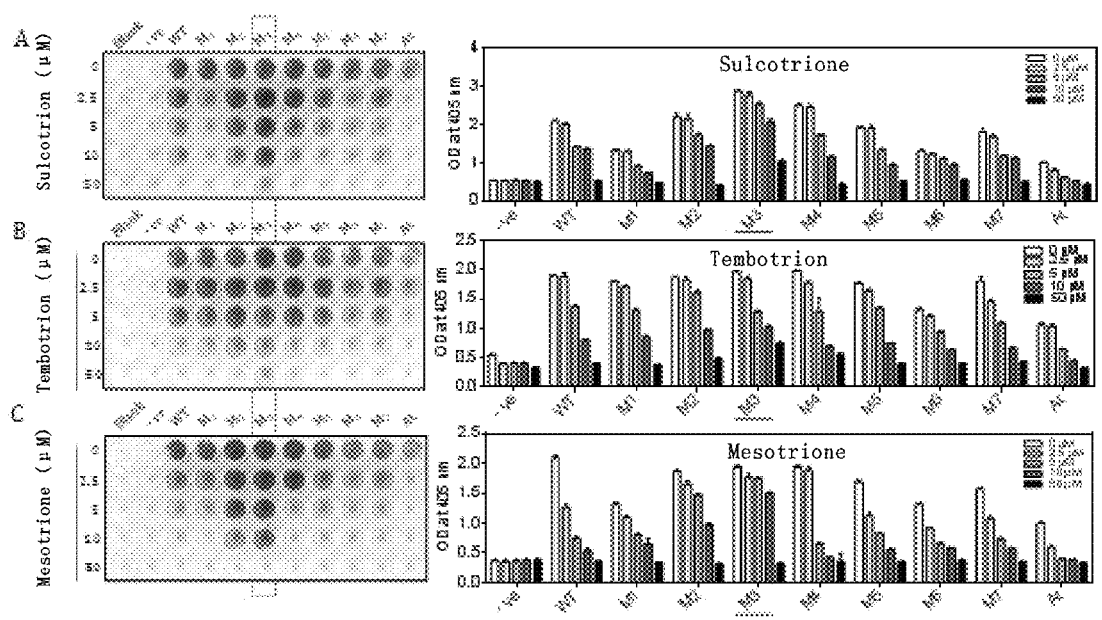
FIG. 2 shows the qualitative and quantitative (OD405 nm) analysis of the HPPD activity of wild-type (WT) PaHPPD, the first round ep-PCR mutant (M1 to M7) and AtHPPD(At) under the conditions of 0, 2.5, 5, 10 and 50 μM of three triketone herbicides (FIG. 2A sulcotrione, FIG. 2B tembotrion, FIG. 2C mesotrione).

1.2 Screening of Herbicide-Resistance Based on the *E. coli* Screening System Based on the *E. coli* screening system, the amount of melanin formed in the presence of different doses (0-50 μM) of triketone herbicides was determined at a wavelength of OD405 nm to analyze the activity of HPPD. As can be seen from FIGS. 2A, B, and C, in all selected *E. coli* HPPD clones (M1, M2, M3, M4, M5, M6, and M7) and *Arabidopsis* AtHPPD, compared with wild-type WT, M2 and M3 mutants had obvious resistance to three different herbicides (sulcotrione, tembotrion and mesotrione) (FIGS. 2 A, B and C).

Figure 3:
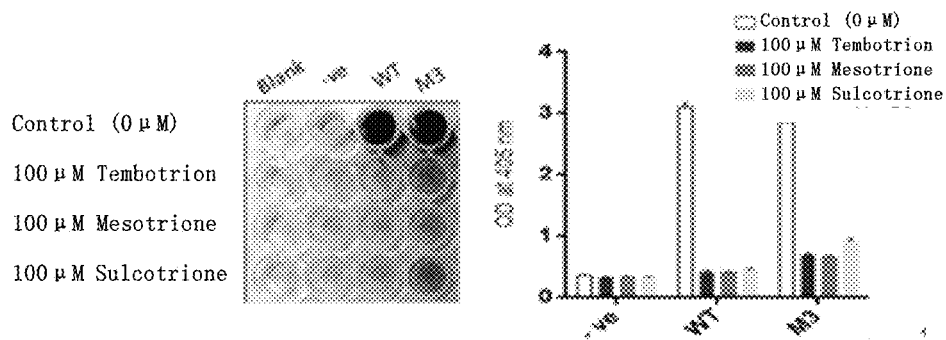
FIG. 3 shows the qualitative and quantitative (OD405 nm) analysis of the HPPD activity of WT (wild-type PaHPPD) and PaHPPD-M3 (first round ep-PCR mutant) under the conditions of 100 μM of three triketone herbicides (tembotrion, mesotrione, sulcotrione).

When the concentration of the herbicide was 10 μM or even higher, it can be seen that PaHPPD-M3 has shown stronger resistance to the triketone herbicide by measuring the amount of melanin formed. Based on this, the concentration of the herbicide was increased to 100 μM, and the mutant PaHPPD-M3 was significantly more resistant to the three different herbicides (sulcotrione, mesotrione and tembotrion) than the wild-type WT (FIG. 3). Compared with wild-type WT, the increased resistance of PaHPPD-M3 to herbicides may be due to the mutation of arginine (R) at position 282 in the amino acid sequence of PaHPPD to serine (S).

EXAMPLE 2

Generation of HPPD-DS18 Mutant and Screening for Herbicide-Resistance

The DNA shuffling system was used to shuffle the PaHPPD-M3 mutant obtained in Example 1 to produce more HPPD mutants. Several putative mutant colonies were obtained. Sequencing analysis of the second generation mutants (or Ds I mutants) with active HPPD revealed the mutation results (Table 3), respectively. It was found that all these mutants further had a unique base mutation or amino acid substitution in the PaHPPD-M3 mutant.

In the presence of triketone herbicides (sulcotrione, mesotrione and tembotrion), the HPPD activities of mutants with unique mutations or amino acid substitutions (DS7, DS8, DS18, DS23 and DS44) were compared with wild-type PaHPPD and first generation mutant PaHPPD-M3.

Figure 4:
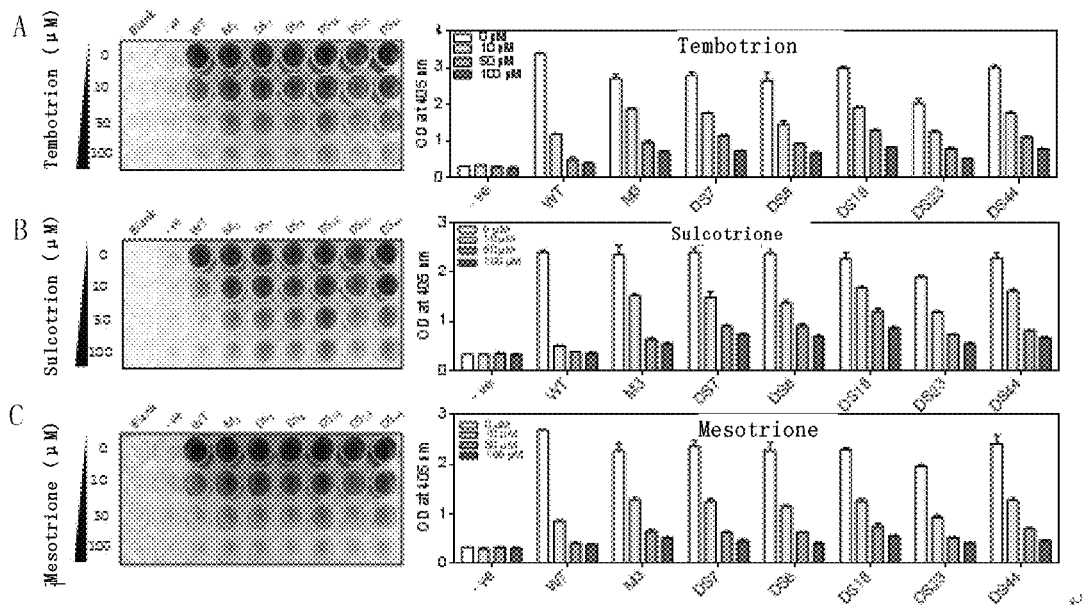
FIG. 4 shows the qualitative and quantitative (OD405 nm) analysis of the HPPD activity of wild-type (WT) PaHPPD, first round ep-PCR mutant (PaHPPD-M3) and first round DNA recombinant mutants (DS7, DS8, DS18, DS23 and DS44) under the conditions of 0, 10, 50 and 100 μM of three triketone herbicides (FIG. 4A tembotrion, FIG. 4B sulcotrione, FIG. 4C mesotrione).
Figure 5:
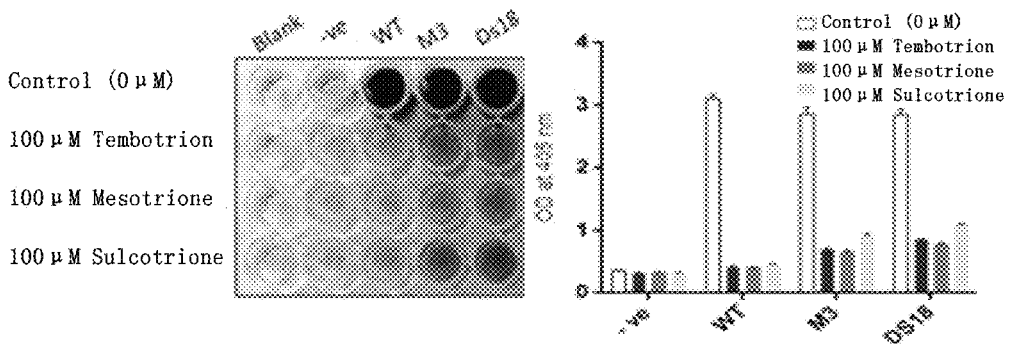
FIG. 5 shows the qualitative and quantitative (OD405 nm) analysis of the HPPD activity of wild-type (WT) PaHPPD, first round ep-PCR mutant (PaHPPD-M3) and first round DNA recombinant mutant (PaHPPD-DS18) under the conditions of 100 μM of three triketone herbicides (tembotrion, mesotrione, sulcotrione).

The results are shown in FIG. 4 and FIG. 5. All of the second generation mutants produced by the first round of DNA shuffling were compared with the first generation mutant (PaHPPD-M3), and the resistance of PaHPPD-DS18 to the three triketone herbicides (sulcotrione, mesotrione and tembotrion) were all higher than 100 μM. The mutant PaHPPD-DS18 has another amino acid substitution in the PaHPPD-M3 (PaHPPD mutant) sequence, that is, the E (glutamic acid) at position 349 is replaced by K (lysine) (Table 3).

TABLE 3

PaHPPD mutants obtained by DNA shuffling

| method | Mutants | Base substitution | Amino acid substitution |
|---|---|---|---|
| First round of DNA shuffling (DNA shuffling round I, based on M3) | DS7 | C844A | R282S |
| | | A238G | K80E |
| | DS8 | C844A | R282S |
| | | G1064C | G355A |
| | DS18 | C844A | R282S |
| | | G216A | No amino acid changes |
| | | G1045A | E349K |
| | DS23 | C844A | R282S |
| | | A758G | D253G |
| | Ds44 | C844A | R282S |
| | | C819T | No amino acid changes |

EXAMPLE 3

Generation of HPPD-DS73 Mutant and Screening for Herbicide-Resistance

Figure 6:
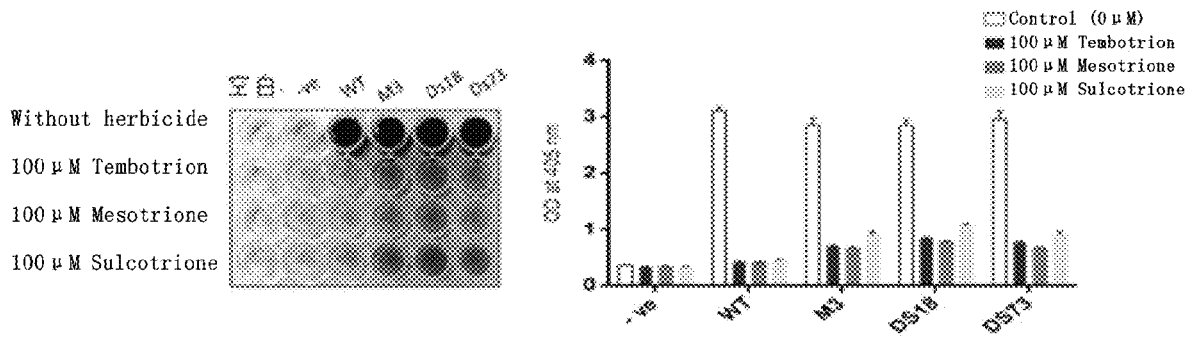
FIG. 6 shows the qualitative and quantitative (OD405 nm) analysis of the HPPD activity of WT (wild-type PaHPPD) and M3 (first round ep-PCR mutant PaHPPD-M3), DS18 (first round DNA recombinant mutant PaHPPD-DS18) and DS73 (second round DNA recombinant mutant PaHPPD-DS73) under the conditions of 100 μM of three triketone herbicides (tembotrion, sulcotrione, mesotrione).

The second round of DNA shuffling mutants (PaHPPD-DS73) having active HPPD were cloned and screened for their resistance to herbicides by the amount of pigmentation in the presence of 100 μM HPPD inhibitors (sulcotrione, mesotrione and tembotrion). It was observed that PaHPPD-DS73 showed (or retained) pigmentation in the LBT medium in the presence of 100 μM HPPD inhibitors (sulcotrione, mesotrione and tembotrion) (FIG. 6). Sequencing analysis showed that there was a conservative mutation of the PaHPPD-M3 mutant and another amino acid substitution in the PaHPPD-DS73 sequence, that is, the alanine at position 156 was replaced by valine (A156V) (Table E).

In the presence of 100 μM triketone herbicides (sulcotrione, mesotrione and tembotrion), the HPPD activities of WT, PaHPPD-M3, PaHPPD-DS18 and PaHPPD-DS73 were qualitatively and quantitatively analyzed at 405 nm. It was shown that the resistances of PaHPPD-M3, PaHPPD-DS18 and PaHPPD-DS73 to herbicide were significantly higher than that of WT. There is no significant difference between the three mutants, which are highly resistant to triketone herbicides (FIG. 6).

EXAMPLE 4

Generation of PaHPPD-SDM Mutant and HPPD Activity Comparison with Its Parental PaHPPD-M3 mutant with 1 amino acid mutation site (arginine at position 282 was mutated to serine) was obtained by random mutation of the gene (PaHPPD) from *Pseudomonas aeruginosa*. PaHPPD-DS18 mutant with 2 amino acid mutation sites (arginine at position 282 was mutated to serine and glutamic acid at position 349 was mutated to lysine) was obtained by the first round of DNA shuffling based on PaHPPD-M3. Then PaHPPD-DS73 mutant with 2 amino acid mutation sites (the alanine at position 156 was mutated to valine and the arginine at position 282 was mutated to serine) was obtained by the second round of DNA shuffling based on PaHPPD-M3 mutant. Finally, the three mutants of PaHPPD- M3, PaHPPD- DS18 and PaHPPD- DS73 were combined by site-directed mutation to form PaHPPD- SDM with three amino acid mutation sites (alanine at position 156 was mutated to valine, arginine at position 282 to was mutated serine, and glutamate at position 349 was mutated to lysine).

Figure 7:
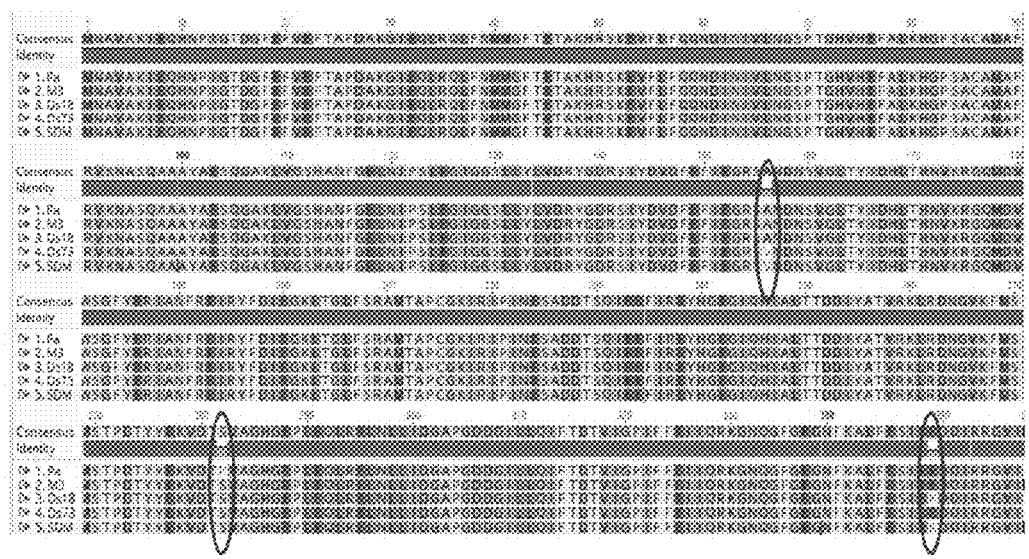
FIG. 7 shows the amino acid sequence alignment of WT (wild-type PaHPPD), M3 (first round ep-PCR mutant PaHPPD-M3), DS18 (first round DNA recombinant mutant PaHPPD-DS18) and DS73 (second round DNA recombinant mutant PaHPPD-DS73) and SDM (site-directed mutant PaHPPD-SDM).
Figure 8:
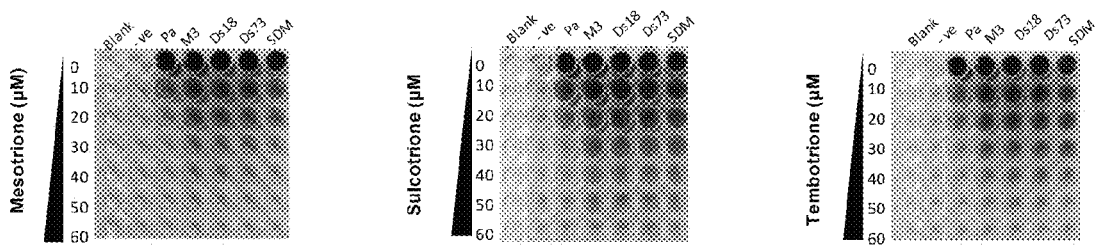
FIG. 8 and FIG. 9 show the qualitative and quantitative (OD405 nm) analysis of the HPPD activity of WT (wild-type PaHPPD) and M3 (first round ep-PCR mutant PaHPPD-M3), DS18 (first round DNA recombinant mutant PaHPPD-DS18), DS73 (second round DNA recombinant mutant PaHPPD-DS73) and SDM (site-directed mutant PaHPPD-SDM) under the conditions of 0-60 μM of three triketone herbicides (tembotrion, sulcotrione, and mesotrione).
Figure 9:
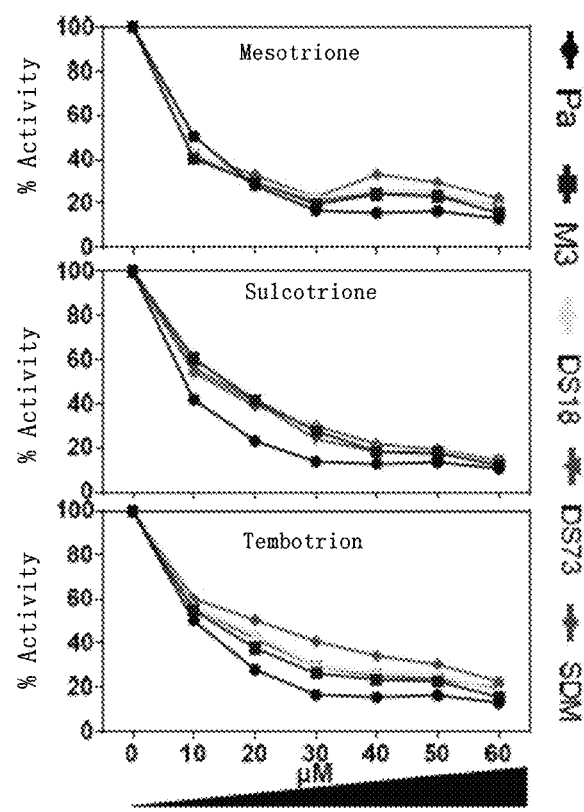

By amino acid sequence alignment of WT (PaHPPD), PaHPPD- M3, PaHPPD-DS18, PaHPPD-DS73 and PaHPPD-SDM, it was found that the sequence of PaHPPD-SDM comprised all of the amino acid mutations of PaHPPD-M3, PaHPPD-DS18 and PaHPPD-DS73 (FIG. 7 and Table E). At the same time, the HPPD activities (%) of PaHPPD- SDM with WT, PaHPPD- M3, PaHPPD- DS18 and PaHPPD- DS73 were compared, and it was found that PaHPPD-SDM improved the resistance to triketone herbicides (sulcotrione, mesotrione and tembotrion) in the presence of higher doses (in the range of 0~60 μIVI) of herbicide (especially tembotrion) (FIG. 8 and FIG. 9). It was shown that PaHPPD- SDM has stronger herbicide resistance than PaHPPD (WT) and three mutants PaHPPD- M3, PaHPPD-DS18 and PaHPPD-DS73.

EXAMPLE 5

Sequence Analysis of PaHPPD Gene Derived from *Pseudomonas aeruginosa*

The comparison and analysis of the amino acid sequences of PaHPPD (Pa), PaHPPD-SDM (SDM) and plant-derived HPPD genes-*Arabidopsis* (AtHPPD), soybean (GmHPPD), rice (OsHPPD) and tomato (S1HPPD) revealed that the two sites of amino acid substitutions (R282S and E349K) in PaHPPD are highly conserved in *Arabidopsis,* soybean, rice and tomato (FIG. 10). It is indicated that these two conserved sites can be used as target sites to create herbicide-resistance lines of rice, soybean, tomato and other crops using the CRISPR gene editing system.

EXAMPLE 6

Herbicide Resistance Analysis Before *Arabidopsis* Germination of Overexpression Line OE M3

In order to evaluate the resistance of different HPPD overexpression lines to herbicides, *Arabidopsis* seed germination tests were performed on media containing different concentrations of herbicides. T3 generation *Arabidopsis* seeds and Co10 (WT) seeds were performed steam surface sterilization (concentrated HCl: NaClO=1:5, v/v) for 3 h. Seeds of OE At (OE At #1, OE At #2), OE Pa (OE Pa #1, OE Pa #2), OE M3 (OE M3 #1, OE M3 #2) and Co10 (WT) were dibbled together in $^1/_2$ MS medium (0.5 x MS salt, 1% sucrose and 0.8% agar) in a 24-well plate, and the medium contained different concentrations (0, 31.25, 62.5, 125, 500 and 2000 nM) of mesotrione (Sigma Aldrich, USA) and sulcotrione (Sigma Aldrich, USA). Then, the plate dibbled seeds was placed in the dark at 4° C. for 3 d, and then transferred to a growth chamber at 22° C. (16 h light/8 h dark) for 2 weeks. Three biological replicates were performed per treatment per species. After 2 weeks, the test results were photographed.

Figure 14:
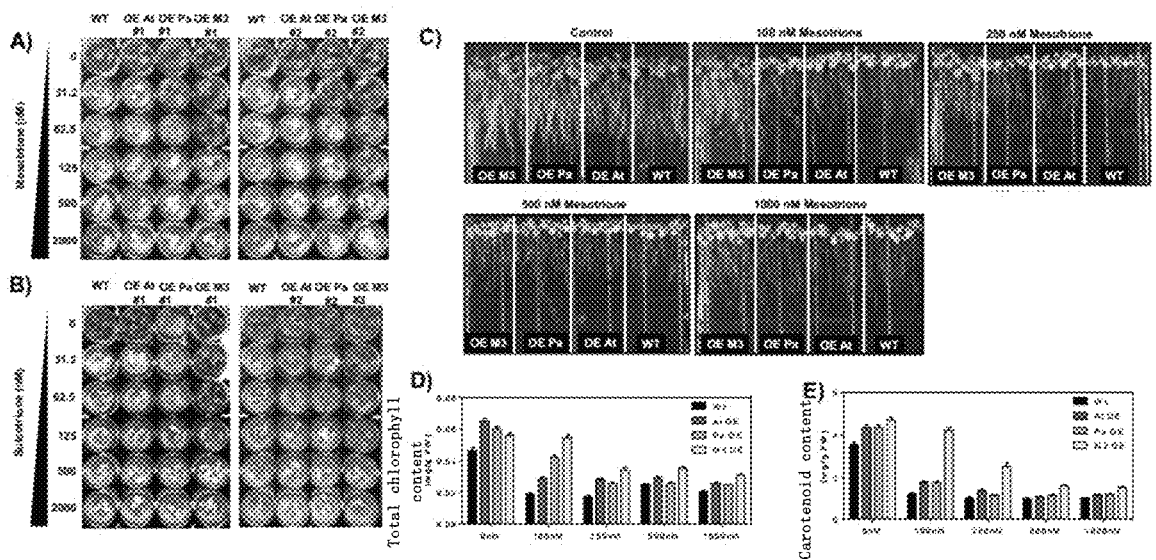

The results are shown in FIGS. 14A and 14B. Under normal growth conditions (0 nM herbicide), there is no difference in the seedlings phenotype of wild type (WT) and different lines of overexpression lines T3 generation (OE M3, OE Pa and OE At). After treatment with different concentrations of mesotrione, it was found that the two lines of OE M3 can still grow normally at a concentration up to 125 nM, and the two lines of OE Pa can grow normally at a concentration of 62.5 nM, while the two lines of OE At and WT have albino death at a lower concentration (31.25 nM) (FIG. 14A). After treatment with different concentrations of sulcotrione, it was found that the two lines of OE M3 can still grow normally at a concentration up to 125 nM, and the two lines of OE Pa can grow normally at a concentration of 62.5 nM, while the growth of OE At and WT was severely inhibited and even albinism died at a lower concentration (31.25 nM) (FIG. 14B). It is indicated that the overexpressing line OE PaHPPD-M3*Arabidopsis* line has obvious resistance to triketone herbicides before germination, and its resistance to herbicides is twice that of OE PaHPPD, and 4 times that of OE At and WT.

Example 7

Herbicide Resistance Analysis After *Arabidopsis* Germination of Overexpression Line OE M3

In order to further confirm the correctness of the results obtained in the germination test, an analysis experiment on herbicide resistance after *Arabidopsis* germination was conducted. *Arabidopsis* seedlings germinated by OE At, OE Pa, OE M3 and WT for 7 days were transferred to ½ MS medium containing different concentrations (0, 100, 250, 500, and 1000 nM) of mesotrione and grown for 1 week. 5 seedlings were treated per genotype with 3 biological replicates. After 1 week, the effect of the herbicide treatment (i.e., albino) was photographed.

The results are shown in FIG. 14C. There is no phenotypic difference between wild-type (WT), OE At, OE Pa and OE M3 Arabidopsis lines without herbicide treatment. After treatment with different concentrations of mesotrione, it was found that the cotyledons of WT were albino at 100 nM, and OE M3 grew well at 250 nM, while the cotyledons of other overexpression lines (OE At and OE Pa) were albino at this concentration. It is indicated that the OE PaHPPD-M3 *Arabidopsis* line has higher resistance to triketone herbicides after germination.

EXAMPLE 8

Content of Total Chlorophyll and Carotenoid of Overexpression Line OE M3 *Arabidopsis* Leaf (Rosette Leaf)

The leaves (rosette leaves) of 2 week-old plants grown in $^1/_2$ MS medium containing different concentrations (0, 100, 250, 500 and 1000 nM) of mesotrione were collected, including leaves of OE At, OE Pa, OE M3 and WT. The total chlorophyll and carotenoid were extracted and the content thereof was detected by referring to the method of Lichtenthaler HK (1987). All experiments were repeated biologically 3 times, and the average value was taken.

The results are shown in FIG. 14D. With the increase of herbicide concentration, the total chlorophyll and carotenoid content of WT, OE At, OE Pa and OE M3 *Arabidopsis* leaves (rosette leaves) were decreased. Wherein, under the same herbicide concentration, the total chlorophyll and carotenoid content of OE M3 were significantly higher than that of WT, OE At and OE Pa. It is indicated that OE PaHPPD-M3 line is more resistant to triketone herbicides than WT, OE At and OE Pa lines.

EXAMPLE 9

Herbicide Resistance Analysis of Overexpression Line OE M3 *Arabidopsis* at Pot Level 2 week-old *Arabidopsis* seedlings of WT, OE At, OE Pa, and OE M3 were transplanted into soil-filled pots (12 seedlings per pot) and growth in a phytotron (22° C., 14 h light/10 h dark, 120 μmol m$^{-2}$ s$^{-1}$ light intensity) for 4 weeks. Then, 5 μM mesotrione solution (prepared with 0.05% Tween-20) were sprayed twice with a treatment interval of 3 days, and compared with the control treatment (0.05% Tween-20 without herbicide). The spray treatment was biologically repeated 3 times. Two weeks after the first herbicide spray, the test results were photographed.

Figure 15:
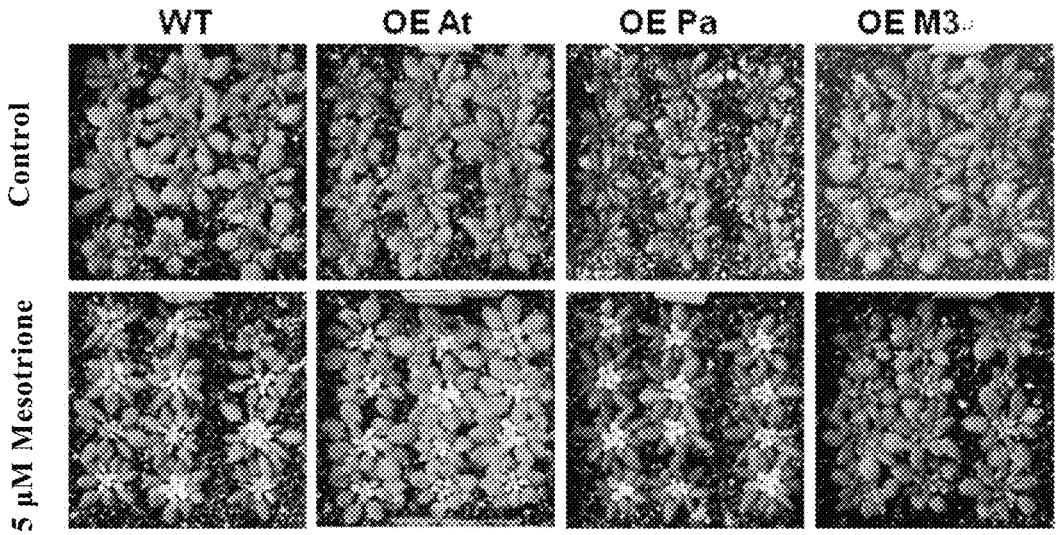
FIG. 15 shows the resistance to herbicide (mesotrione) of potted *Arabidopsis.* Abbreviations: WT (Co10); OE At: overexpression line of AtHPPD; OE Pa: overexpression line of PaHPPD; OE M3: overexpression line of PaHPPD-M3.

The results are shown in FIG. 15. Two weeks after herbicide spray to potted *Arabidopsis,* there is no difference in the seedling phenotype of control treated (0.05% Tween-20) AtHPPD (OE At), PaHPPD (OE Pa) and PaHPPD-M3 (OE M3) overexpression lines with WT, and there is a large difference in phenotype between OE M3 line and other lines treated with 5 μM mesotrione, wherein the phenotypes of WT, OE At and OE Pa lines are similar, and the new leaves of their seedlings have been completely albino, while the OE M3 line grows well and shows significant resistance. It is indicated that the PaHPPD-M3 gene has an important role in the regulation of triketone herbicide resistance.

Plant RNA Extraction Kit (Beijing Huayueyang Biological Technology Co., Ltd., China). The concentration of RNA samples was measured using NanoDrop ND1000 (Thermo Scientific, USA). RNA samples with an absorbance ratio (at wavelengths of 260/280 nm and 260/230 nm) of approximately 2.0 were selected. The total RNA (1,000 ng) was then used for synthesis of cDNA for reverse transcription using a cDNA synthesis kit (One-step Removal of Transcript gDNA and cDNA Synthesis Super Kit, TransGen).

As for quantitative reverse transcription PCR analysis, 3.0 μL cDNA was used as a template in a 20 μL reaction system to detect the expression levels of HPPD as well as VTE1 and VTE3 genes which encode the key enzymes in the biosynthesis of vitamin E, and actin was used as an internal reference gene. The primer sequences used are listed in Table 4. Three technical repetitions were performed on the Bio-Rad CFX96 real-time system. REST software was used for statistical analysis.

TABLE 4 qRT-PCR primers used in the present invention

| S. No. | Primer name | Primer sequence | SEQ ID NO. |
|---|---|---|---|
| 1 | qACT3 F | 5'GGTCGTACTACTGGTATTGTGCT3' | SEQ ID NO: 27 |
|   | qACT3 R | 5'TGACAATTTCACGCTCAGCT3' | SEQ ID NO: 28 |
| 2 | qAtHPPD F | 5'GCGGTTTAAATTCAGCGGTCCTG3' | SEQ ID NO: 29 |
|   | qAtHPPD R | 5'TCCGTGCACTGGCTCGTTAATC3' | SEQ ID NO: 30 |
| 3 | qVTE1 F | 5'TGTCCGAAGGGTTCCAAGCTAC3' | SEQ ID NO: 31 |
|   | qVTE1 R | 5'CACAGTTTCCGCATAGTCAGTACG3' | SEQ ID NO: 32 |
| 4 | qVTE3 F | 5'AAGATCGTCGAGGGAGATGCTG3' | SEQ ID NO: 33 |
|   | qVTE3 R | 5'TCCGGCCAGTACTCAATGCTTC3' | SEQ ID NO: 34 |
| 5 | qGmACT3 F | 5'ATCTTGACTGAGCGTGGTTATTCC3' | SEQ ID NO: 35 |
|   | GmACT3 R | 5'GCTGGTCCTGGCTGTCTCC-3' | SEQ ID NO: 36 |
| 6 | qGmHPPD F | 5'GACAGGCCAACGATATTCATAGA3' | SEQ ID NO: 37 |
|   | qGmHPPD R | 5'CTATGCCACATTGATTCCTCATT3' | SEQ ID NO: 38 |
| 7 | qGmHST F | 5'TTTCAGGCGTTGGTTACTCATAC3' | SEQ ID NO: 39 |
|   | qGmHST R | 5'TCTAACTATGCACGTATGCACCTT3' | SEQ ID NO: 40 |
| 8 | qGmHPT F | 5'GGCTTCAATTCTCTGGTTTCA3' | SEQ ID NO: 41 |
|   | qGmHPT R | 5'CTGACAAAGGCAGCACCAT3' | SEQ ID NO: 42 |
| 9 | qGmMPQ MT F | 5'GTTTATTCCAAAAGGGTGTGCT3' | SEQ ID NO: 43 |
|   | qGmMPQ MT R | 5'GCGGTTGTAGAGATCAGCA3' | SEQ ID NO: 44 |
| 10 | qGmTC F | 5'ATGGAAGCCAAGCTCTGG3' | SEQ ID NO: 45 |
|   | qGmTC R | 5'CTACAGGCCAGGCGGTTT3' | SEQ ID NO: 46 |

EXAMPLE 10

Expression of Biosynthesis Genes of AtHPPD and Vitamin E in *Arabidopsis*

Figure 16:
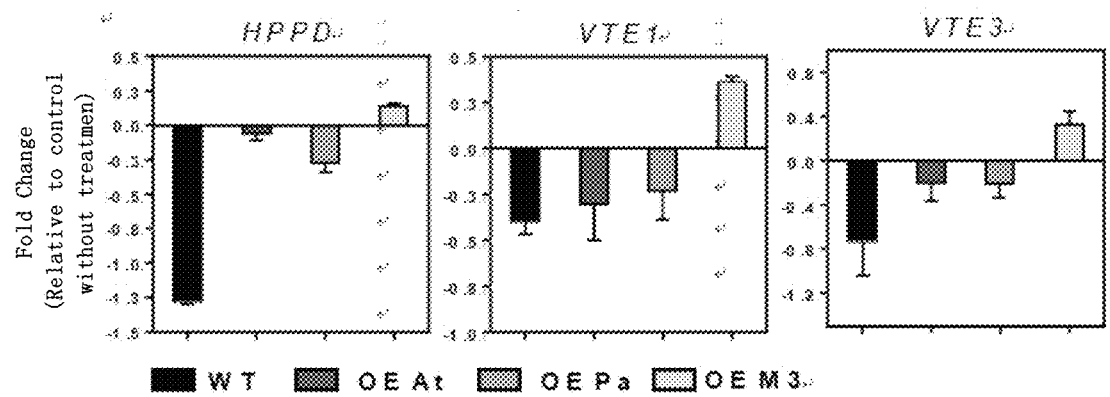
FIG. 16 shows the relative expression levels of HPPD and vitamin E biosynthesis genes (VTE1 and VTE3) of WT (Co10), OE At (overexpression line of AtHPPD), OE Pa (overexpression line of PaHPPD), and OE M3 (overexpression line of PaHPPD-M3) after herbicide (250 nM mesotrione) treatment for 6 h.

2 week-old T3 generation seedlings of WT, OE At, OE Pa and OE M3 were used as materials to set up a treatment group and a control group, respectively, wherein the treatment group was continuously cultured in ½ MS liquid medium containing 250 nM mesotrione for 6 h. The total RNA of related materials was extracted using Super Fast FIG. 16 shows the transcription abundance of HPPD, VTE1 (vitamin E cyclase) and VTE3 (2-methyl-6-phytoyl-1,4-hydroquinone methyltransferase) of *Arabidopsis* seedlings treated with herbicide (mesotrione) for 6 h using qRT-PCR analysis. Compared with the 2 week-old T3 generation seedlings of WT, OE At, OE Pa, and OE M3 that were not treated with mesotrione, the expression levels of HPPD, VTE1 and VTE3 in the leaves of OE At, OE Pa, and WT lines treated with herbicides were inhibited to varying degrees. The HPPD gene expression level of OE M3 line was basically not inhibited, while the gene expression levels of VTE1 and VTE3 were up-regulated. It is indicated that the HPPD, VTE1 and VET3 genes of OE M3 treated with herbicides were not affected or had little effect. At the same time, during the herbicide treatment, vitamin E can be continuously synthesized in the OE M3 line, but inhibited in WT, OE At, and OE Pa lines.

EXAMPLE 11

Oxidative Stress Marker of the Overexpression Line OE M3 *Arabidopsis*

Herbicides cause the production of reactive oxygen species (ROS), leading to cell death. In order to clarify the oxidation state of plants, the leaves of plants treated with herbicide mesotrione and control were stained with nitroblue tetrazolium (NBT) and 3,3'-diaminobenzidine (DAB) to analyze the accumulation of superoxide ($O_2$) and hydrogen peroxide ($H_2O_2$).

2 week-old T3 generation *Arabidopsis* seedlings of WT, OE At, OE Pa and OE M3 were transfered to different control (½ MS medium) and treatment medium (½ MS medium containing 100 nM mesotrione) for 72 h, and then stained with NBT and DAB to detect the accumulation of reactive oxygen species.

Figure 17:
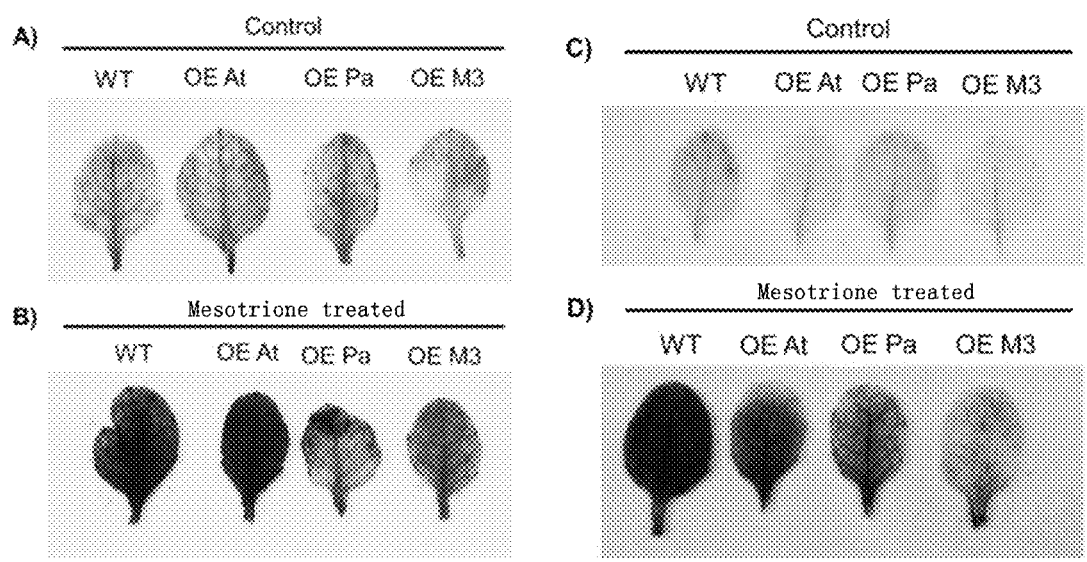
FIG. 17 shows the accumulation of superoxide and hydrogen peroxide (stained with NBT and DAB, respectively) induced by herbicide (100 nM mesotrione) treatment in *Arabidopsis.* Wherein, FIGS. 17A and 17B respectively show the NBT dyeing results of two-week old seedlings of WT (Co10), OE At, OE Pa, and OE M3 cultured in the control medium (½ MS medium without herbicide) and herbicide-containing Medium CA MS medium containing 100 nM mesotrione) for 72 h.

The results are shown in FIG. 17. The accumulation of superoxide and hydrogen peroxide in the leaves of plants not treated with mesotrione was similar among the lines, while the accumulation amount was greatly different in different *Arabidopsis* lines treated with 100 nM mesotrione. Compared with WT, OE At and OE Pa, the accumulation of superoxide and hydrogen peroxide of OE M3 is significantly reduced. It is indicated that the herbicide-induced ROS production and the resulting cell death are not obvious in the OE M3 strain. That is, the OE M3 line solves the problem of ROS accumulation more effectively.

EXAMPLE 12

Evaluation of Herbicide Resistance of T0 Generation OE SDM Rice Lines

Analysis of Resistance of OE SDM Rice to Herbicides at Pot Level

Figure 18:
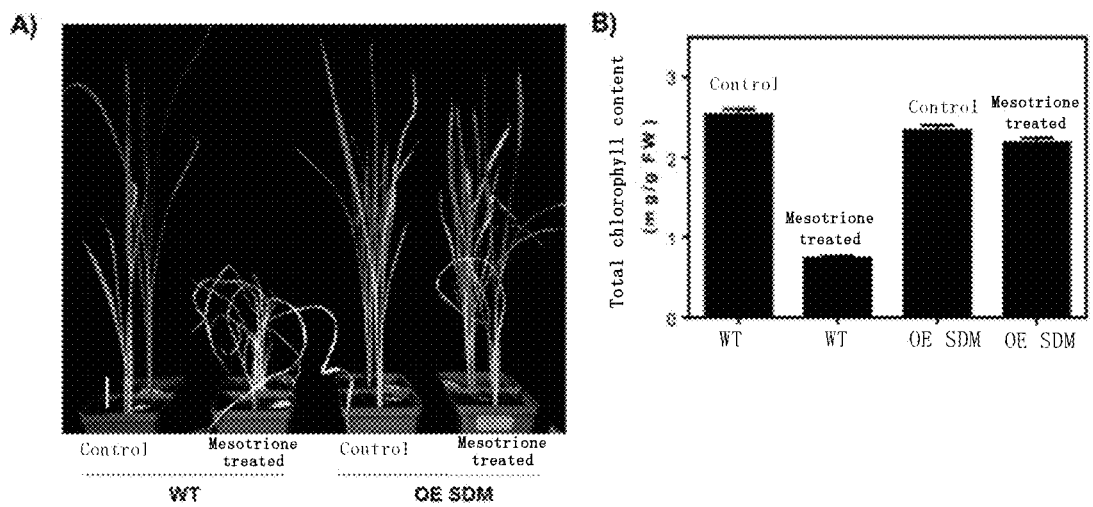
FIG. 18 shows the resistance to herbicide (200 μM mesotrione) of potted rice.

As can be seen from FIG. 18A, compared with the control treatment of 0.1% Tween-20, 21 d (3 weeks) after the spray treatment of 200μM mesotrione (prepared with 0.1% Tween-20), most of the leaves of WT plant withered and died, and the leaves of the OE SDM rice line had very small visible signs of damage, that is, it could grow normally under 200μM mesotrione. It is indicated that the resistance of OE SDM rice seedlings to triketone herbicides reached 200 μM and was significantly higher than that of WT.

Total Chlorophyll Content of Rice Leaves

FIG. 18B shows that under control conditions (0.1% Tween-20 treatment), the total chlorophyll content of WT and OE SDM rice leaves was not significantly different. Compared with OE SDM rice treated with 200 μM mesotrione (prepared with 0.1% Tween-20) for 2 weeks, the total chlorophyll content in leaves of WT rice treated with 200 μM mesotrione (prepared with 0.1% Tween-20) was greatly reduced. It is indicated that OE SDM rice line has stronger resistance to triketone herbicides than WT rice.

Oxidative Stress Markers in Rice Leaves 1 week after the treatment of control (spray 0.1% Tween-20) and 200 μM mesotrione (prepared with 0.1% Tween-20), the leaves of WT and OE SDM rice were stained with NBT (FIGS. 19A and 19B) and DAB (FIGS. 19C and 19D), respectively. It was found that neither the WT nor OE SDM rice leaves of the control treatment had ROS accumulation, but there was a large number of $O_2$ and $H_2O_2$ accumulation in WT rice leaves 1 week after the treatment with 200 μM mesotrione, while there was little $O_2$ and $H_2O_2$ accumulation in OE SDM rice leaves. It is indicated that OE SDM rice has stronger resistance to triketone herbicides.

Malondialdehyde (MDA) Content in Rice Leaves

Figure 19:
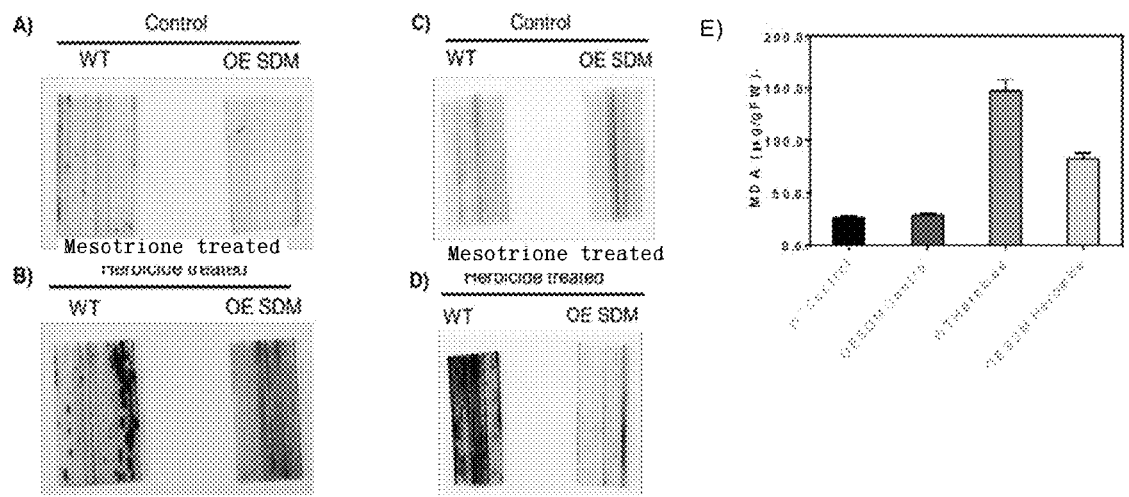
FIG. 19 shows the content of oxidative stress markers (superoxide, hydrogen peroxide and MDA) of rice leaves 1 week after spraying with control (0.1% Tween-20) and 200 μM mesotrione (prepared with 0.1% Tween-20).

FIG. 19E shows that under normal growth conditions (control treatment with 0.1% Tween-20), the MDA contents in leaves of WT and OE SDM rice line are low and similar. However, 1 week after the spray treatment with 200 μM mesotrione (prepared with 0.1% Tween-20), the MDA content in WT rice leaves was significantly higher than that of OE SDM rice leaves. It is indicated that overexpression of PaHPPD-SDM in OE SDM rice prevents lipid peroxidation and enhances resistance to triketone herbicides.

Example 13

Herbicide Resistance of T0 and T1 Generation OE SDM Soybean Lines-Leaf Spread

Figure 20:
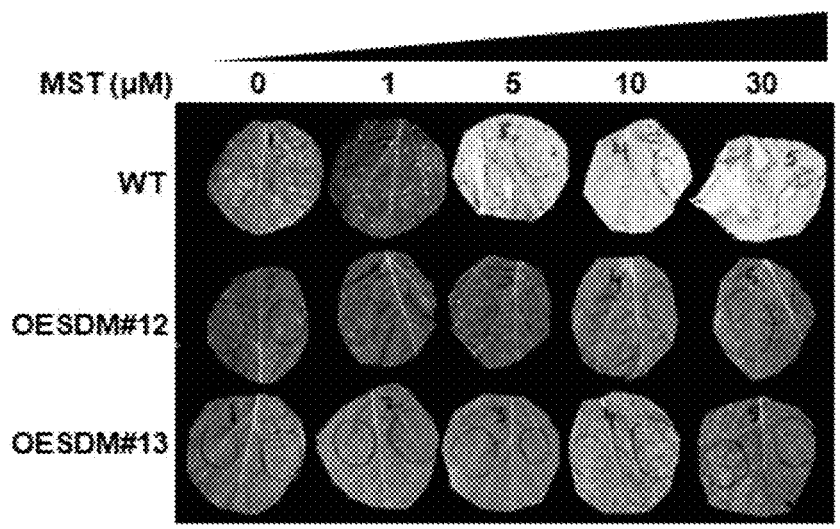
FIG. 20 shows the analysis of resistance to triketone herbicide (mesotrione) of TO generation soybean plants of OE PaHPPD-SDM at the leaf leave. Different concentrations of mesotrione (0, 1, 5, 10, 30 μM prepared with 0.1% Tween 20) and control (0.1% Tween 20) were dipped with cotton swabs, and coated to the leaves of 4 week old TO generation soybean plants of OE PaHPPD-SDM (OESDM #12 and OESDM #13) and WT. The photographs were taken 2 weeks after of treatment.
Figure 21:
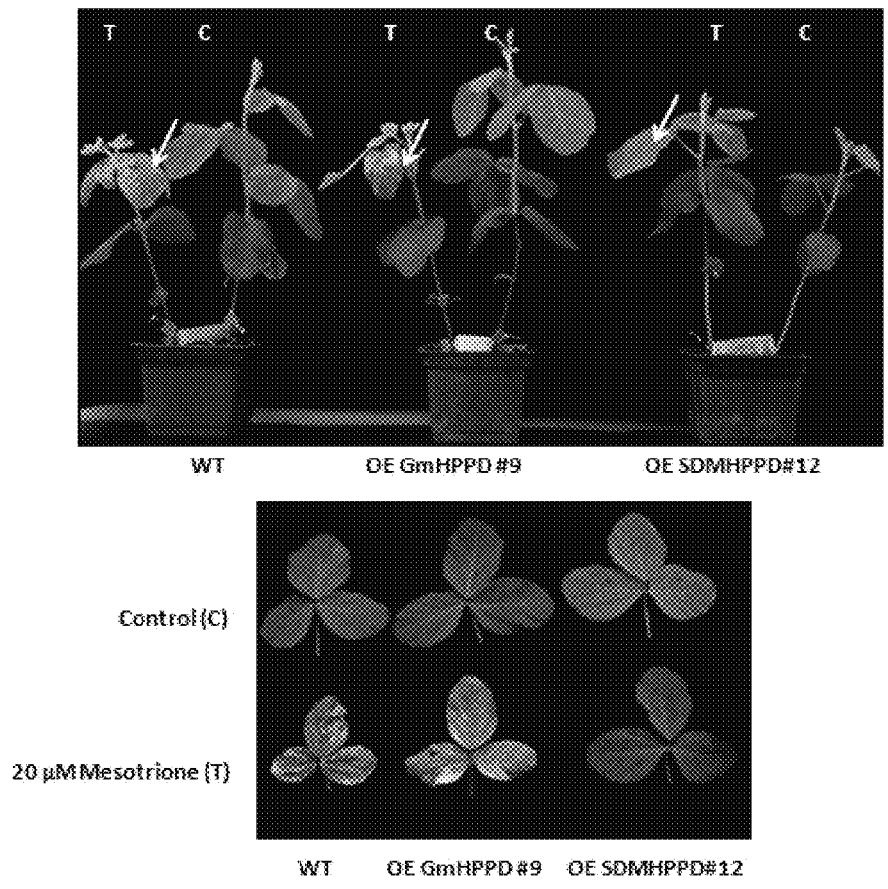
FIG. 21 shows the analysis of resistance to triketone herbicide (mesotrione) of T1 generation soybean plants of OE PaHPPD-SDM in leaf leave. 20 μM mesotrione (prepared with 0.1% Tween 20) and control (0.1% Tween 20) were dipped with cotton swabs, and coated evenly to the leaves of 2 week old T1 generation soybean plants of OE PaHPPD-SDM, T1 generation soybean plants of OE GmHPPD and WT. The photographs were taken 10 days after of treatment. Abbreviations: C (control): control treatment; T (Treatment): herbicide treatment.

The resistance of T0 and T1 soybean lines of OE PaHPPD-SDM and the wild-type soybean William 82 to herbicides was detected and compared by coating herbicides to the leaves. As can be seen from FIGS. 20 and 21, 2 weeks after the treatment of different concentrations of mesotrione (0, 1, 5, 10 and 30 μM, prepared with 0.1% Tween-20), the leaves of wild-type soybean William 82 already showed albino symptom when the concentration of mesotrione reached 5μM, and with the increase of concentration, the albino symptom became more serious. Compared with wild-type soybean William 82, the OE PaHPPD-SDM soybean line had a high tolerance to herbicides and did not show symptoms of albino and damage even at a mesotrione concentration of 30 μM. Therefore, the efficiency of PaHPPD-SDM gene to HPPD inhibitors was proved.

EXAMPLE 14

Herbicide Resistance of T1 Generation OE SDM Soybean Line-Whole Plant Spraying

Figure 22:
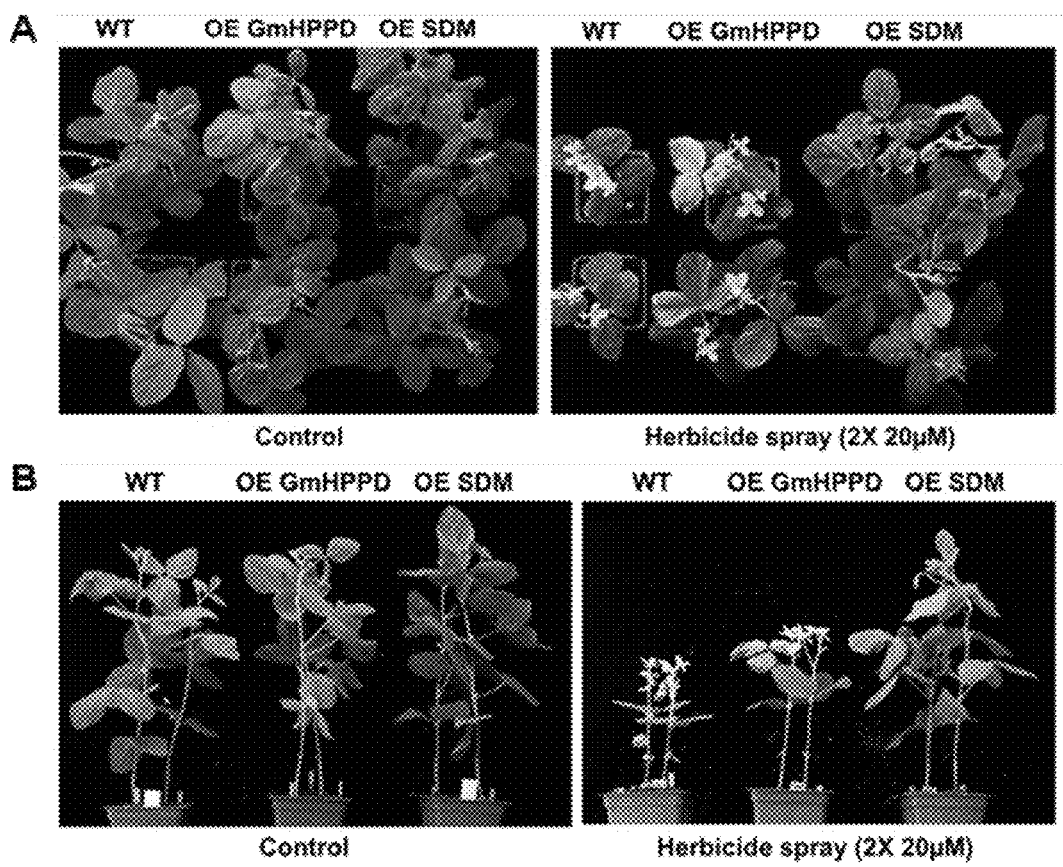
FIG. 22 shows the analysis of resistance to triketone herbicide (mesotrione) of T1 generation soybean line at the whole plant level. 4 week old soybean plants of T1 generation of OE PaHPPD-SDM, T1 generation of OE GmHPPD and WT were sprayed respectively with 20 μM mesotrione (prepared with 0.1% Tween-20) and control (0.1% Tween-20) for the first time. A second spray was applied after 1 week. The figure shows photographs 2 weeks after the spraying treatment. A: top view, B: side view. Abbreviations: WT: wild type soybean William 82; OE GmHPPD: soybean line over-expressed soybean HPPD gene; OE SDM: soybean line over-expressed PaHPPD-SDM gene.

The herbicide resistance of OE PaHPPD-SDM soybean T1 generation line, OE GmHPPD soybean T1 generation line and wild type soybean William 82 was detected and compared by the method of whole plant spraying. FIG. 22 shows the phenotypes of 4 week-old seedlings of T1 generation of OE PaHPPD-SDM, T1 generation of OE GmHPPD and wild-type soybean William 82, after spraying twice with 20 μM mesotrione. The figure shows the phenotypes 10 days after the treatment. It was found that the wild-type soybean William 82 and the OE GmHPPD T1 generation line showed obvious characteristics of albino symptom and growth retardation after treatment with mesotrione, wherein the sensitivity of wild-type soybean William 82 to herbicide was more obvious than the OE GmHPPD T1 generation line. The OE PaHPPD-SDM T1 generation line grew normally after treatment with mesotrione and did not show any albino symptom. It was shown that OE PaHPPD-SDM soybean significantly improved its resistance to herbicides.

EXAMPLE 15

Figure 23:
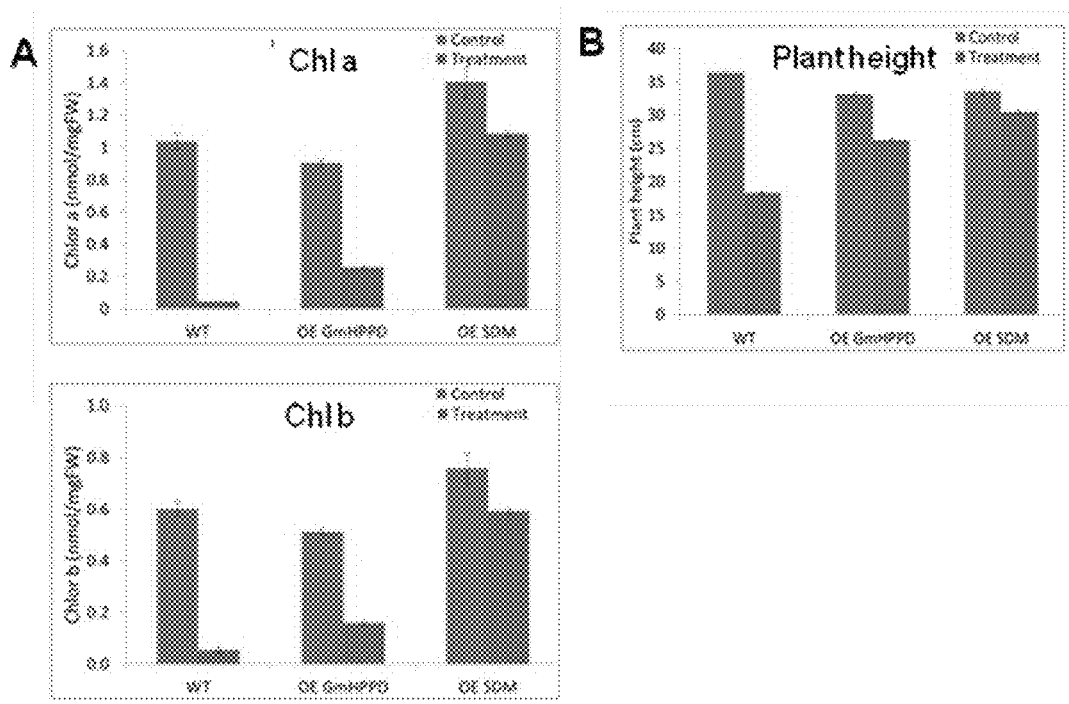
FIG. 23 shows the chlorophyll content and plant height of T1 generation of soybean lines treated with triketone herbicide (mesotrione). 4 week old soybean plants of T1 generation of OE PaHPPD-SDM, T1 generation of OE GmHPPD and WT were sprayed respectively with 20 μM mesotrione (prepared with 0.1% Tween-20) and control (0.1% Tween-20) for the first time. A second spray was applied after 1 week. The chlorophyll content and plant height were measured 2 weeks after the treatment. A shows the content of chlorophyll a and chlorophyll b in the leaves, and B shows the plant height. Abbreviations are the same as FIG. 22.

Chlorophyll Content and Plant Height of T1 Generation OE SDM Soybean-Whole Plant Spraying The herbicide resistance of OE PaHPPD-SDM soybean T1 generation line, OE GmHPPD soybean T1 generation line and wild type soybean William 82 was detected and compared by the method of whole plant spraying. FIG. 23A shows that 4 week-old seedlings of T1 generation of OE PaHPPD-SDM, T1 generation of OE GmHPPD, and wild-type soybean William 82 were sprayed twice with 20 μM mesotrione. 2 weeks after the treatment, it was found that the contents of chlorophyll a and chlorophyll b in the leaves of OE GmHPPD and wild-type soybean William 82 sprayed with mesotrione were significantly lower than that of the control treatment, and the performance of wild-type soybean William 82 was more significant. At the same time, it was found that the contents of chlorophyll a and chlorophyll b in the leaves of OE PaHPPD-SDM sprayed with mesotrione were reduced compared with the control, but the contents of chlorophyll a and chlorophyll b were both significant higher than that of OE GmHPPD and wild-type soybean William 82 treated with mesotrione. It was shown that mesotrione treatment significantly reduced the total chlorophyll content of OE GmHPPD and wild-type soybean William 82, while slightly reduced the chlorophyll content of OE PaHPPD-SDM. At the same time, it can be seen from FIG. 23B that the plant height of the mesotrione-treated soybean is lower than that of the control, but the overall expression is OE PaHPPD-SDM>OE GmHPPD>wild-type soybean William 82. It showed that OE PaHPPD-SDM soybean significantly improved its resistance to triketone herbicides.

EXAMPLE 16 qPCR Analysis of the Expression of HPPD and Tocopherol Biosynthesis Genes in Soybean 4 week-old T1 generation seedlings of WT, OE GmHPPD and OE PaHPPD-SDM were used as materials to set up a treatment group and a control group, respectively, wherein the treatment group was continuously cultured in ½ MS liquid medium containing 20 μM mesotrione for 12 h. The total RNA of related materials was extracted using Super Fast Plant RNA Extraction Kit (Beijing Huayueyang Biological Technology Co., Ltd., China). The concentration of RNA samples was measured using NanoDrop ND1000 (Thermo Scientific, USA). RNA samples with an absorbance ratio (at wavelengths of 260/280 nm and 260/230 nm) of approximately 2.0 were selected. The total RNA (1,000 ng) was then used for synthesis of cDNA for reverse transcription using a cDNA synthesis kit (One-step Removal of Transcript gDNA and cDNA Synthesis Super Kit, Trans-Gen).

As for quantitative reverse transcription PCR analysis, 3.0 μL cDNA was used as a template in a 20 μL reaction system, and gene-specific primers such as qGmHPPD F and qGmHPPD R were used for GmHPPD gene, qGmHST F and qGmHST R were used for GmHPT gene (alkapton lycopene transferase gene), qGmHPT F and qGmHPT R were used for GmHPT or VTE2 genes, GmMPQMT F and MPQMT R were used for GmMPQMT methyl transferase genes (also known as VTE3), GmTC F and GmTC R were used for GmTC genes (also known as VTE1, tocopherol cyclase gene). These VTE (1, 2 and 3) genes were selected because they encode the key enzymes involved in tocopherol biosynthesis. The primer sequences used in the present invention are listed in Table 4. Three technical repetitions were performed on the Bio-Rad CFX96 real-time system. REST software was used for statistical analysis.

Figure 24:
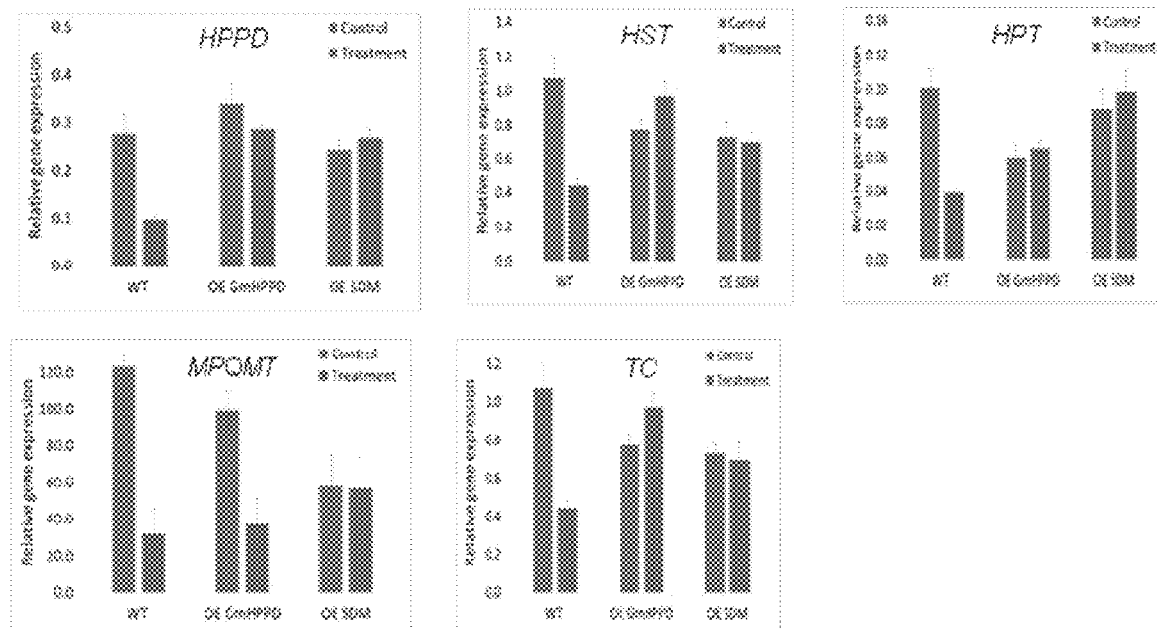
FIG. 24 shows the expression of different tocopherol biosynthesis genes in different soybean lines (WT, OE GmHPPD and OE SDM). 4 week-old T1 generation of soybean seedlings of OE GmHPPD, OE PaHPPD-SDM and WT were continuously cultured in treatment group (Y2 MS liquid medium containing 20 μm mesotrione) and control group (½ MS liquid medium) for 12 h. Then the expression quantity of tocopherol biosynthesis genes in leaves was analyzed by qPCR. Wherein the abbreviations are as follows: WT: wild-type soybean William 82; OE GmHPPD: GmHPPD gene overexpression; OE PaHPPD-SDM: PaHPPD-SDM gene overexpression; GmHPPD gene: soybean HPPD gene; GmHST gene: phytoene transferase gene; GmTC gene is also called VTE1: tocopherol cyclase gene; GmHPT or VTE2, GmMPQMT methyl transferase gene: VTE3.

FIG. 24 shows the transcript abundance of GmHPPD gene, GmHPT gene, GmHPT or VTE2 gene, GmMPQMT or VTE3, GmTC or VTE1 (tocopherol cyclase gene) in seedlings treated with herbicide (mesotrione) detected by qRT-PCR method. These genes are the key genes involved in the tocopherol biosynthesis pathway. As can be seen from FIG. 24, compared with the control, the expression of GmHPPD gene, HST gene, HPT gene, MPQMT gene and TC gene involved in the tocopherol synthesis pathway were significantly reduced in the wild-type soybean William 82 treated with mesotrione for 12 h. Compared with the control, the expression levels of GmHPPD and MPQMT genes were decreased in the OE GmHPPD soybean T1 generation line treated with mesotrione for 12 h, while the expression levels of HST, HPT and TC genes were increased. Compared with the control, the expression levels of GmHPPD and HPT genes were up-regulated in OE PaHPPD-SDM soybean T1 generation line treated with mesotrione for 12 h, and the expression levels of HST, MPQMT and TC genes were almost unchanged. It is indicated that under the condition of triketone herbicide (mesotrione) treatment, OE PaHPPD-SDM (OESDM) showed sustained tocopherol biosynthesis, which was inhibited in wild-type soybeans William 82 and OE GmHPPD.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. An isolated herbicide resistance polypeptide comprising the amino acid sequence as set forth in SEQ ID NO: 4, SEQ ID NO: 6, SEQ ID NO: 8, or SEQ ID NO: 10.

2. An isolated polynucleotide encoding the herbicide resistance polypeptide of claim 1.

3. A vector comprising the polynucleotide of claim 2.

4. A host cell comprising the vector of claim 3.

5. A method for producing an herbicide resistance polypeptide, comprising the steps of:
   (a) culturing the host cell of claim 4 under conditions suitable for the expression of the herbicide resistance polypeptide, thereby expressing the herbicide resistance polypeptide; and
   (b) isolating the herbicide resistance polypeptide from said cell.

6. A method for producing a transgenic plant, comprising the steps of:
   (a) introducing, into a plant cell, a polynucleotide encoding the herbicide resistance polypeptide of claim 1; and
   (b) regenerating said transgenic plant from said plant cell;
wherein the transgenic plant is selected from the group consisting of *Arabidopsis*, soybean, and rice.

* * * * *

SEQUENCE LISTING

```
<160> NUMBER OF SEQ ID NOS: 46

<210> SEQ ID NO 1
<211> LENGTH: 1074
<212> TYPE: DNA
<213> ORGANISM: Pesudomonas pyocyaneum

<400> SEQUENCE: 1
atgaacgccg tggccaagat cgaacagcac aatcccatcg gtaccgacgg attcgaattc        60
gtcgagttca ccgcccccga cgccaagggc atcgagcagc tgcgccagct gttcaacatg       120
```

-continued

```
atgggcttca ccgaaaccgc caagcatcgt tccaaggaag tcttcctgtt ccagcagaac      180
gatatcaaca tcgtgctcaa cggcagccca accgggcatg tccatgaatt cgccctcaag      240
cacggcccga gcgcctgcgc catggccttc cgggtgaaga acgcttccca ggccgccgcc      300
tacgccgaat cccagggcgc caagctggtg ggcagccacg ccaacttcgg cgagctgaac      360
atcccttccc tggaaggcat cggcggttcg ctgctgtatc ttgtcgaccg ctacggcgac      420
cgcagcatct atgacgtcga cttcgagttc atcgaaggcc gcagcgccaa cgacaactcg      480
gtcggcctga cctacatcga ccacctgacc cacaacgtca agcgcggcca gatggacgtc      540
tggtccggtt tctacgagcg catcgccaac ttccgcgaga ttcgctactt cgacatcgaa      600
ggcaagctca ccggcctgtt ctcccgcgcc atgaccgcac cttgcgggaa gatccgcatc      660
ccgatcaacg agtcggccga cgatacctcg cagatcgagg aattcatccg cgaataccat      720
ggcgaaggca tccagcacat cgccctgacc accgacgaca tctatgccac cgtgcgcaag      780
ctgcgcgaca acggcgtgaa gttcatgtcg accccggaca cctactacga aaggtcgac      840 acccgcgtcg ccgggcatgg cgagccgctc gagcaactgc gcgaactgaa cctgctgatc      900
gacgcgcccc cgggcgacga cggcatcctg ctgcagatct tcaccgacac ggtgatcggc      960
ccgatcttct tcgagatcat ccagcgcaag ggcaaccagg gtttcggcga gggcaatttc      1020
aaggccctgt tcgagtccat cgaggaagac cagattcgcc gcggcgtgat ctga           1074
```

<210> SEQ ID NO 2
<211> LENGTH: 357
<212> TYPE: PRT
<213> ORGANISM: Pesudomonas pyocyaneum

<400> SEQUENCE: 2

```
Met Asn Ala Val Ala Lys Ile Glu Gln His Asn Pro Ile Gly Thr Asp
1               5                   10                  15

Gly Phe Glu Phe Val Glu Phe Thr Ala Pro Asp Ala Lys Gly Ile Glu
            20                  25                  30

Gln Leu Arg Gln Leu Phe Asn Met Met Gly Phe Thr Glu Thr Ala Lys
        35                  40                  45

His Arg Ser Lys Glu Val Phe Leu Phe Gln Gln Asn Asp Ile Asn Ile
    50                  55                  60

Val Leu Asn Gly Ser Pro Thr Gly His Val His Glu Phe Ala Leu Lys
65                  70                  75                  80

His Gly Pro Ser Ala Cys Ala Met Ala Phe Arg Val Lys Asn Ala Ser
                85                  90                  95

Gln Ala Ala Ala Tyr Ala Glu Ser Gln Gly Ala Lys Leu Val Gly Ser
            100                 105                 110

His Ala Asn Phe Gly Glu Leu Asn Ile Pro Ser Leu Glu Gly Ile Gly
        115                 120                 125

Gly Ser Leu Leu Tyr Leu Val Asp Arg Tyr Gly Asp Arg Ser Ile Tyr
    130                 135                 140

Asp Val Asp Phe Glu Phe Ile Glu Gly Arg Ser Ala Asn Asp Asn Ser
145                 150                 155                 160

Val Gly Leu Thr Tyr Ile Asp His Leu Thr His Asn Val Lys Arg Gly
                165                 170                 175

Gln Met Asp Val Trp Ser Gly Phe Tyr Glu Arg Ile Ala Asn Phe Arg
            180                 185                 190

Glu Ile Arg Tyr Phe Asp Ile Glu Gly Lys Leu Thr Gly Leu Phe Ser
        195                 200                 205
```

Arg Ala Met Thr Ala Pro Cys Gly Lys Ile Arg Ile Pro Ile Asn Glu
    210                 215                 220

Ser Ala Asp Asp Thr Ser Gln Ile Glu Glu Phe Ile Arg Glu Tyr His
225                 230                 235                 240

Gly Glu Gly Ile Gln His Ile Ala Leu Thr Thr Asp Asp Ile Tyr Ala
                245                 250                 255

Thr Val Arg Lys Leu Arg Asp Asn Gly Val Lys Phe Met Ser Thr Pro
            260                 265                 270

Asp Thr Tyr Tyr Glu Lys Val Asp Thr Arg Val Ala Gly His Gly Glu
        275                 280                 285

Pro Leu Glu Gln Leu Arg Glu Leu Asn Leu Leu Ile Asp Gly Ala Pro
    290                 295                 300

Gly Asp Asp Gly Ile Leu Leu Gln Ile Phe Thr Asp Thr Val Ile Gly
305                 310                 315                 320

Pro Ile Phe Phe Glu Ile Ile Gln Arg Lys Gly Asn Gln Gly Phe Gly
                325                 330                 335

Glu Gly Asn Phe Lys Ala Leu Phe Glu Ser Ile Glu Glu Asp Gln Ile
            340                 345                 350

Arg Arg Gly Val Ile
        355

<210> SEQ ID NO 3
<211> LENGTH: 1074
<212> TYPE: DNA
<213> ORGANISM: Artificial Sequence
<220> FEATURE:
<223> OTHER INFORMATION: Polynucleotide

<400> SEQUENCE: 3
atgaacgccg tggccaagat cgaacagcac aatcccatcg gtaccgacgg attcgaattc      60
gtcgagttca ccgcccccga cgccaagggc atcgagcagc tgcgccagct gttcaacatg     120
atgggcttca ccgaaaccgc caagcatcgt tccaaggaag tcttcctgtt ccagcagaac     180
gatatcaaca tcgtgctcaa cggcagccca accgggcatg tccatgaatt cgccctcaag     240
cacggcccga gcgcctgcgc catggccttc cgggtgaaga acgcttccca ggccgccgcc     300
tacgccgaat cccagggcgc caagctggtg gcagccacg ccaacttcgg cgagctgaac     360
atcccttccc tggaaggcat cggcggttcg ctgctgtatc ttgtcgaccg ctacggcgac     420
cgcagcatct atgacgtcga cttcgagttc atcgaaggcc gcagcgccaa cgacaactcg     480
gtcggcctga cctacatcga ccacctgacc cacaacgtca gcgcggcca gatgacgtc     540
tggtccggtt ctacgagcg catcgccaac ttccgcgaga ttcgctactt cgacatcgaa     600
ggcaagctca ccggcctgtt ctcccgcgcc atgaccgcac cttgcgggaa gatccgcatc     660
ccgatcaacg agtcggccga cgatacctcg cagatcgagg aattcatccg cgaataccat     720
ggcgaaggca tccagcacat cgccctgacc accgacgaca tctatgccac cgtgcgcaag     780
ctgcgcgaca acggcgtgaa gttcatgtcg accccggaca cctactacga aaggtcgac      840
accagcgtcg ccgggcatgg cgagccgctc gagcaactgc gcgaactgaa cctgctgatc     900
gacggcgccc cgggcgacga cggcatcctg ctgcagatct tcaccgacac ggtgatcggc     960
ccgatcttct tcgagatcat ccagcgcaag ggcaaccagg gtttcggcga gggcaatttc    1020
aaggccctgt tcgagtccat cgaggaagac cagattcgcc gcggcgtgat ctga          1074

<210> SEQ ID NO 4

<211> LENGTH: 357
<212> TYPE: PRT
<213> ORGANISM: Artificial Sequence
<220> FEATURE:
<223> OTHER INFORMATION: Peptide

<400> SEQUENCE: 4

```
Met Asn Ala Val Ala Lys Ile Glu Gln His Asn Pro Ile Gly Thr Asp
1               5                   10                  15

Gly Phe Glu Phe Val Glu Phe Thr Ala Pro Asp Ala Lys Gly Ile Glu
            20                  25                  30

Gln Leu Arg Gln Leu Phe Asn Met Met Gly Phe Thr Glu Thr Ala Lys
        35                  40                  45

His Arg Ser Lys Glu Val Phe Leu Phe Gln Gln Asn Asp Ile Asn Ile
    50                  55                  60

Val Leu Asn Gly Ser Pro Thr Gly His Val His Glu Phe Ala Leu Lys
65                  70                  75                  80

His Gly Pro Ser Ala Cys Ala Met Ala Phe Arg Val Lys Asn Ala Ser
                85                  90                  95

Gln Ala Ala Ala Tyr Ala Glu Ser Gln Gly Ala Lys Leu Val Gly Ser
            100                 105                 110

His Ala Asn Phe Gly Glu Leu Asn Ile Pro Ser Leu Glu Gly Ile Gly
        115                 120                 125

Gly Ser Leu Leu Tyr Leu Val Asp Arg Tyr Gly Asp Arg Ser Ile Tyr
    130                 135                 140

Asp Val Asp Phe Glu Phe Ile Glu Gly Arg Ser Ala Asn Asp Asn Ser
145                 150                 155                 160

Val Gly Leu Thr Tyr Ile Asp His Leu Thr His Asn Val Lys Arg Gly
                165                 170                 175

Gln Met Asp Val Trp Ser Gly Phe Tyr Glu Arg Ile Ala Asn Phe Arg
            180                 185                 190

Glu Ile Arg Tyr Phe Asp Ile Glu Gly Lys Leu Thr Gly Leu Phe Ser
        195                 200                 205

Arg Ala Met Thr Ala Pro Cys Gly Lys Ile Arg Ile Pro Ile Asn Glu
    210                 215                 220

Ser Ala Asp Asp Thr Ser Gln Ile Glu Glu Phe Ile Arg Glu Tyr His
225                 230                 235                 240

Gly Glu Gly Ile Gln His Ile Ala Leu Thr Thr Asp Asp Ile Tyr Ala
                245                 250                 255

Thr Val Arg Lys Leu Arg Asp Asn Gly Val Lys Phe Met Ser Thr Pro
            260                 265                 270

Asp Thr Tyr Tyr Glu Lys Val Asp Thr Ser Val Ala Gly His Gly Glu
        275                 280                 285

Pro Leu Glu Gln Leu Arg Glu Leu Asn Leu Leu Ile Asp Gly Ala Pro
    290                 295                 300

Gly Asp Asp Gly Ile Leu Leu Gln Ile Phe Thr Asp Thr Val Ile Gly
305                 310                 315                 320

Pro Ile Phe Phe Glu Ile Ile Gln Arg Lys Gly Asn Gln Gly Phe Gly
                325                 330                 335

Glu Gly Asn Phe Lys Ala Leu Phe Glu Ser Ile Glu Glu Asp Gln Ile
            340                 345                 350

Arg Arg Gly Val Ile
        355
```

<210> SEQ ID NO 5

<211> LENGTH: 1074
<212> TYPE: DNA
<213> ORGANISM: Artificial Sequence
<220> FEATURE:
<223> OTHER INFORMATION: Polynucleotide

<400> SEQUENCE: 5

```
atgaacgccg tggccaagat cgaacagcac aatcccatcg gtaccgacgg attcgaattc      60
gtcgagttca ccgcccccga cgccaagggc atcgagcagc tgcgccagct gttcaacatg     120
atgggcttca ccgaaaccgc caagcatcgt tccaaggaag tcttcctgtt ccagcagaac     180
gatatcaaca tcgtgctcaa cggcagccca accggacatg tccatgaatt cgccctcaag     240
cacggcccga gcgcctgcgc catggccttc cgggtgaaga cgcttccca  ggccgccgcc     300
tacgccgaat cccagggcgc caagctggtg ggcagccacg ccaacttcgg cgagctgaac     360
atcccttccc tggaaggcat cggcggttcg ctgctgtatc ttgtcgaccg ctacggcgac     420
cgcagcatct atgacgtcga cttcgagttc atcgaaggcc gcagcgccaa cgacaactcg     480
gtcggcctga cctacatcga ccacctgacc cacaacgtca gcgcggcca  gatggacgtc     540
tggtccggtt ctacgagcg  catcgccaac ttccgcgaga ttcgctactt cgacatcgaa     600
ggcaagctca ccggcctgtt ctcccgcgcc atgaccgcac cttgcgggaa gatccgcatc     660
ccgatcaacg agtcggccga cgatacctcg cagatcgagg aattcatccg cgaataccat     720
ggcgaaggca tccagcacat cgccctgacc accgacgaca tctatgccac cgtgcgcaag     780
ctgcgcgaca acggcgtgaa gttcatgtcg accccggaca cctactacga aggtcgac      840
accagcgtcg ccgggcatgg cgagccgctc gagcaactgc gcgaactgaa cctgctgatc     900
gacggcgccc cgggcgacga cggcatcctg ctgcagatct tcaccgacac ggtgatcggc     960
ccgatcttct tcgagatcat ccagcgcaag ggcaaccagg gtttcggcga gggcaatttc    1020
aaggccctgt tcgagtccat cgagaaagac cagattcgcc gcggcgtgat ctga          1074
```

<210> SEQ ID NO 6
<211> LENGTH: 357
<212> TYPE: PRT
<213> ORGANISM: Artificial Sequence
<220> FEATURE:
<223> OTHER INFORMATION: Peptide

<400> SEQUENCE: 6

```
Met Asn Ala Val Ala Lys Ile Glu Gln His Asn Pro Ile Gly Thr Asp
1               5                   10                  15

Gly Phe Glu Phe Val Glu Phe Thr Ala Pro Asp Ala Lys Gly Ile Glu
            20                  25                  30

Gln Leu Arg Gln Leu Phe Asn Met Met Gly Phe Thr Glu Thr Ala Lys
        35                  40                  45

His Arg Ser Lys Glu Val Phe Leu Phe Gln Gln Asn Asp Ile Asn Ile
    50                  55                  60

Val Leu Asn Gly Ser Pro Thr Gly His Val His Glu Phe Ala Leu Lys
65                  70                  75                  80

His Gly Pro Ser Ala Cys Ala Met Ala Phe Arg Val Lys Asn Ala Ser
                85                  90                  95

Gln Ala Ala Ala Tyr Ala Glu Ser Gln Gly Ala Lys Leu Val Gly Ser
            100                 105                 110

His Ala Asn Phe Gly Glu Leu Asn Ile Pro Ser Leu Glu Gly Ile Gly
        115                 120                 125

Gly Ser Leu Leu Tyr Leu Val Asp Arg Tyr Gly Asp Arg Ser Ile Tyr
```

```
                130               135              140
Asp Val Asp Phe Glu Phe Ile Glu Gly Arg Ser Ala Asn Asp Asn Ser
145                 150                 155                 160

Val Gly Leu Thr Tyr Ile Asp His Leu Thr His Asn Val Lys Arg Gly
                165                 170                 175

Gln Met Asp Val Trp Ser Gly Phe Tyr Glu Arg Ile Ala Asn Phe Arg
            180                 185                 190

Glu Ile Arg Tyr Phe Asp Ile Glu Gly Lys Leu Thr Gly Leu Phe Ser
                195                 200                 205

Arg Ala Met Thr Ala Pro Cys Gly Lys Ile Arg Ile Pro Ile Asn Glu
            210                 215                 220

Ser Ala Asp Asp Thr Ser Gln Ile Glu Glu Phe Ile Arg Glu Tyr His
225                 230                 235                 240

Gly Glu Gly Ile Gln His Ile Ala Leu Thr Thr Asp Asp Ile Tyr Ala
                245                 250                 255

Thr Val Arg Lys Leu Arg Asp Asn Gly Val Lys Phe Met Ser Thr Pro
            260                 265                 270

Asp Thr Tyr Tyr Glu Lys Val Asp Thr Ser Val Ala Gly His Gly Glu
        275                 280                 285

Pro Leu Glu Gln Leu Arg Glu Leu Asn Leu Leu Ile Asp Gly Ala Pro
    290                 295                 300

Gly Asp Asp Gly Ile Leu Leu Gln Ile Phe Thr Asp Thr Val Ile Gly
305                 310                 315                 320

Pro Ile Phe Phe Glu Ile Ile Gln Arg Lys Gly Asn Gln Gly Phe Gly
            325                 330                 335

Glu Gly Asn Phe Lys Ala Leu Phe Glu Ser Ile Glu Glu Asp Gln Ile
            340                 345                 350

Arg Arg Gly Val Ile
        355

<210> SEQ ID NO 7
<211> LENGTH: 1074
<212> TYPE: DNA
<213> ORGANISM: Artificial Sequence
<220> FEATURE:
<223> OTHER INFORMATION: Polynucleotide

<400> SEQUENCE: 7
atgaacgccg tggccaagat cgaacagcac aatcccatcg gtaccgacgg attcgaattc      60
gtcgagttca ccgcccccga cgccaagggc atcgagcagc tgcgccagct gttcaacatg     120
atgggcttca ccgaaaccgc caagcatcgt tccaaggaag tcttcctgtt ccagcagaac     180
gatatcaaca tcgtgctcaa cggcagccca accgggcatg ccatgaatt cgccctcaag     240 cacggcccga gcgcctgcgc catggccttc cgggtgaaga acgcttccca ggccgccgcc     300
tacgccgaat cccagggcgc caagctggtg gcagccacg ccaacttcgg cgagctgaac     360
atcccttccc tggaaggcat cggcggttcg ctgctgtatc ttgtcgaccg ctacggcgac     420
cgcagcatct atgacgtcga cttcgagttc atcgaaggcc gcagcgtcaa cgacaactcg     480
gtcggcctga cctacatcga ccacctgacc cacaacgtca agcgcggcca gatgacgtc     540 tggtccggtt tctacgagcg catcgccaac ttccgcgaga ttcgctactt cgacatcgaa     600
ggcaagctca ccggcctgtt ctcccgcgcc atgaccgcac cttgcgggaa gatccgcatc     660
ccgatcaacg agtcggccga cgatacctcg cagatcgagg aattcatccg cgaataccat     720
ggcgaaggca tccagcacat cgccctgacc accgacgaca tctatgccac cgtgcgcaag     780
```

```
ctgcgcgaca acggcgtgaa gttcatgtcg accccggaca cctactacga gaaggtcgac    840
accagcgtcg ccgggcatgg cgagccgctc gagcaactgc gcgaactgaa cctgctgatc    900
gacggcgccc cgggcgacga cggcatcctg ctgcagatct tcaccgacac ggtgatcggc    960
ccgatcttct tcgagatcat ccagcgcaag ggcaaccagg gtttcggcga gggcaatttc   1020
aaggccctgt tcgagtccat cgaggaagac cagattcgcc gcggcgtgat ctga         1074
```

<210> SEQ ID NO 8
<211> LENGTH: 357
<212> TYPE: PRT
<213> ORGANISM: Artificial Sequence
<220> FEATURE:
<223> OTHER INFORMATION: Peptide

<400> SEQUENCE: 8

Met Asn Ala Val Ala Lys Ile Glu Gln His Asn Pro Ile Gly Thr Asp
1               5                   10                  15

Gly Phe Glu Phe Val Glu Phe Thr Ala Pro Asp Ala Lys Gly Ile Glu
            20                  25                  30

Gln Leu Arg Gln Leu Phe Asn Met Met Gly Phe Thr Glu Thr Ala Lys
        35                  40                  45

His Arg Ser Lys Glu Val Phe Leu Phe Gln Gln Asn Asp Ile Asn Ile
    50                  55                  60

Val Leu Asn Gly Ser Pro Thr Gly His Val His Glu Phe Ala Leu Lys
65                  70                  75                  80

His Gly Pro Ser Ala Cys Ala Met Ala Phe Arg Val Lys Asn Ala Ser
                85                  90                  95

Gln Ala Ala Ala Tyr Ala Glu Ser Gln Gly Ala Lys Leu Val Gly Ser
            100                 105                 110

His Ala Asn Phe Gly Glu Leu Asn Ile Pro Ser Leu Glu Gly Ile Gly
        115                 120                 125

Gly Ser Leu Leu Tyr Leu Val Asp Arg Tyr Gly Asp Arg Ser Ile Tyr
    130                 135                 140

Asp Val Asp Phe Glu Phe Ile Glu Gly Arg Ser Val Asn Asp Asn Ser
145                 150                 155                 160

Val Gly Leu Thr Tyr Ile Asp His Leu Thr His Asn Val Lys Arg Gly
                165                 170                 175

Gln Met Asp Val Trp Ser Gly Phe Tyr Glu Arg Ile Ala Asn Phe Arg
            180                 185                 190

Glu Ile Arg Tyr Phe Asp Ile Glu Gly Lys Leu Thr Gly Leu Phe Ser
        195                 200                 205

Arg Ala Met Thr Ala Pro Cys Gly Lys Ile Arg Ile Pro Ile Asn Glu
    210                 215                 220

Ser Ala Asp Asp Thr Ser Gln Ile Glu Glu Phe Ile Arg Glu Tyr His
225                 230                 235                 240

Gly Glu Gly Ile Gln His Ile Ala Leu Thr Thr Asp Asp Ile Tyr Ala
                245                 250                 255

Thr Val Arg Lys Leu Arg Asp Asn Gly Val Lys Phe Met Ser Thr Pro
            260                 265                 270

Asp Thr Tyr Tyr Glu Lys Val Asp Thr Ser Val Ala Gly His Gly Glu
        275                 280                 285

Pro Leu Glu Gln Leu Arg Glu Leu Asn Leu Leu Ile Asp Gly Ala Pro
    290                 295                 300

Gly Asp Asp Gly Ile Leu Leu Gln Ile Phe Thr Asp Thr Val Ile Gly

```
305                 310                 315                 320
Pro Ile Phe Phe Glu Ile Ile Gln Arg Lys Gly Asn Gln Gly Phe Gly
                325                 330                 335

Glu Gly Asn Phe Lys Ala Leu Phe Glu Ser Ile Glu Glu Asp Gln Ile
            340                 345                 350

Arg Arg Gly Val Ile
        355

<210> SEQ ID NO 9
<211> LENGTH: 1074
<212> TYPE: DNA
<213> ORGANISM: Artificial Sequence
<220> FEATURE:
<223> OTHER INFORMATION: Polynucleotide

<400> SEQUENCE: 9
atgaacgccg tggccaagat cgaacagcac aatcccatcg gtaccgacgg attcgaattc       60
gtcgagttca ccgcccccga cgccaagggc atcgagcagc tgcgccagct gttcaacatg      120
atgggcttca ccgaaaccgc caagcatcgt tccaaggaag tcttcctgtt ccagcagaac      180
gatatcaaca tcgtgctcaa cggcagccca accggacatg tccatgaatt cgccctcaag      240
cacggcccga gcgcctgcgc catggccttc cgggtgaaga acgcttccca ggccgccgcc      300
tacgccgaat cccagggcgc caagctggtg gcagccacg ccaacttcgg cgagctgaac       360
atcccttccc tggaaggcat cggcggttcg ctgctgtatc ttgtcgaccg ctacggcgac      420
cgcagcatct atgacgtcga cttcgagttc atcgaaggcc gcagcgtcaa cgacaactcg      480
gtcggcctga cctacatcga ccacctgacc cacaacgtca agcgcggcca gatggacgtc      540
tggtccggtt tctacgagcg catcgccaac ttccgcgaga ttcgctactt cgacatcgaa      600
ggcaagctca ccggcctgtt ctcccgcgcc atgaccgcac cttgcgggaa gatccgcatc      660
ccgatcaacg agtcggccga cgatacctcg cagatcgagg aattcatccg cgaataccat      720
ggcgaaggca tccagcacat cgccctgacc accgacgaca tctatgccac cgtgcgcaag      780
ctgcgcgaca acggcgtgaa gttcatgtcg accccggaca cctactacga aaggtcgac      840 accagcgtcg ccgggcatgg cgagccgctc gagcaactgc gcgaactgaa cctgctgatc      900
gacggcgccc cgggcgacga cggcatcctg ctgcagatct tcaccgacac ggtgatcggc      960
ccgatcttct tcgagatcat ccagcgcaag ggcaaccagg gtttcggcga gggcaatttc     1020
aaggccctgt tcgagtccat cgagaaagac cagattcgcc gcggcgtgat ctga           1074

<210> SEQ ID NO 10
<211> LENGTH: 357
<212> TYPE: PRT
<213> ORGANISM: Artificial Sequence
<220> FEATURE:
<223> OTHER INFORMATION: Peptide

<400> SEQUENCE: 10

Met Asn Ala Val Ala Lys Ile Glu Gln His Asn Pro Ile Gly Thr Asp
1               5                   10                  15

Gly Phe Glu Phe Val Glu Phe Thr Ala Pro Asp Ala Lys Gly Ile Glu
            20                  25                  30

Gln Leu Arg Gln Leu Phe Asn Met Met Gly Phe Thr Glu Thr Ala Lys
        35                  40                  45

His Arg Ser Lys Glu Val Phe Leu Phe Gln Gln Asn Asp Ile Asn Ile
    50                  55                  60
```

```
Val Leu Asn Gly Ser Pro Thr Gly His Val His Glu Phe Ala Leu Lys
 65                  70                  75                  80

His Gly Pro Ser Ala Cys Ala Met Ala Phe Arg Val Lys Asn Ala Ser
                 85                  90                  95

Gln Ala Ala Ala Tyr Ala Glu Ser Gln Gly Ala Lys Leu Val Gly Ser
            100                 105                 110

His Ala Asn Phe Gly Glu Leu Asn Ile Pro Ser Leu Glu Gly Ile Gly
        115                 120                 125

Gly Ser Leu Leu Tyr Leu Val Asp Arg Tyr Gly Asp Arg Ser Ile Tyr
    130                 135                 140

Asp Val Asp Phe Glu Phe Ile Glu Gly Arg Ser Val Asn Asp Asn Ser
145                 150                 155                 160

Val Gly Leu Thr Tyr Ile Asp His Leu Thr His Asn Val Lys Arg Gly
                165                 170                 175

Gln Met Asp Val Trp Ser Gly Phe Tyr Glu Arg Ile Ala Asn Phe Arg
            180                 185                 190

Glu Ile Arg Tyr Phe Asp Ile Glu Gly Lys Leu Thr Gly Leu Phe Ser
        195                 200                 205

Arg Ala Met Thr Ala Pro Cys Gly Lys Ile Arg Ile Pro Ile Asn Glu
    210                 215                 220

Ser Ala Asp Asp Thr Ser Gln Ile Glu Glu Phe Ile Arg Glu Tyr His
225                 230                 235                 240

Gly Glu Gly Ile Gln His Ile Ala Leu Thr Thr Asp Asp Ile Tyr Ala
                245                 250                 255

Thr Val Arg Lys Leu Arg Asp Asn Gly Val Lys Phe Met Ser Thr Pro
            260                 265                 270

Asp Thr Tyr Tyr Glu Lys Val Asp Thr Ser Val Ala Gly His Gly Glu
        275                 280                 285

Pro Leu Glu Gln Leu Arg Glu Leu Asn Leu Leu Ile Asp Gly Ala Pro
    290                 295                 300

Gly Asp Asp Gly Ile Leu Leu Gln Ile Phe Thr Asp Thr Val Ile Gly
305                 310                 315                 320

Pro Ile Phe Phe Glu Ile Ile Gln Arg Lys Gly Asn Gln Gly Phe Gly
                325                 330                 335

Glu Gly Asn Phe Lys Ala Leu Phe Glu Ser Ile Glu Lys Asp Gln Ile
            340                 345                 350

Arg Arg Gly Val Ile
        355

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
tatggatcca tgaacgccgt ggccaagatc                                    30

<210> SEQ ID NO 12
<211> LENGTH: 31
<212> TYPE: DNA
<213> ORGANISM: Artificial Sequence
<220> FEATURE:
<223> OTHER INFORMATION: primer

<400> SEQUENCE: 12
```
tcgcggccgc tcagatcacg ccgcggcgaa t          31

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
tatggatcct atgtgtctat cgttagcttc tacagctc          38

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
ctatctcgag ggttcttctt cttgttcatc cca          33

<210> SEQ ID NO 15
<211> LENGTH: 55
<212> TYPE: DNA
<213> ORGANISM: Artificial Sequence
<220> FEATURE:
<223> OTHER INFORMATION: primer

<400> SEQUENCE: 15
gggacaagtt tgtacaaaaa agcaggcttc atgtgtctat cgttagcttc tacag          55

<210> SEQ ID NO 16
<211> LENGTH: 52
<212> TYPE: DNA
<213> ORGANISM: Artificial Sequence
<220> FEATURE:
<223> OTHER INFORMATION: primer

<400> SEQUENCE: 16
gggaccactt tgtacaagaa agctgggtcg gttcttcttc ttgttcatcc ca          52

<210> SEQ ID NO 17
<211> LENGTH: 55
<212> TYPE: DNA
<213> ORGANISM: Artificial Sequence
<220> FEATURE:
<223> OTHER INFORMATION: primer

<400> SEQUENCE: 17
gggacaagtt tgtacaaaaa agcaggcttc atgaacgccg tggccaagat cgaac          55

<210> SEQ ID NO 18
<211> LENGTH: 51
<212> TYPE: DNA
<213> ORGANISM: Artificial Sequence
<220> FEATURE:
<223> OTHER INFORMATION: primer

<400> SEQUENCE: 18
ggggaccact ttgtacaaga aagctgggtc tcagatcacg ccgcggcgaa t          51

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
ggccgcagcg tcaacgacaa c    21

<210> SEQ ID NO 20
<211> LENGTH: 28
<212> TYPE: DNA
<213> ORGANISM: Artificial Sequence
<220> FEATURE:
<223> OTHER INFORMATION: primer

<400> SEQUENCE: 20
ttcgatgaac tcgaagtcga cgtcatag    28

<210> SEQ ID NO 21
<211> LENGTH: 28
<212> TYPE: DNA
<213> ORGANISM: Artificial Sequence
<220> FEATURE:
<223> OTHER INFORMATION: primer

<400> SEQUENCE: 21
ttgtacaatg aacgccgtgg ccaagatc    28

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22
ctcaagcttg atcacgccgc ggcgaatctg gt    32

<210> SEQ ID NO 23
<211> LENGTH: 31
<212> TYPE: DNA
<213> ORGANISM: Artificial Sequence
<220> FEATURE:
<223> OTHER INFORMATION: primer

<400> SEQUENCE: 23
tcctgcagat gcccatgtac actccatcac t    31

<210> SEQ ID NO 24
<211> LENGTH: 32
<212> TYPE: DNA
<213> ORGANISM: Artificial Sequence
<220> FEATURE:
<223> OTHER INFORMATION: primer

<400> SEQUENCE: 24
ctcaagcttc gcggttcttt tagcttccaa ag    32

<210> SEQ ID NO 25
<211> LENGTH: 28
<212> TYPE: DNA
<213> ORGANISM: Artificial Sequence
<220> FEATURE:
<223> OTHER INFORMATION: primer

<400> SEQUENCE: 25
ttgtacaatg aacgccgtgg ccaagatc    28

```
<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
ctcaagcttg atcacgccgc ggcgaatctg gt                          32

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
ggtcgtacta ctggtattgt gct                                    23

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
tgacaatttc acgctcagct                                        20

<210> SEQ ID NO 29
<211> LENGTH: 23
<212> TYPE: DNA
<213> ORGANISM: Artificial Sequence
<220> FEATURE:
<223> OTHER INFORMATION: primer

<400> SEQUENCE: 29
gcggtttaaa ttcagcggtc ctg                                    23

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
tccgtgcact ggctcgttaa tc                                     22

<210> SEQ ID NO 31
<211> LENGTH: 22
<212> TYPE: DNA
<213> ORGANISM: Artificial Sequence
<220> FEATURE:
<223> OTHER INFORMATION: primer

<400> SEQUENCE: 31
tgtccgaagg gttccaagct ac                                     22

<210> SEQ ID NO 32
<211> LENGTH: 24
<212> TYPE: DNA
<213> ORGANISM: Artificial Sequence
<220> FEATURE:
<223> OTHER INFORMATION: primer
```

```
<400> SEQUENCE: 32
cacagtttcc gcatagtcag tacg                                              24

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
aagatcgtcg agggagatgc tg                                                22

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
tccggccagt actcaatgct tc                                                22

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
atcttgactg agcgtggtta ttcc                                              24

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
gctggtcctg gctgtctcc                                                    19

<210> SEQ ID NO 37
<211> LENGTH: 23
<212> TYPE: DNA
<213> ORGANISM: Artificial Sequence
<220> FEATURE:
<223> OTHER INFORMATION: primer

<400> SEQUENCE: 37
gacaggccaa cgatattcat aga                                               23

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
ctatgccaca ttgattcctc att                                               23

<210> SEQ ID NO 39
```

-continued

<211> LENGTH: 23
<212> TYPE: DNA
<213> ORGANISM: Artificial Sequence
<220> FEATURE:
<223> OTHER INFORMATION: primer

<400> SEQUENCE: 39
tttcaggcgt tggttactca tac                                              23

<210> SEQ ID NO 40
<211> LENGTH: 24
<212> TYPE: DNA
<213> ORGANISM: Artificial Sequence
<220> FEATURE:
<223> OTHER INFORMATION: primer

<400> SEQUENCE: 40
tctaactatg cacgtatgca cctt                                             24

<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41
ggcttcaatt ctctggtttc a                                                21

<210> SEQ ID NO 42
<211> LENGTH: 19
<212> TYPE: DNA
<213> ORGANISM: Artificial Sequence
<220> FEATURE:
<223> OTHER INFORMATION: primer

<400> SEQUENCE: 42
ctgacaaagg cagcaccat                                                   19

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
gtttattcca aagggtgtg ct                                                22

<210> SEQ ID NO 44
<211> LENGTH: 19
<212> TYPE: DNA
<213> ORGANISM: Artificial Sequence
<220> FEATURE:
<223> OTHER INFORMATION: primer

<400> SEQUENCE: 44
gcggttgtag agatcagca                                                   19

<210> SEQ ID NO 45
<211> LENGTH: 18
<212> TYPE: DNA
<213> ORGANISM: Artificial Sequence
<220> FEATURE:
<223> OTHER INFORMATION: primer

<400> SEQUENCE: 45

```
atggaagcca agctctgg                                               18

<210> SEQ ID NO 46
<211> LENGTH: 18
<212> TYPE: DNA
<213> ORGANISM: Artificial Sequence
<220> FEATURE:
<223> OTHER INFORMATION: primer

<400> SEQUENCE: 46
ctacaggcca ggcggttt                                               18
```